(12) United States Patent
Long et al.

(10) Patent No.: US 8,410,094 B2
(45) Date of Patent: Apr. 2, 2013

(54) AMIDE COMPOUNDS, THEIR PHARMACEUTICAL COMPOSITIONS, THEIR PREPARATION METHOD AND THEIR USES

(75) Inventors: Yaqiu Long, Shanghai (CN); Xing Fan, Shanghai (CN); Dongzhi Feng, Shanghai (CN); Li Chen, Shanghai (CN); Renhai Chen, Shanghai (CN)

(73) Assignees: Shanghai Institute of Materia Medica, Chinese Academy of Sciences, Shanghai (CN); Shanghai Targetdrug Co., Ltd., Shanghai (CN)

( * ) Notice: Subject to any disclaimer, the term of this patent is extended or adjusted under 35 U.S.C. 154(b) by 0 days.

(21) Appl. No.: 13/123,455

(22) PCT Filed: Sep. 18, 2009

(86) PCT No.: PCT/CN2009/001046
§ 371 (c)(1),
(2), (4) Date: Jun. 30, 2011

(87) PCT Pub. No.: WO2010/040272
PCT Pub. Date: Apr. 15, 2010

(65) Prior Publication Data
US 2011/0251192 A1 Oct. 13, 2011

(30) Foreign Application Priority Data
Oct. 8, 2008 (CN) .......................... 2008 1 0200896

(51) Int. Cl.
*C07D 451/04* (2006.01)
*A61K 31/46* (2006.01)

(52) U.S. Cl. ..................... 514/233.2; 514/304; 544/127; 546/125

(58) Field of Classification Search .................. 546/125; 514/304
See application file for complete search history.

(56) References Cited

FOREIGN PATENT DOCUMENTS
| CN | 1437599 A | 8/2003 |
|----|-----------|--------|
| CN | 1642913 A | 7/2005 |
| CN | 1646526 A | 7/2005 |

*Primary Examiner* — Zinna Northington Davis
(74) *Attorney, Agent, or Firm* — Baker & Hostetler LLP

(57) ABSTRACT

The present invention pertains to the field of pharmaceutical chemistry and discloses 8-(3-aminopropyl)-3-exo-8-azabicyclo[3.2.1]octane-3-amino amide compounds represented by formula I, the pharmaceutical compositions, the preparation method and the use thereof. Such compounds or pharmaceutically acceptable salts thereof can be used as an antagonist of CCR5 in preparing medicaments for treating diseases mediated by CCR5, particularly HIV infection, asthma, rheumatoid arthritis, autoimmune diseases and chronic obstructive pulmonary diseases (COPD).

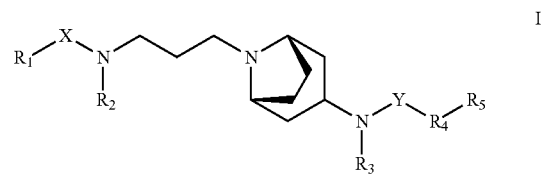

10 Claims, No Drawings

AMIDE COMPOUNDS, THEIR PHARMACEUTICAL COMPOSITIONS, THEIR PREPARATION METHOD AND THEIR USES

CROSS-REFERENCE TO RELATED APPLICATIONS

This application is a National Stage of International patent application PCT/CN2009/001046, filed on Sep. 18, 2009, which claims priority to foreign China patent application No. CN 200810200896.2, filed Oct. 8, 2008, the disclosures of which are hereby incorporated by reference in their entirety.

FIELD OF THE INVENTION

The present invention pertains to the field of pharmaceutical chemistry, particularly, to 8-(3-aminopropyl)-3-exo-8-azabicyclo[3.2.1]octane-3-amino amide compounds, the pharmaceutical compositions, the preparation method and the uses thereof. Such compounds can be used as an antagonist of CCR5.

BACKGROUND OF THE INVENTION

Chemokines are a kind of cytokines which guide the directed migration of lymphocytes, and play an important role in inflammatory reaction, white blood cells extravasation, tissue infiltration, tumorigenesis and embryonic development. Chemokines, having a molecular weight of 8~14 kDa, belong to the large family of the secreted signalling molecules, which currently comprises about 45 members with a common characteristic of having four cysteine (Cys) residues of which the positions are conserved. According to whether there are other amino acids between the two Cys residues near the N-terminal, the family is divided into four groups: CC, CXC, CXQC and C, wherein CC (also named as β-chemokines) and CXC (also named as α-chemokines) are the most two important groups.

The function of chemokines is mediated by chemokine receptors. At present, chemokine receptors are normally named in accordance with the character of the chemokines to which they specifically bind (for example, the chemokine receptors will be named as CCR if their ligands are the members of the CC chemokine subfamily). Chemokine receptors, which belong to the seven-transmembrane G-Protein-Coupled Receptor, contain seven conserved transmembrane domains formed by α-helical structure, with an extra cellular N-terminal and an intra cellular C-terminal domain. When combining with an agonist, chemokine receptors can couple to G-protein such that the extracellular signal can be transferred into cell. With the action of an agonist, chemokine receptors could trigger a series of intracellular signals and change cell behaviour, such as inhibiting the activity of adenylate cyclase (AC), triggering a flux in intracellular calcium, activating a series of protein kinase, guiding the directed migration of cells (chemotaxis) and affecting the release of cytokines.

There have currently been found 19 chemokine receptors, which are CCR1-11, CXCR1-6, XCR1 and $CX_3CR1$. Chemokine receptors are thought to be an important mediator of inflammatory reaction and autoimmune diseases (Gerard et al., Nat Immunol, 2, 108-15 (2001)). Therefore, the regulator of chemokine receptors (including agonist and antagonist) can be used in many kinds of disease, such as inflammatory or allergic diseases, allergic reaction, autoimmune diseases, inflammatory bowel diseases, scleroderma, eosinophilic myositis, tumorigenesis and metastasis.

As a member of the chemokine receptor family, CCR5, whose endogenous agonists are RANTES, MIP-1α and MIP-1β, expresses in dendritic cells, T Lymphocytes, monocytes and macrophages derived from peripheral blood cells, and immune cells and inflammatory cells participating in maintenance of a long-term inflammatory reaction. Therefore, CCR5 may regulate the recruitment of T cells to the injured sites of inflammatory response so as to provide a new target for the treatment of inflammatory reaction and autoimmune diseases. For example, CCR5-deficient mice were protected from DSS-induced serious inflammations and mucosal ulcerations (Andres et al., J. Immunol., 164, 6303-12 (2000)); and a small molecule antagonist TAK-779 of CCR5 inhibited collagen-induced arthritis in mice (Yang et al., Eur J. Immunol., 32, 2124-32 (2002)). Hence, the antagonist of CCR5 can be used in the treatment of the diseases including asthma and local disorders (such as locality dermatitis and local anaphylaxis), rheumatoid arthritis, arteriosclerosis, psoriasis, sarcoidosis and other fibrotic diseases, autoimmune diseases (such as multiple sclerosis and inflammatory bowel disease). Further, because $CD^{8+}$ T cells are related with chronic obstructive pulmonary diseases (COPD), CCR5's antagonist could be used to treat COPD also.

Besides the action in inflammation and immune reactions, chemokine receptors may also be the critical receptors during the cell invasion by parasites and viruses. For instance, Duffy receptor is the receptor for plasmodium entrying into erythrocytes, and people lacking of Duffy receptor are not easy to suffer from malaria. More importantly, several chemokine receptors participating in the invasion of HIV, are called HIV co-receptor.

It has showed that CD4 molecules on Th cells are essential for HIV invasion, but CD4 alone is not sufficient to mediate the fusion of HIV and cell. Further researches indicated that the other molecules named co-receptors of HIV invasion are CCR5, CXCR4, CCR2b, CCR3, CCR8 in chemokine receptors and, V28, STRL-33, GPR1, GPR15 and APJ in orphan receptors (Domes et al., *Virology,* 235, 179-90, (1997)). CCR5 and CXCR4 are the main co-receptors in vivo for HIV invasion, and CCR3 may involve in part of the HIV entry. CCR5 is the co-receptor of macrophage tropic (M-tropic) HIV-1, and CXCR4 is the co-receptor of T cell tropic (T-tropic) HIV-1. Therefore, CCR5 plays a key role in HIV spreading, and a substance regulating CCR5 can affect the spreading of M-tropic HIV-1 in people, and thus control the disease at an early stage. It has been found through in vitro experiments that chemokines which can bind to CCR5, including RANTES, MIP-1α and MIP-1β, could inhibit HIV infection by suppressing the invasion of M-tropic HIV-1 into cells. Some small molecular compounds that can bind to CCR5 and antagonize the function of CCR5 are also able to effectively inhibit the invasion of HIV into cells in vitro.

In summary, there is an urgent need in the art for developing compounds having a potential pharmaceutical application as a CCR5 antagonist.

SUMMARY OF THE INVENTION

The present inventor designed and synthesized the compounds represented by the formula I after an extensive research on the compounds having antagonistic effect for CCR5. Testing results show that these compounds are potent antagonists of CCR5, and have activities in vivo against HIV-1 virus and may thus be used as an inhibitor against the invasion of HIV virus and developed into drugs against HIV. The present invention is completed on this basis.

Therefore, an object of the present invention is to provide a class of 8-(3-aminopropyl)-3-exo-8-azabicyclo[3.2.1]octane-3-amino amide compounds represented by the formula I and pharmaceutically acceptable salts thereof as a CCR5 antagonist.

Another object of the present invention is to provide a method for preparing the said compounds.

Still another object of the present invention is to provide a pharmaceutical composition comprising a therapeutically effective amount of one or more compounds selected from the 8-(3-aminopropyl)-3-exo-8-azabicyclo[3.2.1]octane-3-amide compounds represented by the formula I and their pharmaceutically acceptable salts.

A further object of the present invention is to provide the use of the said compounds and their pharmaceutically acceptable salts as a CCR5 antagonist in preparing a medicament for treating diseases mediated by CCR5.

In one aspect of the present invention, provided are the 8-(3-aminopropyl)-3-exo-8-azabicyclo[3.2.1]octane-3-amide compounds represented by the follow formula I and their pharmaceutically acceptable salts.

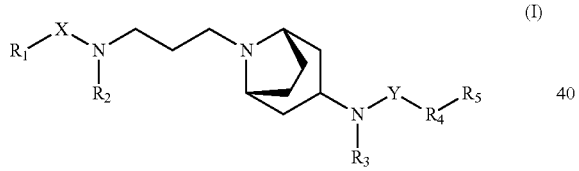

In the formula I, $R_1$ is hydrogen or a group unsubstituted or substituted by 1 to 3 substituents and selected from the group consisting of $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkoxy, amino, phenyl, benzyl, naphthyl, $C_5$-$C_{10}$ aromatic heterocyclic group and $C_4$-$C_7$ saturated heterocyclic group, wherein the heterocyclic group comprises 1 to 3 hetero atoms selected from the group consisting of N, O and S, the substituents are atoms or groups selected from the group consisting of $C_1$-$C_6$ alkyl, $C_1$-$C_6$ alkoxy, $C_3$-$C_8$ cycloalkyl, halogen, mercapto, hydroxyl, $CF_3$, CN, $NO_2$, $NR_6R_7$, $NR_6COR_7$, $NR_6COOR_7$, $NR_6SO_2R_7$, $COOR_7$, $COR_7$, $CONR_6R_7$, $SO_2R_7$, $SO_2NR_6R_7$, $OR_7$ and $OCOR_7$;

X is OCO, CO, $NR_6CO$ or $SO_2$;

$R_2$ is a group unsubstituted or substituted by 1 to 3 substituents and selected from the group consisting of phenyl, benzyl, naphthyl and $C_5$-$C_{10}$ aromatic heterocyclic group comprising 1 to 3 hetero atoms selected from the group consisting of N, O and S, wherein the substituents are atoms or groups selected from the group consisting of $C_1$-$C_6$ alkyl, $C_1$-$C_6$ alkoxy, $C_2$-$C_6$ alkenyl, $C_2$-$C_6$ alkynyl, $C_3$-$C_7$ cycloalkyl, $C_1$-$C_6$ alkylthiol, halogen, mercapto, hydroxyl, $CF_3$, CN, $NO_2$, $NR_6R_7$, $NR_6COR_7$, $NR_6COOR_7$, $NR_6SO_2R_7$, $COOR_7$, $COR_7$, $CONR_6R_7$, $SO_2R_7$, $OR_7$ and $OCOR_7$;

$R_3$ is hydrogen, $C_1$-$C_6$ alkyl, $C_3$-$C_8$ cycloalkyl, phenyl, benzyl, naphthyl, $C_5$-$C_{10}$ aromatic heterocyclic group or $C_4$-$C_7$ saturated heterocyclic group, or $R_3$ together with the attached N, Y, $R_4$ and $R_5$ may form a group of 3-isopropyl-5-methyl-4-hydro-1,2,4-triazol-4-yl;

Y is C(O)O, CO, $C(O)NR_6$ or $SO_2$;

$R_4$ is a direct bond or a group unsubstituted or substituted by 1 to 3 substituents and selected from the group consisting of $C_1$-$C_6$ alkylene, $C_1$-$C_6$ alkyleneoxy, $C_2$-$C_6$ alkenylene and $C_2$-$C_6$ alkynylene, wherein the substituents are atoms or groups selected from the group consisting of $C_1$-$C_6$ alkyl, $C_1$-$C_6$ alkoxy, halogen, amino, nitro group, nitrile group, mercapto and hydroxyl;

$R_5$ is a group unsubstituted or substituted by 1 to 3 substituents and selected from the group consisting of $C_1$-$C_6$ alkyl, $C_3$-$C_8$ cycloalkyl, adamantly, phenyl, phenoxyl, benzyl, naphthyl, $C_5$-$C_{10}$ aromatic heterocyclic group or $C_4$-$C_7$ saturated heterocyclic group, wherein the heterocyclic group comprises 1 to 3 hetero atoms selected from the group consisting of N, O and S, the substituents are atoms or groups selected from the group consisting of $C_1$-$C_6$ alkyl, $C_1$-$C_6$ alkoxy, halogen, mercapto, hydroxyl, $CF_3$, CN, $NO_2$, $NR_6R_7$, $NR_6COR_7$, $NR_6COOR_7$, $NR_6SO_2R_7$, $COOR_7$, $COR_7$, $CONR_6R_7$, $SO_2R_7$, $SO_2NR_6R_7$, $OR_7$ and $OCOR_7$, and $NR_6R_7$ may together form a cycloamine group;

$R_6$ is hydrogen, hydroxyl or $C_1$-$C_6$ alkyl;

$R_7$ is hydrogen or a group unsubstituted or substituted by 1 to 3 substituents and selected from the group consisting of $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, phenyl, benzyl, naphthyl, $C_5$-$C_{10}$ aromatic heterocyclic group and $C_4$-$C_7$ saturated heterocyclic group, wherein the heterocyclic group comprises 1 to 3 hetero atoms selected from the group consisting of N, O and S, the substituents are atoms or groups selected from the group consisting of $C_1$-$C_6$ alkyl, $C_1$-$C_6$ alkoxy, halogen, amino, nitro group, mercapto, hydroxyl, CN and $CF_3$.

In a preferable embodiment of the present invention, the compounds according to the present invention are those represented by formula II:

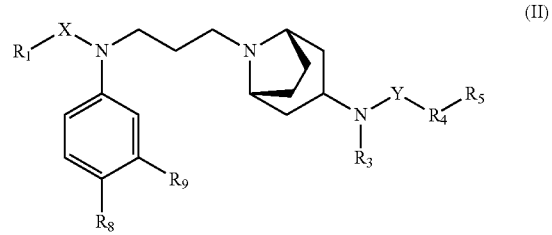

wherein, $R_1$ is 1-acetylpiperidin-4-yl, cyclohexyl, 1-methylsulfonylpiperidin-4-yl, $C_1$-$C_4$ alkyl, benzyl, phenyl or $C_1$-$C_4$ alkyl phenyl, and preferably $R_1$ is 1-acetylpiperidin-4-yl;

X is OCO, CO, $NR_6CO$ or $SO_2$, and preferably X is CO;

$R_3$ is hydrogen, $C_1$-$C_4$ alkyl or $C_3$-$C_7$ cycloalkyl, or $R_3$ together with the attached N, Y, $R_4$ and $R_5$ may form a group of 3-isopropyl-5-methyl-4-hydro-1,2,4-triazol-4-yl;

Y is C(O)O, CO, C(O)NH or $SO_2$;

$R_4$ is a direct bond, $C_1$-$C_4$ alkylene, $C_1$-$C_4$ alkyleneoxy or $C_1$-$C_4$ alkylene substituted by hydroxyl;

$R_5$ is a group unsubstituted or substituted by 1 to 3 substituents and selected from the group consisting of $C_1$-$C_4$ alkyl, $C_3$-$C_8$ cycloalkyl, adamantly, phenyl, phenoxyl, benzyl, naphthyl, or $C_5$-$C_{10}$ aromatic heterocyclic group, wherein the heterocyclic group comprises 1 to 2 hetero atoms selected from the group consisting of N, O and S, the substituents are atoms or groups selected from the group consisting of $C_1$-$C_4$ alkyl, $C_1$-$C_4$ alkoxy, halogen, hydroxyl, $CF_3$, CN, $NO_2$, $NR_6R_7$, $NR_6COR_7$, $NR_6COOR_7$, $NR_6SO_2R_7$, $COOR_7$, $COR_7$, $CONR_6R_7$, $SO_2R_7$, $SO_2NR_6R_7$, $OR_7$ and $OCOR_7$, and $NR_6R_7$ may form a cycloamine group, wherein $R_6$ is hydrogen or $C_1$-$C_6$ alkyl and $R_7$ is hydrogen, $C_1$-$C_6$ alkyl or $C_1$-$C_6$ alkoxy;

$R_8$ and $R_9$ are each independently hydrogen, halogen, hydroxyl, nitrile group, mercapto, nitro group, $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy or $C_1$-$C_6$ alkylthio, wherein $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy or $C_1$-$C_6$ alkylthio may be selectively substituted with halogen, hydroxyl, amino, $C_3$-$C_7$ cycloalkyl, nitrile group or mercapto.

$R_5$ is a group unsubstituted or substituted by 1 to 3 substituents and selected from the group consisting of phenyl, phenoxyl, naphthyl, adamantyl, morpholinyl, piperazinyl, piperidinyl, pyrrolyl, thienyl, imidazolyl, triazolyl, tetrazolyl, furyl, pyranyl, indolyl, quinolyl, benzopyranyl, benzothienyl, benzofuryl, benzimidazolyl or benzotriazolyl, wherein the substituents are atoms or groups selected from the group consisting of $C_1$-$C_4$ alkyl, $C_1$-$C_4$ alkoxy, halogen, hydroxyl, $CF_3$, $NO_2$, $NR_6R_7$, $NR_6COR_7$, $NR_6COOR_7$, $NR_6SO_2R_7$, $COOR_7$, $COR_7$, $CONR_6R_7$, $SO_2R_7$, $SO_2NR_6R_7$, $OR_7$ and $OCOR_7$, and $NR_6R_7$ may form a cycloamine group, wherein $R_6$ is hydrogen or $C_1$-$C_4$ alkyl, and $R_7$ is hydrogen, $C_1$-$C_4$ alkyl or $C_1$-$C_4$ alkoxy;

$R_8$ is hydrogen, halogen or $C_1$-$C_4$ alkyl;

$R_9$ is hydrogen or halogen.

In the present invention, the compounds prepared in the examples are especially preferable.

The pharmaceutically acceptable salts of the 8-(3-aminopropyl)-3-exo-8-azabicyclo[3.2.1]octane-3-amino amide compounds according to the present invention may be the salts prepared by reacting the compounds according to the present invention with hydrochloric acid, tartaric acid, citric acid, hydrobromic acid, hydrogen iodide, nitric acid, phosphoric acid, sulfuric acid or methanesulfonic acid according to a general method for pharmaceutically preparing a salt.

In the second aspect of the present invention, provided is a method for preparing the compounds of the present invention, which can be illuminated by the following procedure:

The General Procedure:

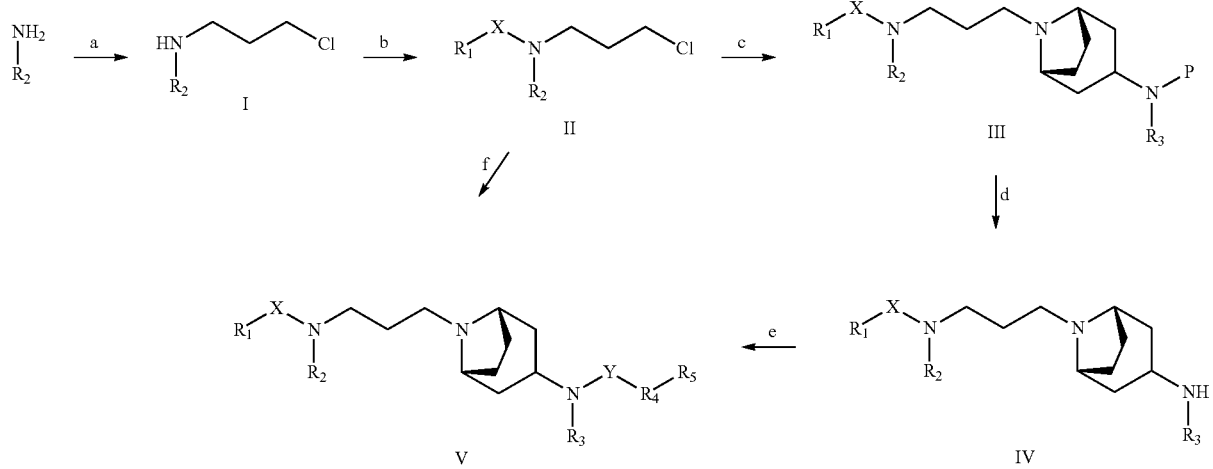

As for the compounds represented by formula II, it is preferable that:

$R_1$ is 1-acetylpiperidin-4-yl, cyclohexyl, 1-methylsulfonylpiperidin-4-yl, $C_1$-$C_4$ alkyl, benzyl, phenyl or $C_1$-$C_4$ alkyl phenyl, and preferably, $R_1$ is 1-acetylpiperidin-4-yl;

X is OCO, CO, $NR_6CO$ or $SO_2$, and preferably X is CO;

$R_3$ is hydrogen, or $R_3$ together with the attached N, Y, $R_4$ and $R_5$ may form a group of 3-isopropyl-5-methyl-4-hydro-1,2,4-triazol-4-yl;

$R_4$ is a direct bond, $C_1$-$C_4$ alkylene, $C_1$-$C_4$ alkyleneoxy or $C_1$-$C_4$ alkylene substituted by hydroxyl;

wherein, $R_1$, $R_2$, $R_3$, $R_4$, $R_5$, X and Y are defined the same as the above;

P is an amino protecting group selected from the group consisting of t-butoxy carbonyl, benzyloxycarbonyl, benzyl, 9-fluorenylmethoxycarbonyl, $CH_3CO$ and $CH_3OCO$;

Step a): $R_2NH_2$ reacts with 1-bromo-3-chloropropane through a nucleophilic substitution reaction in the presence of an alkali to prepare a N-substituted 3-chloropropylamine compound I;

Step b): the N-substituted 3-chloropropylamine compound I reacts with an aldehyde or a ketone through a reductive amination reaction, or with an acid through a coupling reaction, or with halogenated hydrocarbon through a nucleophilic substitution reaction to obtain a N-trisubstituted 3-chloropropylamine compound II;

Step c): a 3-exo-3-amino-8-azabicyclo[3.2.1]octane secondary amine compound protected at 3-N atom reacts with the N-trisubstituted 3-chloropropylamine compound II through a nucleophilic substitution reaction in the presence of an alkali to obtain a protected 8-(3-aminopropyl)-3-exo-8-azabicyclo[3.2.1]octane-3-amino amide compound III;

Step d): the compound III is deprotected the amine protecting groups by acidic or alkaline hydrolysis or hydrogenolysis depending on the amine protecting groups to obtain a compound IV;

Step e): the free amine compound IV reacts with an acid through a coupling reaction, or with an acyl chloride through a substitution reaction, or with an isocyanate through an addition reaction, or with a halohydrocarbon through a nucleophilic substitution reaction to prepare a compound V, i.e. the 8-(3-aminopropyl)-3-exo-8-azabicyclo[3.2.1]octane-3-amino amide compound of the present invention; or Step f): the N-trisubstituted 3-chloropropylamine compound II reacts with a 3-exo-8-azabicyclo[3.2.1]octane-3-amino amide compound through a nucleophilic substitution in the presence of an alkali to prepare a compound V, i.e. the 8-(3-aminopropyl)-3-exo-8-azabicyclo[3.2.1]octane-3-amino amide compound of the present invention.

A Procedure for preparing the 3-exo-3-amino-8-azabicyclo[3.2.1]octane Secondary Amine Compound Protected at 3-N Atom is as Follows:

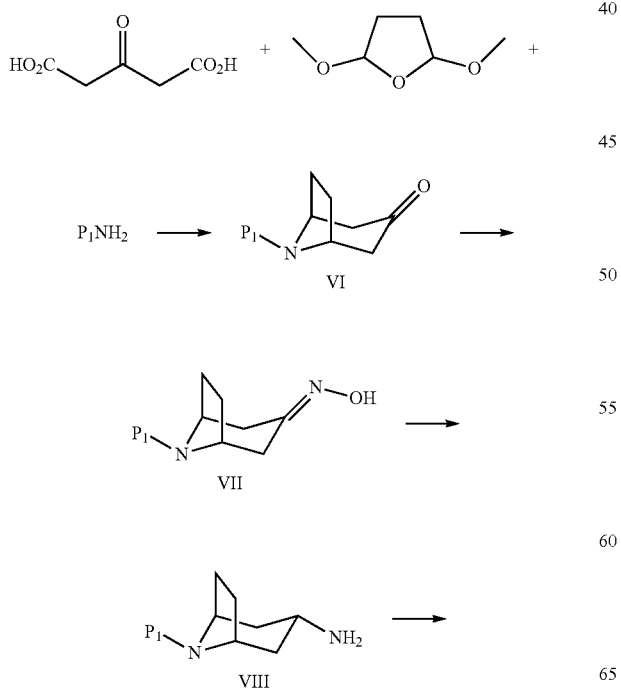

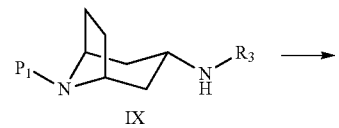

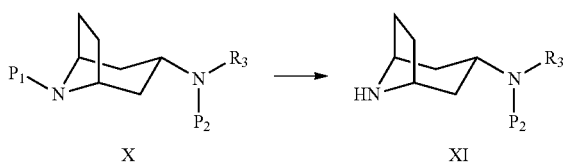

wherein $R_3$ is defined the same as the above, and $P_1$ and $P_2$ are respectively a common amino-protecting group, such as Boc, Cbz, Bn, Fmoc, $CH_3CO$ or $CH_3OCO$ etc.;

a protected amino compound reacts with 3-carbonyl-1,5-glutaric acid and 2,5-dimethoxytetrahydrofuran through a Robinson-Schopf reaction to prepare a protected 8-azabicyclo[3.2.1]octan-3-one VI, which is subject to an oximation reaction to obtain a compound VII; the compound VII is reduced to prepare a protected 3-exo-8-azabicyclo[3.2.1]octane-3-amino compound VIII; various substituents $R_3$ is introduced and the secondary amine compound is protected to prepare a compound X, which is deprotected the protecting group $P_1$ to prepare a 3-exo-3-amino-8-azabicyclo[3.2.1]octane secondary amine compound XI protected at 3-N atom. In the third aspect of the invention, provided is a pharmaceutical composition, which comprises an therapeutically effective amount of one or more compounds selected from the 8-(3-aminopropyl)-3-exo-8-azabicyclo[3.2.1]octane-3-amino amide compounds of formula I and their pharmaceutically acceptable salts, and may further comprise pharmaceutically acceptable adjuvants. The pharmaceutical composition may further comprise a proteinase inhibitor and/or a reverse transcriptase inhibitor.

In the fourth aspect of the invention, provided is a use of the compounds of the formula I or their pharmaceutically acceptable salts as an antagonist of CCR5 for preparing a medicament for treating diseases mediated by CCR5, more particularly, for preparing a medicament for treating HIV infection, asthma, rheumatoid arthritis, autoimmune diseases or chronic obstructive pulmonary diseases (COPD).

DETAILED DESCRIPTION OF THE INVENTION

Hereinafter, the present invention will be further described in detail with reference to the following examples. It should be understood that the following examples only intend to illuminate the present invention without any limitation on the scope of the present invention.

PREPARATION EXAMPLE
Example 1
Compound 7a: 1-acetyl-N-(3-chloro-4-methylphenyl)-N-(3-(3-exo-(2-phenyl acetamide)-8-azabicyclo[3.2.1]oct-8-yl)propyl)-4-piperidinylcarboxamide
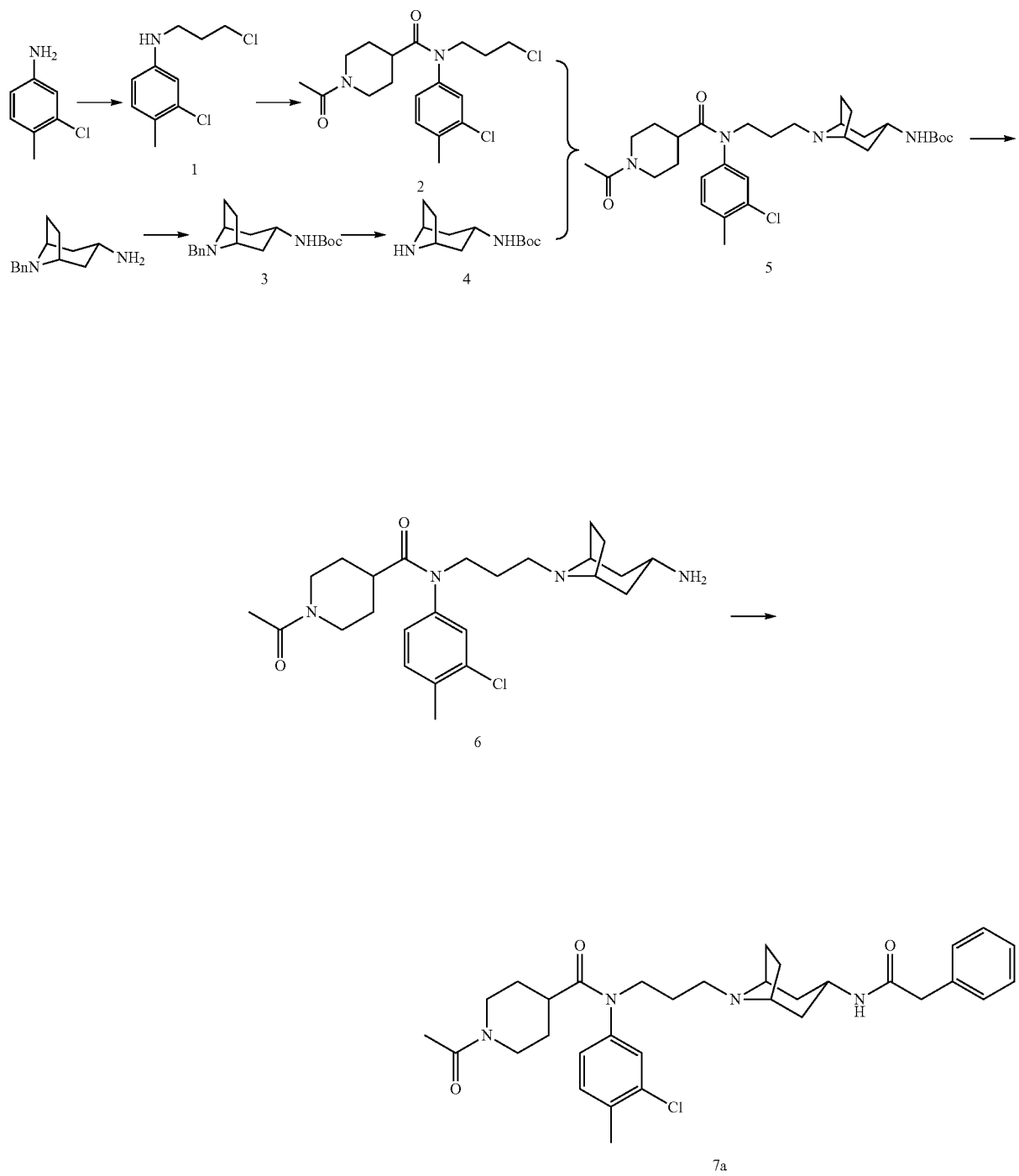

Step 1: 3-chloro-N-(3-chloropropyl)-4-methylaniline

To a solution of 3-chloro-4-methylaniline (14.16 g, 100 mmol) in DMF (N,N-dimethyl formamide) (10 mL), were added 1-bromo-3-chloropropane (30.5 mL, 300 mmol), potassium iodide (1.66 g, 10 mmol) and triethylamine (60 mL). The mixture was stirred for 3 days at room temperature, then distilled off the solvents with a low boiling point, diluted with ethyl ether, and washed by a saturated saline. The separated organic phase was dried with sodium sulfate and concentrated under reduced pressure. The concentrate was separated through column chromatography (petroleum ether/ethyl acetate=25/1, v/v) to obtain compound 1 as light brown oil (18.64 g, yield: 86%).

$^1$HNMR (CDCl$_3$, 300 MHz) δ: 7.01-6.98 (d, 1H, J=8.1 Hz), 6.64-6.63 (d, 1H, J=2.4 Hz), 6.46-6.42 (dd, 1H, J=2.4 Hz, 5.7 Hz), 3.66-3.62 (t, 2H, J=6.3 Hz), 3.31-3.27 (t, 2H, J=6.6 Hz), 2.45 (s, 3H), 2.09-2.01 (m, 2H).

Step 2: 1-acetyl-N-(3-chloro-4-methylphenyl)-N-(3-chloropropyl)-4-piperidinylcarboxamide The above prepared compound 1 (2.18 g, 10 mmol) was dissolved in dichloromethane (50 mL), and triethylamine (5.53 mL, 40 mmol) and 1-acetyl-4-piperidylformyl chloride (5.69 g, 30 mmol) were sequently added into the solution under ice cooling. The mixture was stirred for 1 hour under the same temperature, added with a saturated sodium bicarbonate solution (40 mL) under ice cooling, and diluted with dichloromethane (50 mL). The organic phase was separated, dried with sodium sulfate and concentrated. The concentrate was separated through column chromatography (dichloromethane/ethyl acetate=1/1, v/v) to obtain compound 2 as light brown oil (2.6 g, yield: 70%).

$^1$HNMR (CDCl$_3$, 300 MHz) δ: 7.33-7.30 (d, 1H, J=8.1 Hz), 7.18 (d, 1H, J=2.1 Hz), 6.99-6.96 (dd, 1H, J=1.8 Hz, 6.0 Hz), 4.53-4.50 (m, 1H), 3.79-3.74 (t, 2H, J=7.2 Hz), 3.55-3.51 (t, 2H, J=6.3 Hz), 2.85 (br-s, 1H), 2.43 (s, 3H), 2.41-2.34 (m, 2H), 2.05 (s, 3H), 2.00 (m, 3H), 1.84-1.54 (m, 4H).

Step 3: tert-butyl 8-benzyl-3-exo-8-aza-bicyclo[3.2.1]octan-3-ylcarbamate

To a solution of 8-benzyl-3-exo-8-azabicyclo[3.2.1]octyl-3-amine (7.231 g, 33.2 mmol) in dichloromethane (100 mL), were added di-tert-butyl dicarbonate (7.95 g, 36.5 mmol) and triethylamine (5.5 mL, 39.8 mmol). The mixture was refluxed and stirred for 12 hour, and then distilled off tetrahydrofuran under reduced pressure. The residue was diluted with dichloromethane (100 mL), washed sequently by 5% sodium bicarbonate solution (100 mL) and saturated saline (100 mL), dried with anhydrous sodium sulfate and concentrated. The concentrate was separated through column chromatography (petroleum ether/ethyl acetate=1/1, v/v) to obtain the compound 3 as a white solid (8.664 g, yield: 82%).

$^1$HNMR (CDCl$_3$, 300 MHz) δ: 7.37-7.23 (m, 5H), 4.32 (br, 1H), 3.81 (br, 1H), 3.53 (s, 2H), 3.21-3.19 (m, 2H), 2.04-2.00 (m, 2H), 1.84-1.77 (m, 2H), 1.70-1.66 (m, 2H), 1.52-1.48 (m, 2H), 1.43 (s, 9H).

Step 4: tert-butyl-3-exo-8-aza-bicyclo[3.2.1]octan-3-ylcarbamate

To a solution of the above prepared compound 3 (954 mg, 3 mmol) in methanol (10 mL), were added 10% palladium-on-carbon (Pd/C) (95 mg) and ammonium formate (1323 mg, 21 mmol). The mixture was refluxed and stirred for 12 hour, then distilled off methanol under reduced pressure. The residue was diluted with dichloromethane (10 mL), then washed by saturated saline (10 mL), dried with anhydrous sodium sulfate and concentrated to obtain the compound 4 as a white solid (667 mg, yield: 92%).

$^1$HNMR (CDCl$_3$, 300 MHz) δ: 4.64 (br, 1H), 3.87-3.70 (m, 3H), 2.06-1.95 (m, 4H), 1.87-1.85 (m, 2H), 1.77-1.68 (m, 2H), 1.43 (s, 9H).

Step 5: tert-butyl-8-(3-(1-acetyl-N-(3-chloro-4-methylphenyl)-4-piperidinylcarboxamido)propyl)-3-exo-8-azabicyclo[3.2.1]octan-3-ylcarbamate The above obtained compound 4 (937 mg, 3.87 mmol) was dissolved in acetonitrile (20 mL), and then the compound 2 (1440 mg, 3.87 mmol), potassium iodide (643 mg, 3.87 mmol) and potassium carbonate (1603 mg, 11.62 mmol) were sequently added into the solution. The mixture was heated to reflux for 6 hours, then cooled to room temperature, distilled off acetonitrile under reduced pressure, diluted with dichloromethane (20 mL), and washed by saturated saline (20 mL). The separated organic phase was dried with anhydrous sodium sulfate and concentrated. The concentrate was separated through column chromatography (dichloromethane/methanol=20/1, v/v) to obtain the compound 5 as a white solid (960 mg, yield: 43%).

$^1$HNMR (CDCl$_3$, 300 MHz) δ: 7.38-7.35 (m, 1H), 7.31-7.26 (m, 2H), 5.13 (br, 1H), 4.02-3.97 (m, 1H), 3.85-3.74 (m, 4H), 3.66-3.60 (m, 1H), 2.94-2.81 (m, 3H), 2.41 (s, 3H), 2.24-2.16 (m, 3H), 2.04 (s, 3H), 1.79-1.63 (m, 14H), 1.42 (s, 9H).

Step 6: 1-acetyl-N-(3-(3-exo-amino-8-azabicyclo[3.2.1]oct-8-yl)propyl)-N-(3-chloro-4-methylphenyl)-4-piperidinylcarboxamide The above obtained compound 5 (57 mg, 0.1 mmol) was dissolved in dichloromethane (2 mL), and then trifluoroacetic acid (46 μL, 0.6 mmol) was added therein.

The mixture was stirred for 8 hour at room temperature, followed by poured into water (4 mL). The pH of the aqueous phase was adjusted to 12 by using sodium hydroxide, extracted twice with dichloromethane (5 mL). The combined organic phase was washed by saturated saline (5 mL), dried with sodium sulfate and concentrated to obtain the compound 6 as a white solid (33 mg, yield: 69%).

Step 7 compound 7a: 1-acetyl-N-(3-chloro-4-methylphenyl)-N-(3-(3-exo-(2-phenylacetamido)-8-azabicyclo[3.2.1]oct-8-yl)propyl)-4-piperidinylcarboxamide The above obtained compound 6 (76 mg, 0.16 mmol) was dissolved in dichloromethane (2 mL), and then phenylacetic acid (26 mg, 0.19 mmol), EDCI (1-ethyl-3-(3-dimethyl propylamine)carbodiimide hydrochloride) (46 mg, 0.24 mmol), HOBt (1-hydroxy benzotriazole) (32 mg, 0.24 mmol) and N-methylmorpholine (35 μL, 0.32 mmol) were added therein. The mixture was stirred for 12 hour at room temperature, and distilled off dichloromethane under reduced pressure. The residue was separated through column chromatography (dichloromethane/methanol=20/1, v/v) to obtain the 7a as a white foam-like solid (63 mg, yield: 66%).

$^1$HNMR (CDCl$_3$, 300 MHz) δ: 7.28-7.20 (m, 4H), 7.16-7.11 (m, 3H), 6.94-6.91 (m, 1H), 5.49 (d, 1H, J=8.7 Hz), 4.46-4.42 (m, 1H), 4.12-4.02 (m, 1H), 3.71-3.65 (m, 1H), 3.44 (s, 2H), 3.20 (br, 2H), 2.82-2.72 (m, 1H), 2.34 (s, 3H), 2.31-2.25 (m, 4H), 1.97 (s, 3H), 1.89-1.85 (m, 2H), 1.70-1.36 (m, 12H);

EI (LR-MS): 578 (M)$^+$, 257 (100);
EI (HR-MS): calc for. 578.3024. found 578.3006;

The follow Examples 2-26 have the similar reaction conditions as Example 1, except that a derivative from benzoic acid, phenylacetic acid and phenylpropionic acid was used to replace the phenylacetic acid in the last step.

Example 2

Compound 7b:

1-acetyl-N-(3-chloro-4-methylphenyl)-N-(3-(3-exo-(2-(4-fluorphenyl)acetamido)-8-azabicyclo[3.2.1]oct-8-yl)propyl)-4-piperidinylcarboxamide

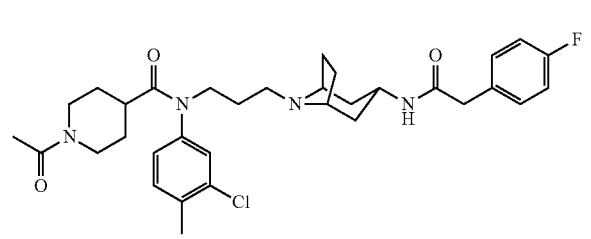 [SMILES: CC(=O)N1CCC(C(=O)N(CCCN2C3CCC2CC(NC(=O)Cc2ccc(F)cc2)C3)c2ccc(C)c(Cl)c2)CC1]

2-(4-fluorophenyl)acetic acid (commercially available from ACROS Reagent Company, CAS: 405-50-5) was used instead of phenylacetic acid in Example 1 in step 7. A white foam-like solid (50 mg, yield: 51%)

$^1$HNMR (CDCl$_3$, 300 MHz) δ: 7.24-7.22 (m, 1H), 7.16-7.12 (m, 3H), 6.98-6.91 (m, 3H), 5.90 (d, 1H, J=8.1 Hz), 4.47-4.42 (m, 1H), 4.18-4.09 (m, 1H), 3.71-3.59 (m, 3H), 3.39 (s, 2H), 3.09 (br, 2H), 2.82-2.72 (m, 1H), 2.51-2.46 (m, 2H), 2.35 (s, 3H), 2.33-2.26 (m, 2H), 1.98-1.97 (m, 1H), 1.97 (s, 3H), 1.96-1.92 (m, 1H), 1.77-1.65 (m, 9H), 1.60-1.53 (m, 3H);

EI (LR-MS): 596 (M)$^+$, 275 (100);
EI (HR-MS): calc for. 596.2940. found 596.2929.

Example 3

Compound 7c:

1-acetyl-N-(3-chloro-4-methylphenyl)-N-(3-(3-exo-(2-(4-chlorphenyl)acetamido)-8-azabicyclo[3.2.1]oct-8-yl)propyl)-4-piperidinylcarboxamide 2-(4-chlorophenyl)acetic acid (commercially available from ACROS Reagent Company, CAS: 1878-66-6) was used instead of phenylacetic acid in Example 1 in step 7. A white foam-like solid (58 mg, yield: 58%)

$^1$HNMR (CDCl$_3$, 300 MHz) δ: 7.24-7.21 (m, 3H), 7.11-7.09 (m, 3H), 6.93-6.90 (m, 1H), 5.55 (d, 1H, J=9.0 Hz), 4.46-4.41 (m, 1H), 4.07-4.04 (m, 1H), 3.71-3.57 (m, 4H), 3.39 (s, 2H), 3.19 (br, 1H), 2.81-2.72 (m, 1H), 2.46 (br, 4H), 2.35 (s, 3H), 1.98 (s, 3H), 1.88-1.85 (m, 2H), 1.65-1.49 (m, 11H);

EI (LR-MS): 612 (M)$^+$, 165 (100);
EI (HR-MS): calc for. 612.2634. found 612.2626.

Example 4

Compound 7d: 1-acetyl-N-(3-chloro-4-methylphenyl)-N-(3-(3-exo-(2-(4-(trifluoromethyl)phenyl)acetamido)-8-azabicyclo[3.2.1]oct-8-yl)propyl)-4-piperidinylcarboxamide 2-(4-(trifluoromethyl)phenyl)acetic acid (commercially available from ACROS Reagent Company, CAS: 32857-62-8) was used instead of phenylacetic acid in Example 1 in step 7.

A white foam-like solid (63 mg, yield: 53%)

$^1$HNMR (CDCl$_3$, 300 MHz) δ: 7.51 (d, 2H, J=7.8 Hz), 7.30 (d, 2H, J=7.8 Hz), 7.22 (d, 1H, J=8.4 Hz), 7.12 (d, 1H, J=1.8 Hz), 6.93 (dd, 1H, J=1.8 Hz, 8.4 Hz), 5.67 (d, 1H, J=8.4 Hz), 4.46-4.42 (m, 1H), 4.13-4.02 (m, 1H), 3.71-3.66 (m, 1H), 3.62-3.57 (m, 2H), 3.47 (s, 2H), 3.23 (br, 2H), 2.82-2.72 (m, 1H), 2.63-2.59 (m, 2H), 2.34 (s, 3H), 2.31-2.24 (m, 2H), 1.97 (s, 3H), 1.92-1.87 (m, 2H), 1.75-1.52 (m, 12H);

EI (LR-MS): 646 (M)$^+$, 325 (100);

EI (HR-MS): calc for. 646.2898. found 646.2894.

Example 5

Compound 7e:

1-acetyl-N-(3-chloro-4-methylphenyl)-N-(3-(3-exo-(2-(1-adamantyl)acetamido)-8-azabicyclo[3.2.1]oct-8-yl)propyl)-4-piperidinylcarboxamide

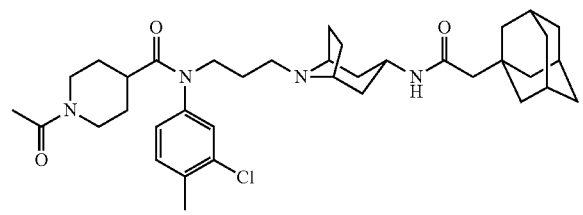 [SMILES: CC(=O)N1CCC(C(=O)N(CCCN2C3CCC2CC(NC(=O)CC24CC5CC(CC(C5)C2)C4)C3)c2ccc(C)c(Cl)c2)CC1]

2-(1-adamantyl)acetic acid (commercially available from Aldrich Reagent Company, CAS: 4942-47-6) was used instead of phenylacetic acid in Example 1 in step 7.

A white foam-like solid (60 mg, yield: 51%)

$^1$HNMR (CDCl$_3$, 300 MHz) δ: 7.27-7.23 (m, 1H), 7.14 (dd, 1H, J=1.8 Hz, 5.4 Hz), 7.04-6.93 (m, 1H), 5.60 (br, 1H), 4.48-4.43 (m, 1H), 4.20-4.04 (m, 1H), 3.72-3.59 (m, 3H), 3.39 (br, 1H), 2.82-2.73 (m, 1H), 2.52-2.47 (m, 2H), 2.35 (s, 3H), 2.32-2.18 (m, 4H), 2.14-2.04 (m, 2H), 1.98 (s, 3H), 1.95-1.88 (m, 5H), 1.81-1.75 (m, 8H), 1.71-1.52 (m, 15H);

EI (LR-MS): 637 (M+1)$^+$, 636 (M)$^+$, 235 (100);

EI (HR-MS): calc for. 636.3806. found 636.3799.

Example 6

Compound 7f:

1-acetyl-N-(3-chloro-4-methylphenyl)-N-(3-(3-exo-(2-(4-nitrophenyl)acetamido)-8-azabicyclo[3.2.1]oct-8-yl)propyl)-4-piperidinylcarboxamide

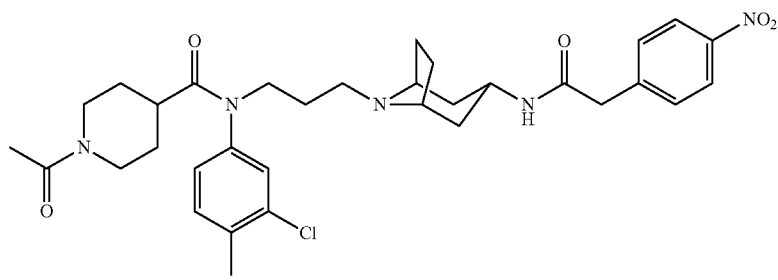 [SMILES: CC(=O)N1CCC(C(=O)N(CCCN2C3CCC2CC(NC(=O)Cc2ccc([N+](=O)[O-])cc2)C3)c2ccc(C)c(Cl)c2)CC1]

2-(4-nitrophenyl)acetic acid (commercially available from ACROS Reagent Company, CAS: 104-03-0) was used instead of phenylacetic acid in Example 1 in step 7.

A white foam-like solid (52 mg, yield: 51%)

$^1$HNMR (CDCl$_3$, 300 MHz) δ: 8.11 (d, 2H, J=8.4 Hz), 7.38 (d, 2H, J=8.4 Hz), 7.25-7.22 (m, 1H), 7.13 (s, 1H), 6.96-6.93 (m, 1H), 5.88 (br, 1H), 4.47-4.42 (m, 1H), 4.13-4.06 (m, 1H), 3.72-3.67 (m, 1H), 3.63-3.58 (m, 2H), 3.51 (s, 2H), 3.28 (br, 2H), 2.82-2.72 (m, 1H), 2.35 (s, 3H), 2.30-2.27 (m, 4H), 1.98 (s, 3H), 1.93-1.89 (m, 2H), 1.74-1.57 (m, 12H);

EI (LR-MS): 623 (M)$^+$, 112 (100);

EI (HR-MS): calc for. 623.2874. found 623.2875.

Example 7

Compound 7g: 1-acetyl-N-(3-chloro-4-methylphenyl)-N-(3-(3-exo-(2-(4-hydroxyphenyl)acetamido)-8-azabicyclo[3.2.1]oct-8-yl)propyl)-4-piperidinylcarboxamide

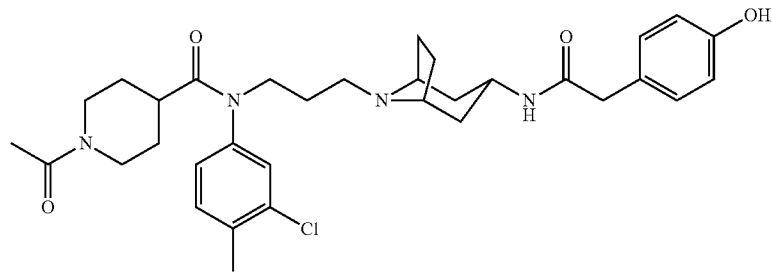 [SMILES: CC(=O)N1CCC(C(=O)N(CCCN2C3CCC2CC(NC(=O)Cc2ccc(O)cc2)C3)c2ccc(C)c(Cl)c2)CC1]

2-(4-hydroxyphenyl)acetic acid (commercially available from ACROS Reagent Company, CAS: 156-38-7) was used instead of phenylacetic acid in Example 1 in step 7. A white foam-like solid (53 mg, yield: 56%)

$^1$HNMR (CDCl$_3$, 300 MHz) δ: 7.27-7.25 (m, 1H), 7.16 (d, 1H, J=1.8 Hz), 7.02-6.95 (m, 3H), 6.74 (d, 2H, J=8.4 Hz), 5.64 (d, 1H, J=7.5 Hz), 4.51-4.47 (m, 1H), 4.19-4.07 (m, 1H), 3.78-3.61 (m, 3H), 3.42 (s, 2H), 3.30 (br, 2H), 2.88-2.80 (m, 1H), 2.40 (s, 3H), 2.34-2.29 (m, 3H), 2.05 (s, 3H), 1.97-1.93 (m, 2H), 1.77-1.70 (m, 8H), 1.63-1.50 (m, 5H);

EI (LR-MS): 594 (M)$^+$, 273 (100);

EI (HR-MS): calc for. 594.2973. found 594.2981.

Example 8

Compound 7h: 1-acetyl-N-(3-chloro-4-methylphenyl)-N-(3-(3-exo-(2-(3,4-dichlorophenyl)acetamido)-8-azabicyclo[3.2.1]oct-8-yl)propyl)-4-piperidinylcarboxamide

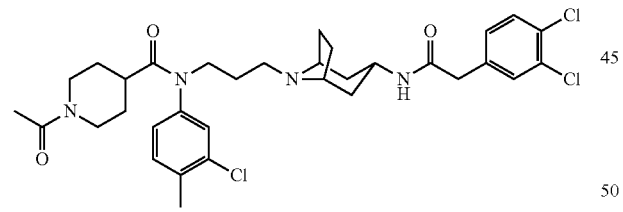

2-(3,4-dichlorophenyl)acetic acid (commercially available from ACROS Reagent Company, CAS: 5807-30-7) was used instead of phenylacetic acid in Example 1 in step 7.

A white foam-like solid (70 mg, yield: 68%)

$^1$HNMR (CDCl$_3$, 300 MHz) δ: 7.33-7.29 (m, 2H), 7.24-7.23 (m, 1H), 7.12 (br, 1H), 7.04-7.01 (m, 1H), 6.94-6.91 (m, 1H), 5.60 (d, 1H, J=7.5 Hz), 4.47-4.42 (m, 1H), 4.07 (br, 1H), 3.72-3.61 (m, 3H), 3.36 (s, 2H), 3.20 (br, 2H), 2.82-2.73 (m, 1H), 2.35 (s, 3H), 2.32-2.26 (m, 3H), 1.98 (s, 3H), 1.89-1.86 (m, 2H), 1.72-1.53 (m, 13H);

EI (LR-MS): 646 (M)$^+$, 235 (100);

EI (HR-MS): calc for. 646.2244. found 646.2253.

Example 9

Compound 7i:

1-acetyl-N-(3-chloro-4-methylphenyl)-N-(3-(3-exo-(2-(4-(pyrrolidine-1-sulfonyl)phenyl)acetamido)-8-azabicyclo[3.2.1]oct-8-yl)propyl)-4-piperidinylcarboxamide

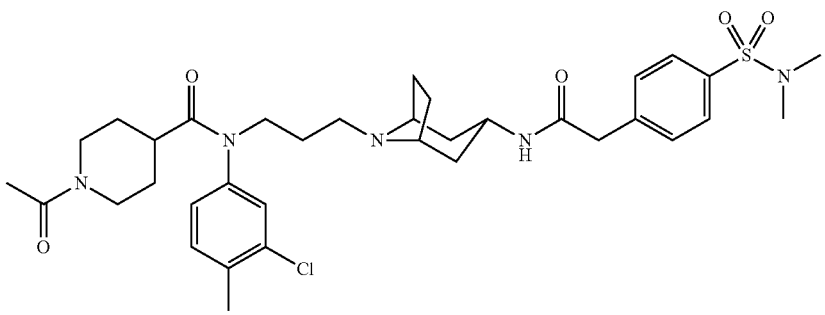 [SMILES: CC(=O)N1CCC(C(=O)N(CCCN2C3CCC2CC(NC(=O)Cc2ccc(S(=O)(=O)N(C)C)cc2)C3)c2ccc(C)c(Cl)c2)CC1]

Preparation of Starting Materials

Step (1): the preparation of 4-chlorosulfonylphenyl acetic acid ethyl ester

The chlorosulfonic acid (16.6 mL, 250 mmol) was added dropwise into ethyl phenylacetate (8.2 g, 50 mmol) under stirring at 40° C. Thereafter, the mixture was stirred for 0.5 hour at room temperature, and then poured on ice and extracted with dichloromethane. The combined organic phase was washed by saline, dried with sodium sulfate and concentrated under reduced pressure. The concentrate was separated through column chromatography (petroleum ether/ethyl acetate=6/1, v/v) to obtain yellow oil (7.4 g, yield: 56%).

Step (2): 4-(1-pyrrolidine)sulfonylphenylacetic acid ethyl ester

A solution of 4-chlorosulfonylphenylacetic acid ethyl ester (524 mg, 2 mmol) in tetrahydrofuran (10 mL) was cooled to 0° C., and pyrrolidine (0.2 mL, 2.4 mmol) and triethylamine (0.84 mL) were added therein. The mixture was warmed to room temperature and stirred for 1 hour. Then the reaction mixture was diluted with dichloromethane, and washed with saline. The organic phase was dried with sodium sulfate and concentrated under reduced pressure. The concentrate was separated through column chromatography (petroleum ether/ethyl acetate=3/1, v/v) to obtain a yellow oil (378 mg, yield: 63%).

Step (3): 4-(1-pyrrolidine)sulfonylphenylacetic acid 4-(1-pyrrolidine)sulfonylphenylacetic acid ethyl ester (352 mg, 1.18 mmol) was dissolved in a mixed solution of 2N sodium hydroxide solution (10 mL) and methanol (10 mL) and stirred for 1.5 hour at room temperature. The reaction mixture was evaporated of methanol, diluted with a small amount of water, and extracted with ethyl acetate. The aqueous phase was adjusted by 1N hydrochloric acid solution to pH 2, and then extracted with dichloromethane. The combined organic phase was washed with saline, dried with sodium sulfate and concentrated under reduced pressure. The obtained solid was subject to a recrystallization (petroleum ether/dichloromethane) to prepare a white needlelike crystal (200 mg, yield: 98%).

$^1$HNMR (CDCl$_3$, 300 MHz) δ: 7.80 (d, 2H, J=8.1 Hz), 7.45 (d, 2H, J=8.1 Hz), 3.24 (t, 4H, J=6.6 Hz), 1.79-1.74 (m, 4H).

The object compound was obtained following the method in example 1 except using 4-(1-pyrrolidine)sulfonyl phenylacetic acid instead of phenylacetic acid in Example 1 in step 7:

A white foam-like solid (48 mg, yield: 42%)

$^1$HNMR (CDCl$_3$, 300 MHz) δ: 7.71 (d, 1H, J=8.1 Hz), 7.35 (d, 2H, J=8.1 Hz), 7.23 (d, 1H, J=7.8 Hz), 7.13 (d, 1H, J=1.8 Hz), 6.94 (dd, 1H, J=1.8 Hz, 7.8 Hz), 5.79 (d, 1H, J=8.7 Hz), 4.46-4.42 (m, 1H), 4.14-4.03 (m, 1H), 3.71-3.67 (m, 1H), 3.63-3.58 (m, 2H), 3.48 (s, 2H), 3.25 (br, 2H), 3.20-3.15 (m, 4H), 2.82-2.73 (m, 1H), 2.35 (s, 3H), 2.32-2.23 (m, 3H), 2.15-2.09 (m, 6H), 1.98 (s, 3H), 1.92-1.88 (m, 2H), 1.70-1.53 (m, 11H);

EI (LR-MS): 711 (M)$^+$, 139 (100);

EI (HR-MS): calc for. 711.3221. found 711.3232.

Example 10

Compound 7j: 1-acetyl-N-(3-chloro-4-methylphenyl)-N-(3-(3-exo-(2-(4-(N,N-dimethylsulphonyl)phenyl)acetamido)-8-azadicyclo[3.2.1]oct-8-yl)propyl)-4-piperidinylcarboxamide

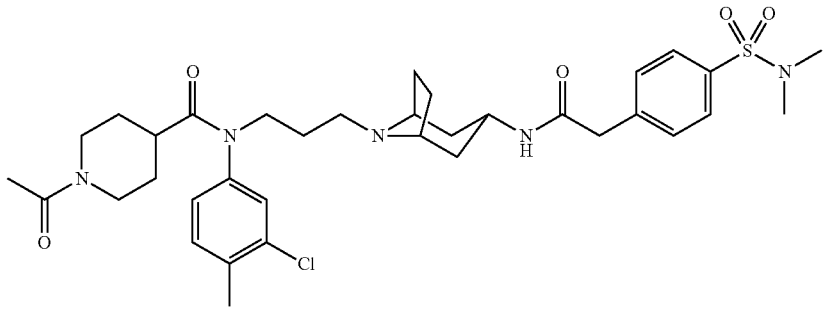 [SMILES: CC(=O)N1CCC(C(=O)N(CCCN2C3CCC2CC(NC(=O)Cc2ccc(S(=O)(=O)N(C)C)cc2)C3)c2ccc(C)c(Cl)c2)CC1]

Preparation of the Starting Materials

The 4-chlorosulfonylphenylacetic acid ethyl ester was prepared according to the step (1) of example 9.

Step (2): preparation of 4-N,N-dimethylaminosulfonylphenylacetic acid ethyl ester The step (2) had a similar procedure as the step (2) of example 9, except using dimethylamine instead of pyrrolidine in the step (2) of example 9.

Step (3): preparation of 4-N,N-dimethylaminosulfonylphenylacetic acid

The step (3) had a similar procedure as the step (3) of example 9, except using 4-N,N-dimethylaminosulfonylphenylacetic acid ethyl ester instead of 4-(1-pyrrolidine)sulfonylphenylacetic acid ethyl ester in the step (3) of example 9. The 4-N,N-dimethylaminosulfonylphenylacetic acid was obtained as a white needlelike crystal (450 mg, yield: 53%).

$^1$HNMR (CDCl$_3$, 300 MHz) δ: 7.75 (d, 2H, J=8.4 Hz), 7.46 (d, 2H, J=8.4 Hz), 3.74 (s, 2H), 2.71 (s, 6H).

The object compound was obtained following the method in example 1 except using the 4-N,N-dimethylaminosulfonylphenylacetic acid instead of phenylacetic acid in Example 1 in step 7:

A white foam-like solid (49 mg, yield: 45%)

$^1$HNMR (CDCl$_3$, 300 MHz) δ: 7.72 (d, 2H, J=7.8 Hz), 7.44 (d, 2H, J=7.8 Hz), 7.30 (d, 1H, J=7.8 Hz), 7.19 (d, 1H, J=1.8 Hz), 7.03 (dd, 1H, J=1.8 Hz, 7.8 Hz), 6.18 (br, 1H), 4.54-4.50 (m, 1H), 4.27-4.16 (m, 1H), 3.78-3.66 (m, 3H), 3.55 (s, 2H), 3.48 (br, 2H), 2.88-2.79 (m, 1H), 2.71 (s, 6H), 2.59-2.55 (m, 2H), 2.42 (s, 3H), 2.38-2.33 (m, 2H), 2.04 (s, 3H), 1.99-1.96 (m, 3H), 1.86-1.79 (m, 8H), 1.66-1.61 (m, 3H);

EI (LR-MS): 685 (M)$^+$, 139 (100);

EI (HR-MS): calc for. 685.3065. found 685.3077.

Example 11

Compound 7k:

1-acetyl-N-(3-chloro-4-methylphenyl)-N-(3-(3-exo-(2-(4-(methyl sulphonyl)phenyl)acetamido)-8-azabicyclo[3.2.1]oct-8-yl)propyl)-4-piperidinylcarboxamide

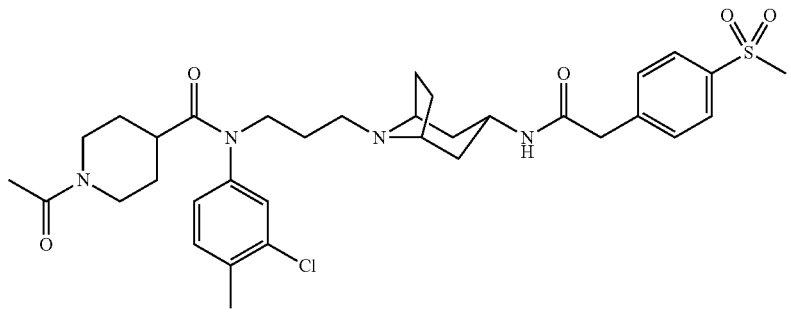 [SMILES: CC(=O)N1CCC(C(=O)N(CCCN2C3CCC2CC(NC(=O)Cc2ccc(S(C)(=O)=O)cc2)C3)c2ccc(C)c(Cl)c2)CC1]

2-(4-(methylsulphonyl)phenyl)acetic acid (commercially available from ACROS Reagent Company, CAS: 90536-66-6) was used instead of the phenylacetic acid in example 1 in step 7.

A white foam-like solid (41 mg, yield: 39%)

$^1$HNMR (CDCl$_3$, 300 MHz) δ: 7.89 (d, 2H, J=8.1 Hz), 7.57 (d, 2H, J=8.1 Hz), 7.47 (d, 2H, J=8.1 Hz), 7.19 (s, 1H), 7.00 (d, 1H, J=8.1 Hz), 5.89 (br, 1H), 4.53-4.49 (m, 1H), 4.19-4.13 (m, 1H), 3.78-3.74 (m, 1H), 3.70-3.65 (m, 2H), 3.57 (s, 2H), 3.33 (br, 2H), 3.05 (s, 3H), 2.88-2.80 (m, 1H), 2.42 (s, 3H), 2.37-2.31 (m, 2H), 2.04 (s, 3H), 1.99-1.96 (m, 6H), 1.77-1.60 (m, 10H);

EI (LR-MS): 656 (M)$^+$, 335 (100);

EI (HR-MS): calc for. 656.2799. found 656.2810.

Example 12

Compound 7l:

1-acetyl-N-(3-chloro-4-methylphenyl)-N-(3-(3-exo-(2-(4-(morpholino sulfonyl)phenyl)acetamido)-8-azabicyclo[3.2.1]oct-8-yl)propyl)-4-piperidinylcarboxamide

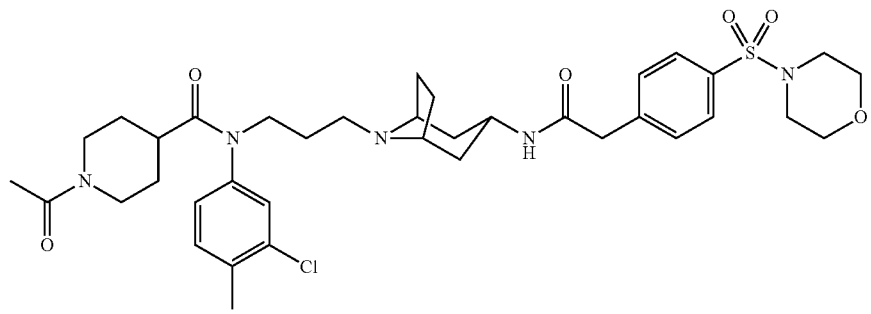 [SMILES: CC(=O)N1CCC(C(=O)N(CCCN2C3CCC2CC(NC(=O)Cc2ccc(S(=O)(=O)N4CCOCC4)cc2)C3)c2ccc(C)c(Cl)c2)CC1]

Preparation of the Starting Materials 4-chlorosulfonylphenylacetic acid ethyl ester was prepared according to the step (1) in example 9.

Step (2): preparation of 4-(1-morpholinyl)sulfonylphenylacetic acid ethyl ester

The step (2) had a similar procedure as the step (2) of example 9, except using morpholine instead of pyrrolidine in the step (2) of example 9.

Step (3): preparation of 4-(1-morpholinyl)sulfonylphenylacetic acid

The step (3) had a similar procedure as the step (3) of example 9, except using 4-(1-morpholinyl)sulfonylphenylacetic acid ethyl ester instead of 4-(1-pyrrolidine) sulfonylphenylacetic acid ethyl ester in the step (3) of example 9. The 4-(1-morpholinyl)sulfonylphenylacetic acid was obtained as a white needlelike crystal (207 mg, yield: 70%).

$^1$HNMR (CDCl$_3$, 300 MHz) δ: 7.72 (d, 2H, J=8.1 Hz), 7.48 (d, 2H, J=8.1 Hz), 3.74 (s, 2H), 3.75 (t, 4H, J=4.8 Hz), 3.00 (t, 4H, J=4.8 Hz).

The object compound was obtained following the method in example 1 except using 4-(1-morpholinyl)sulfonylphenylacetic acid instead of phenylacetic acid in Example 1 in step 7:

A white foam-like solid (57 mg, yield: 49%)

$^1$HNMR (CDCl$_3$, 300 MHz) δ: 7.70 (d, 2H, J=8.1 Hz), 7.46 (d, 2H, J=8.1 Hz), 7.29 (d, 1H, J=7.8 Hz), 7.18 (d, 1H, J=1.8 Hz), 7.02 (dd, 1H, J=1.8 Hz, 7.8 Hz), 6.02 (br, 1H), 4.54-4.49 (m, 1H), 4.21-4.15 (m, 1H), 3.79-3.77 (m, 4H), 3.75-3.72 (m, 4H), 3.69-3.66 (m, 2H), 3.55 (s, 2H), 3.42 (br, 2H), 3.01-2.98 (m, 4H), 2.88-2.79 (m, 1H), 2.54-2.49 (m, 2H), 2.42 (s, 3H), 2.38-2.30 (m, 3H), 2.04 (s, 3H), 2.01-1.99 (m, 2H), 1.83-1.76 (m, 8H), 1.64-1.59 (m, 3H);

EI (LR-MS): 727 (M)$^+$, 165 (100);
EI (HR-MS): calc for. 727.3170. found 727.3176.

Example 13

Compound 7m:

1-acetyl-N-(3-(3-exo-(2-(4-(N-tert-butylsulphonyl)phenyl)acetamido)-8-azabicyclo[3.2.1]oct-8-yl)propyl)-N-(3-chloro-4-methylphenyl)-4-piperidinylcarboxamide Preparation of the Starting Materials 4-chlorosulfonylphenylacetic acid ethyl ester was prepared according to the step (1) in example 9.

Step (2): preparation of 4-tert-butylaminosulfonylphenylacetic acid ethyl ester

The step (2) had a similar procedure as the step (2) of example 9, except using tert-butylamine instead of pyrrolidine in the step (2) of example 9.

Step (3): preparation of 4-tert-butylaminosulfonylphenylacetic acid

The step (3) had a similar procedure as the step (3) of example 9, except using 4-tert-butylaminosulfonylphenylacetic acid ethyl ester instead of 4-(1-pyrrolidine) sulfonylphenylacetic acid ethyl ester in the step (3) of example 9. The 4-tert-butylaminosulfonyl phenylacetic acid was obtained as a white crystal (180 mg, yield: 21%).

$^1$HNMR (CDCl$_3$, 300 MHz) δ: 7.85 (d, 2H, J=8.4 Hz), 7.41 (d, 2H, J=8.4 Hz), 5.04 (s, 1H), 3.72 (s, 2H), 1.21 (s, 9H).

The object compound was obtained following the method in example 1, except using 4-tert-butylaminosulfonylphenylacetic acid instead of phenylacetic acid in example 1:

A white foam-like solid (78 mg, yield: 78%)

$^1$HNMR (CDCl$_3$, 300 MHz) δ: 7.81 (d, 2H, J=6.9 Hz), 7.35 (d, 2H, J=6.9 Hz), 7.27-7.19 (m, 2H), 7.02-6.99 (m, 1H), 6.02 (br, 1H), 5.00 (br, 1H), 4.53-4.48 (m, 1H), 4.13 (br, 1H), 3.77-3.66 (m, 3H), 3.52 (s, 2H), 3.33 (br, 2H), 2.77-2.65 (m, 4H), 2.40 (s, 3H), 2.34-2.28 (m, 2H), 2.03 (s, 3H), 1.98-1.94 (m, 2H), 1.75-1.60 (m, 11H), 1.21 (s, 9H);

EI (LR-MS): 713 (M)$^+$, 191 (100);
EI (HR-MS): calc for. 713.3378. found 713.3384.

Example 14

Compound 7n:

1-acetyl-N-(3-chloro-4-methylphenyl)-N-(3-(3-exo-(2-(1-naphthyl)acetamido)-8-azabicyclo[3.2.1]oct-8-yl)propyl)-4-piperidinylcarboxamide

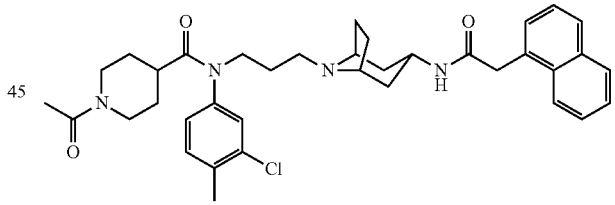

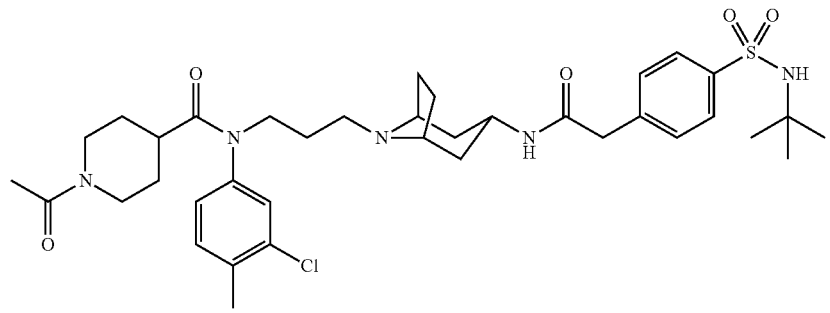 [SMILES: CC(=O)N1CCC(C(=O)N(CCCN2C3CCC2CC(NC(=O)Cc2ccc(S(=O)(=O)NC(C)(C)C)cc2)C3)c2ccc(C)c(Cl)c2)CC1]

2-(1-naphthyl)acetic acid (commercially available from ACROS Reagent Company, CAS: 86-87-3) was used instead of phenylacetic acid in Example 1 in step 7.

A white foam-like solid (92 mg, yield: 67%)

¹HNMR (CD₃OD, 300 MHz) δ: 8.04-7.98 (m, 1H), 7.88-7.77 (m, 2H), 7.50-7.40 (m, 6H), 7.21-7.15 (m, 1H), 4.45-4.41 (m, 1H), 4.12-4.05 (m, 1H), 3.95 (s, 2H), 3.87-3.80 (m, 1H), 3.74-3.69 (m, 2H), 3.39-3.34 (m, 2H), 2.90-2.82 (m, 1H), 2.56-2.48 (m, 4H), 2.42 (s, 3H), 2.05 (s, 3H), 1.75-1.63 (m, 14H);

EI (LR-MS): 628 (M)⁺, 235 (100);

EI (HR-MS): calc for. 628.3180. found 628.3154.

Example 15

Compound 7o:

1-acetyl-N-(3-chloro-4-methylphenyl)-N-(3-(3-exo-(2-(2-naphthyl)acetamido)-8-azabicyclo[3.2.1]-oct-8-yl)propyl)-4-piperidinylcarboxamide

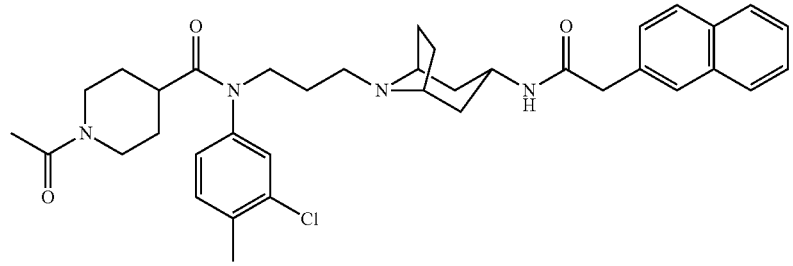 [SMILES: CC(=O)N1CCC(C(=O)N(CCCN2C3CCC2CC(NC(=O)Cc2ccc4ccccc4c2)C3)c2ccc(C)c(Cl)c2)CC1]

2-(2-naphthyl)acetic acid (commercially available from ACROS Reagent Company, CAS: 581-96-4) was used instead of phenylacetic acid in Example 1 in step 7.

A white foam-like solid (65 mg, yield: 47%) ¹HNMR (CD₃OD, 300 MHz) δ: 8.38-8.36 (m, 1H), 7.99-7.87 (m, 4H), 7.59-7.45 (m, 4H), 7.29-7.23 (m, 1H), 4.46-4.41 (m, 2H), 3.89-3.77 (m, 5H), 2.98-2.86 (m, 3H), 2.53-2.49 (m, 1H), 2.43 (s, 3H), 2.27-2.23 (m, 2H), 2.13-2.10 (m, 6H), 2.05 (s, 3H), 1.95-1.90 (m, 4H), 1.74-1.57 (m, 6H);

EI (LR-MS): 628 (M), 235 (100).

Example 16

Compound 7p:

1-acetyl-N-(3-chloro-4-methylphenyl)-N-(3-(3-exo-(2-hydroxyl-2-phenylacetamido)-8-azabicyclo[3.2.1]oct-8-yl)propyl)-4-piperidinylcarboxamide

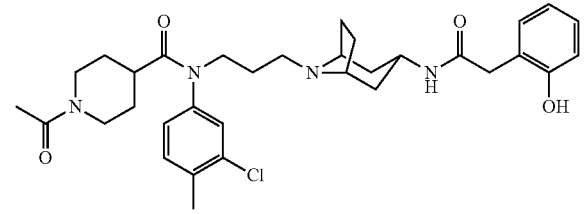 [SMILES: CC(=O)N1CCC(C(=O)N(CCCN2C3CCC2CC(NC(=O)Cc2ccccc2O)C3)c2ccc(C)c(Cl)c2)CC1]

2-hydroxyl-2-phenylacetic acid (commercially available from ACROS Reagent Company, CAS: 90-64-2) was used instead of phenylacetic acid in Example 1 in step 7.

A white foam-like solid (43 mg, yield: 36%) ¹HNMR (CDCl₃, 300 MHz) δ: 7.36-7.31 (m, 5H), 7.19 (s, 1H), 7.02 (d, 1H, J=9.0 Hz), 6.57-6.54 (m, 1H), 5.00 (s, 1H), 4.52-4.47 (m, 1H), 4.19-4.11 (m, 1H), 3.76-3.72 (m, 1H), 3.67-3.62 (m, 2H), 3.34 (br, 2H), 2.87-2.78 (m, 1H), 2.50-2.45 (m, 3H), 2.41 (s, 3H), 2.34-2.29 (m, 2H), 2.03 (s, 3H), 1.99-1.86 (m, 2H), 1.80-1.75 (m, 8H), 1.62-1.58 (m, 3H);

EI (LR-MS): 594 (M)⁺, 273 (100);

EI (HR-MS): calc for. 594.2973. found 594.2986.

Example 17

Compound 7q:

N-(3-(3-exo-(2-(3-indolyl)acetamido)-8-azabicyclo[3.2.1]oct-8-yl)propyl)-1-acetyl-N-(3-chloro-4-methylphenyl)-4-piperidinylcarboxamide

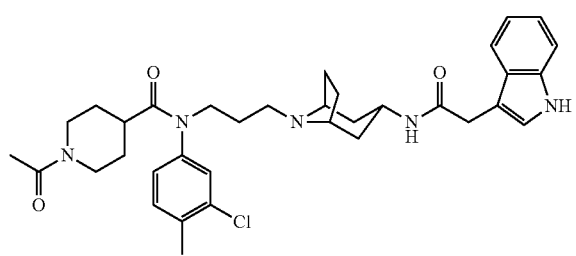 [SMILES: CC(=O)N1CCC(C(=O)N(CCCN2C3CCC2CC(NC(=O)Cc2c[nH]c4ccccc24)C3)c2ccc(C)c(Cl)c2)CC1]

2-(3-indolyl)acetic acid (commercially available from ACROS Reagent Company, CAS: 87-51-4) was used instead of phenylacetic acid in Example 1 in step 7.

A white foam-like solid (32 mg, yield: 32%)

¹HNMR (CD₃OD, 300 MHz) δ: 7.54-7.51 (m, 1H), 7.47-7.43 (m, 2H), 7.35-7.32 (m, 1H), 7.24-7.21 (m, 1H), 7.16 (s, 1H), 7.12-7.07 (m, 1H), 7.02-6.97 (m, 1H), 4.45-4.41 (m, 1H), 4.20 (br, 1H), 3.86-3.73 (m, 5H), 3.63 (s, 2H), 2.92-2.84

(m, 3H), 2.52-2.48 (m, 1H), 2.42 (s, 3H), 2.20-2.16 (m, 2H), 2.05 (s, 3H), 2.01-1.96 (m, 4H), 1.89-1.81 (m, 5H), 1.73-1.63 (m, 4H);

EI (LR-MS): 617 (M)+, 296 (100);
EI (HR-MS): calc for. 617.3133. found 617.3123.

Example 18

Compound 7r: 1-acetyl-N-(3-chloro-4-methylphenyl)-N-(3-(3-exo-(2-(3,4,5-trimethoxylphenyl)acetamido)-8-azabicyclo[3.2.1]oct-8-yl)propyl)-4-piperidinylcarboxamide

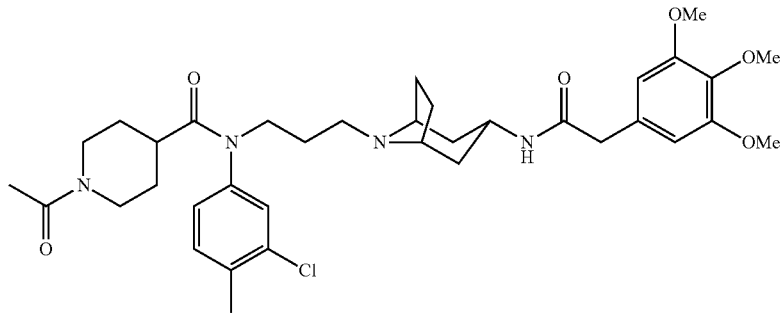 [SMILES: COc1cc(CC(=O)NC2CC3CCC(C2)N3CCCN(C(=O)C2CCN(C(C)=O)CC2)c2ccc(C)c(Cl)c2)cc(OC)c1OC]

2-(3,4,5-trimethoxylphenyl)acetic acid (commercially available from ACROS Reagent Company, CAS: 951-82-6) was used instead of phenylacetic acid in Example 1 in step 7.

A white foam-like solid (42 mg, yield: 39%)

$^1$HNMR (CDCl$_3$, 300 MHz) δ: 7.29 (d, 1H, J=7.8 Hz), 7.18 (d, 1H, J=1.5 Hz), 7.01 (dd, 1H, J=1.5 Hz, 7.8 Hz), 6.43 (s, 2H), 5.71 (m, 1H), 4.52-4.48 (m, 1H), 4.18-4.13 (m, 1H), 3.84 (s, 9H), 3.78-3.73 (m, 1H), 3.68-3.63 (m, 2H), 3.43 (s, 2H), 3.34 (br, 2H), 2.87-2.79 (m, 1H), 2.41 (s, 3H), 2.37-2.30 (m, 3H), 2.04 (s, 3H), 1.99-1.95 (m, 2H), 1.83-1.72 (m, 8H), 1.67-1.58 (m, 5H);

EI (LR-MS): 668 (M), 347 (100);
EI (HR-MS): calc for. 668.3341. found 668.3337.

Example 19

Compound 7s: 1-acetyl-N-(3-chloro-4-methylphenyl)-N-(3-(3-exo-(2-(4-nitro-1-naphthyl)acetamido)-8-azabicyclo[3.2.1]oct-8-yl)propyl)-4-piperidinylcarboxamide

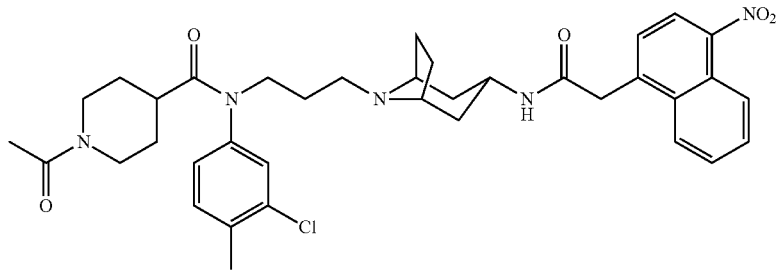 [SMILES: CC(=O)N1CCC(C(=O)N(CCCN2C3CCC2CC(NC(=O)Cc2ccc([N+](=O)[O-])c4ccccc24)C3)c2ccc(C)c(Cl)c2)CC1]

2-(4-nitro-1-naphthyl)acetic acid (commercially available from ACROS Reagent Company, CAS: 89278-25-1) was used instead of phenylacetic acid in Example 1 in step 7.

A white foam-like solid (82 mg, yield: 61%)

$^1$HNMR (CD$_3$OD, 300 MHz) δ: 8.44-8.14 (m, 2H), 7.78-7.56 (m, 3H), 7.48-7.43 (m, 3H), 7.25-7.23 (m, 1H), 4.46-4.42 (m, 1H), 4.21-4.17 (m, 1H), 4.11 (s, 2H), 3.89-3.77 (m, 6H), 2.93-2.85 (m, 4H), 2.42 (s, 3H), 2.20-2.17 (m, 3H), 2.05 (s, 3H), 2.00-1.90 (m, 8H), 1.73-1.69 (m, 3H);

EI (LR-MS): 673 (M)+, 82 (100);
EI (HR-MS): calc for. 673.3031. found 673.3037.

Example 20

Compound 7t:

1-acetyl-N-(3-chloro-4-methylphenyl)-N-(3-(3-exo-nicotinamido-8-azabicyclo[3.2.1]oct-8-yl)propyl)-4-piperidinylcarboxamide

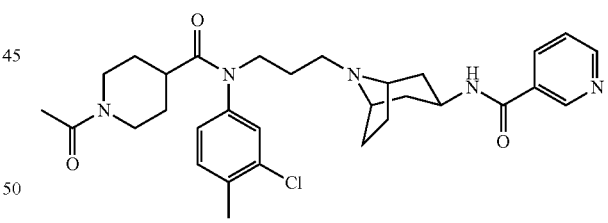

Nicotinic acid (commercially available from Sinopharm Chemical Reagent Co. Ltd, CAS: 59-67-6) was used instead of phenylacetic acid in Example 1 in step 7.

A yellowish foam-like product (80 mg, yield: 70%).

¹HNMR (CDCl₃, 300 MHz) δ: 8.98 (d, 1H, J=1.5 Hz), 8.69-8.67 (m, 1H), 8.11-8.09 (m, 1H), 7.38-7.29 (m, 2H), 7.22 (m, 1H), 7.06-7.03 (m, 1H), 6.76-6.65 (m, 1H), 5.30 (s, 1H), 4.53-4.49 (m, 1H), 4.44-4.36 (m, 1H), 3.78-3.68 (m, 3H), 3.51-3.41 (m, 2H), 2.88-2.80 (t, 1H, J=11.4 Hz), 2.55-2.51 (m, 2H), 2.44 (s, 3H), 2.44-2.30 (m, 2H), 2.04 (s, 3H), 1.92-1.57 (m, 13H);

EI (LR-MS): 565 (M)⁺, 84 (100).

Example 21

Compound 7u:

1-acetyl-N-(3-chloro-4-methylphenyl)-N-(3-(3-exo-p-trifluoromethyl benzoylamido-8-azabicyclo[3.2.1]oct-8-yl)propyl)-4-piperidinylcarboxamide

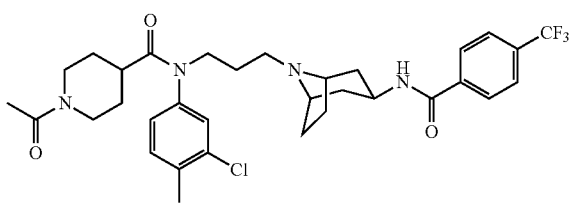 [SMILES: CC(=O)N1CCC(C(=O)N(CCCN2C3CCC2CC(NC(=O)c2ccc(C(F)(F)F)cc2)C3)c2ccc(C)c(Cl)c2)CC1]

p-trifluoromethylbenzoic acid (commercially available from Sinopharm Chemical Reagent Co. Ltd, CAS: 455-24-3) was used instead of phenylacetic acid in Example 1 in step 7.

A yellowish foam-like product (21 mg, yield: 22%).

¹HNMR (CDCl₃, 300 MHz) δ: 8.01-7.93 (m, 2H), 7.68-7.65 (d, 2H, J=8.4 Hz), 7.38-7.35 (d, 1H, J=8.4 Hz), 7.24-7.21 (m, 1H), 7.16-7.11 (m, 1H), 4.57-4.44 (m, 1H), 4.10-4.08 (m, 1H), 3.83-3.70 (m, 3H), 3.20-3.06 (m, 2H), 2.88-2.81 (m, 1H), 2.41 (s, 3H), 2.47-2.13 (m, 8H), 1.99 (s, 3H), 2.04-1.93 (m, 2H), 1.73-1.59 (m, 9H);

EI (LR-MS): 632 (M)⁺, 82 (100).

Example 22

Compound 7v: 1-acetyl-N-(3-chloro-4-methylphenyl)-N-(3-(3-exo-(3-(3-pyridyl)propionamido)-8-azabicyclo[3.2.1]oct-8-yl)propyl)-4-piperidinylcarboxamide

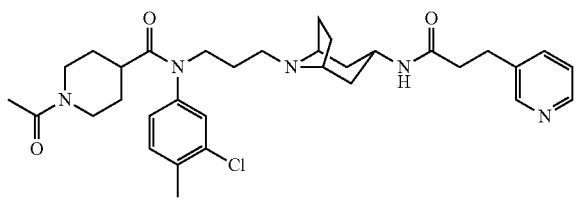 [SMILES: CC(=O)N1CCC(C(=O)N(CCCN2C3CCC2CC(NC(=O)CCc2cccnc2)C3)c2ccc(C)c(Cl)c2)CC1]

3-(3-pyridyl) propionic acid (commercially available from Alfa Aesar Reagent Company, CAS: 3724-19-4) was used instead of phenylacetic acid in Example 1 in step 7.

A white foam-like solid (57 mg, yield: 74%).

¹HNMR (CD₃OD, 300 MHz) δ: 8.38-8.35 (m, 2H), 7.71-7.68 (m, 1H), 7.43-7.17 (m, 4H), 4.45-4.41 (m, 1H), 4.09-4.01 (m, 1H), 3.87-3.83 (m, 1H), 3.73-3.69 (m, 2H), 3.51 (br, 2H), 2.96-2.91 (m, 4H), 2.66-2.61 (m, 3H), 2.50-2.45 (m, 4H), 2.41 (s, 3H), 2.05 (s, 3H), 1.85-1.54 (m, 12H);

EI (LR-MS): 593 (M)⁺, 272 (100).

Example 23

Compound 7w:

1-acetyl-N-(3-chloro-4-methylphenyl)-N-(3-(3-exo-(2-(2-naphthoxy)acetamido)-8-azabicyclo[3.2.1]oct-8-yl)propyl)-4-piperidinylcarboxamide 2-(2-naphthoxy)acetic acid (commercially available from ACROS Reagent Company, CAS: 120-23-0) was used instead of phenylacetic acid in Example 1 in step 7.

A white foam-like solid (98 mg, yield: 76%).

¹HNMR (CD₃OD, 300 MHz) δ: 7.81-7.74 (m, 3H), 7.48-7.41 (m, 3H), 7.37-7.33 (m, 1H), 7.28-7.23 (m, 3H), 4.64 (s, 2H), 4.46-4.41 (m, 1H), 4.35-4.30 (m, 1H), 3.88-3.82 (m, 3H), 3.79-3.75 (m, 2H), 2.98-2.83 (m, 4H), 2.42 (s, 3H), 2.24-2.18 (m, 3H), 2.04 (s, 3H), 2.00-1.90 (m, 8H), 1.73-1.68 (m, 4H);

EI (LR-MS): 644 (M)⁺, 323 (100);

EI (HR-MS): calc for. 644.3129. found 644.3137.

Example 24

Compound 7x: 1-acetyl-N-(3-chloro-4-methylphenyl)-N-(3-(3-exo-(2-p-chlorophenoxy)acetamido-8-azabicyclo[3.2.1]oct-8-yl)propyl)-4-piperidinylcarboxamide

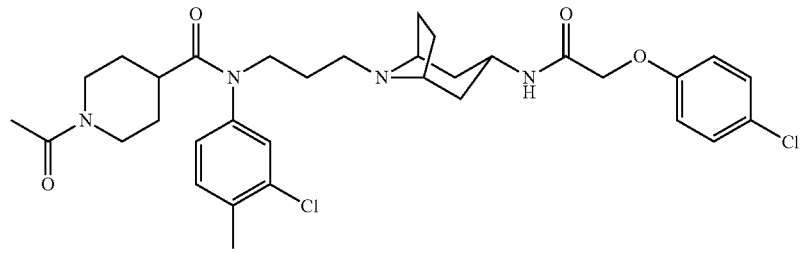 [SMILES: CC(=O)N1CCC(C(=O)N(CCCN2C3CCC2CC(NC(=O)COc2ccc(Cl)cc2)C3)c2ccc(C)c(Cl)c2)CC1]

2-p-chlorophenoxyacetic acid (commercially available from ACROS Reagent Company, CAS: 122-88-3) was used instead of phenylacetic acid in Example 1 in step 7.
A yellowish foam-like solid (93 mg, yield: 74%)
$^1$HNMR (CD$_3$OD, 300 MHz) δ: 7.45-7.43 (m, 2H), 7.27 (d, 2H, J=8.1 Hz), 7.21-7.18 (m, 1H), 6.96 (d, 2H, J=8.1 Hz), 4.46 (s, 2H), 4.26-4.14 (m, 1H), 3.88-3.83 (m, 1H), 3.74-3.70 (m, 2H), 3.39 (br, 2H), 2.92-2.82 (m, 1H), 2.57-2.47 (m, 3H), 2.42 (s, 3H), 2.38-2.33 (m, 1H), 2.05 (s, 3H), 2.04-2.00 (m, 1H), 1.79-1.54 (m, 14H);
EI (LR-MS): 628 (M)$^+$, 307 (100);
EI (HR-MS): calc for. 628.2583. found 628.2573.

Example 25

Compound 7y: 1-acetyl-N-(3-chloro-4-methylphenyl)-N-(3-(3-exo-(2-(2,4-dichlorophenoxy)acetamido)-8-azabicyclo[3.2.1]oct-8-yl)propyl)-4-piperidinylcarboxamide

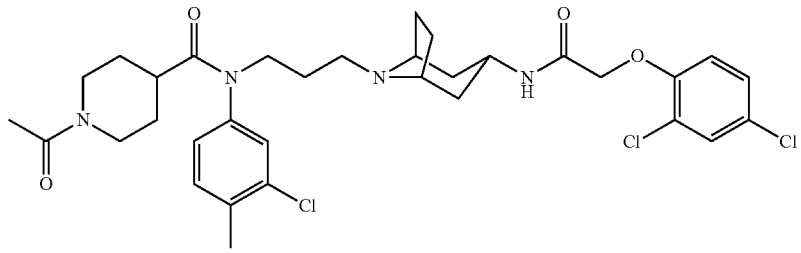 [SMILES: CC(=O)N1CCC(C(=O)N(CCCN2C3CCC2CC(NC(=O)COc2ccc(Cl)cc2Cl)C3)c2ccc(C)c(Cl)c2)CC1]

2-(2,4-dichlorophenoxy)acetic acid (commercially available from ACROS Reagent Company, CAS: 94-75-7) was used instead of phenylacetic acid in Example 1 in step 7.
A white foam-like solid (75 mg, yield: 57%)
$^1$HNMR (CD$_3$OD, 300 MHz) δ: 7.46-7.43 (m, 3H), 7.29-7.25 (m, 1H), 7.21-7.18 (m, 1H), 7.04-7.00 (m, 1H), 4.56 (s, 2H), 4.46-4.41 (m, 1H), 4.25-4.13 (m, 1H), 3.88-3.83 (m, 1H), 3.75-3.70 (m, 2H), 3.40 (br, 2H), 2.92-2.82 (m, 1H), 2.56-2.49 (m, 3H), 2.42 (s, 3H), 2.39-2.34 (m, 1H), 2.05 (s, 3H), 2.03-2.00 (m, 1H), 1.83-1.77 (m, 6H), 1.72-1.58 (m, 7H);
EI (LR-MS): 662 (M)$^+$, 341 (100);
EI (HR-MS): calc for. 662.2193. found 662.2195.

Example 26

Compound 7z: 1-acetyl-N-(3-chloro-4-methylphenyl)-N-(3-(3-exo-(2-(4-(N-methylsulphonyl)phenyl)acetamido)-8-azabicyclo[3.2.1]oct-8-yl)propyl)-4-piperidinylcarboxamide

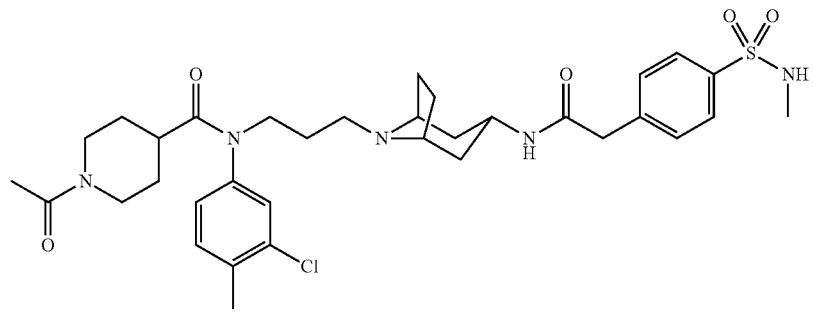 [SMILES: CNS(=O)(=O)c1ccc(CC(=O)NC2CC3CCC(C2)N3CCCN(C(=O)C2CCN(C(C)=O)CC2)c2ccc(C)c(Cl)c2)cc1]

Preparation of the Starting Materials 4-chlorosulfonylphenylacetic acid ethyl ester was prepared according to the step (1) of example 9.

Step (2): preparation of 4-N-methylaminosulfonylphenylacetic acid ethyl ester The step (2) had a similar procedure as the step (2) of example 9, except using methylamine instead of pyrrolidine in the step (2) of example 9.

Step (3): preparation of 4-N-methylaminosulfonylphenylacetic acid

The step (3) had a similar procedure as the step (3) of example 9, except using 4-N-methylaminosulfonylphenylacetic acid ethyl ester instead of 4-(1-pyrrolidine)sulfonylphenylacetic acid ethyl ester in the step (3) of example 9. The 4-N-methylaminosulfonylphenylacetic acid was obtained as a white needlelike crystal (686 mg, yield: 51%).

The object compound was obtained following the method in example 1 except using 4-N-methylaminosulfonylphenylacetic acid instead of phenylacetic acid in Example 1 in step 7:

A white foam-like solid (132 mg, yield: 18%)

$^1$HNMR (CD$_3$OD, 300 MHz) δ: 7.77 (d, 2H, J=8.7 Hz), 7.51-7.45 (m, 4H), 7.28 (dd, 1H, J=2.1 Hz, 8.1 Hz), 4.45-4.41 (m, 1H), 4.25-4.18 (m, 1H), 4.01 (br, 2H), 3.89-3.77 (m, 3H), 3.61 (s, 2H), 3.07 (br, 2H), 2.93-2.85 (m, 1H), 2.50 (s, 3H), 2.43 (s, 3H), 2.39-2.36 (m, 1H), 2.29-2.25 (m, 2H), 2.12-2.10 (m, 3H), 2.05 (s, 3H), 2.00-1.95 (m, 5H), 1.75-1.70 (m, 3H), 1.64-1.54 (m, 2H).

Example 27

Compound 8: 1-acetyl-N-(3-chloro-4-methylphenyl)-N-(3-(3-exo-benzyloxymethanamido-8-azabicyclo[3.2.1]oct-8-yl)propyl)-4-piperidinylcarboxamide

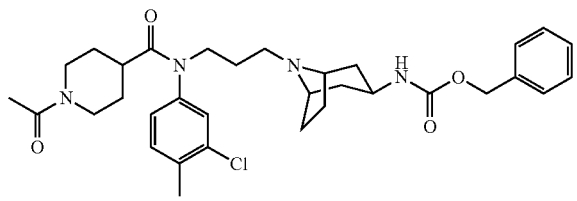 [SMILES: CC(=O)N1CCC(C(=O)N(CCCN2C3CCC2CC(NC(=O)OCc2ccccc2)C3)c2ccc(C)c(Cl)c2)CC1]

Step 1: 1-acetyl-N-(3-chloro-4-methylphenyl)-N-(3-(3-exo-benzyloxymethanamido-8-azabicyclo[3.2.1]oct-8-yl)propyl)-4-piperidinylcarboxamide Triethylamine (0.045 mL, 0.32 mmol) was added into a solution of the compound 6 (75 mg, 0.16 mmol) prepared in example 1 in dichloromethane (4 mL). After cooling the mixture to 0° C., benzyloxyformyl chloride (0.03 mL, 0.19 mmol) was dropped therein. Then the mixture was stirred at the same temperature for 1 hour, diluted with dichloromethane, and washed with saline. The organic phase was dried with sodium sulfate and concentrated under reduced pressure. The concentrate was separated through column chromatography (dichloromethane/methanol=30/1 to 5/1, v/v) to obtain the product as a yellowish foam-like solid (27 mg, yield: 28%).

$^1$HNMR (CDCl$_3$, 300 MHz) δ: 7.33-7.23 (m, 8H), 5.38-5.35 (m, 1H), 5.07 (s, 2H), 4.55-4.50 (d, 1H, J=12.9 Hz), 4.02-3.97 (m, 1H), 3.73-3.60 (m, 5H), 2.87-2.78 (m, 3H), 2.41 (s, 3H), 2.41-2.22 (m, 4H), 2.17-2.12 (m, 2H), 2.04 (s, 3H), 2.08-1.90 (m, 7H), 1.74-1.61 (m, 3H);

[EI (LR-MS): 594 (M)$^+$, 108 (100);

EI (HR-MS): calc for. 594.2973. found 594.2966.

Example 28

Compound 9a:

1-acetyl-N-(3-chloro-4-methylphenyl)-N-(3-(3-exo-(methylsulfonyl amido)-8-azabicyclo[3.2.1]oct-8-yl)propyl)-4-piperidinylcarboxamide

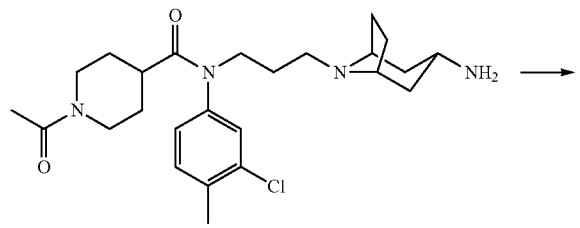

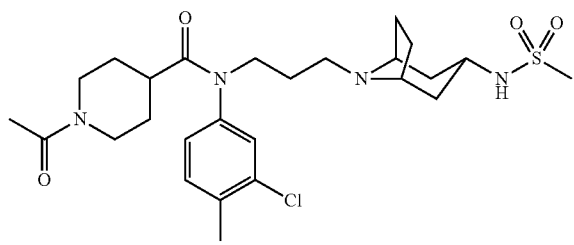

Step 1: 1-acetyl-N-(3-chloro-4-methylphenyl)-N-(3-(3-exo-(methylsulfonylamido)-8-azabicyclo[3.2.1]oct-8-yl)propyl)-4-piperidinylcarboxamide Triethylamine (46 μL, 0.36 mmol) was added into a solution of the compound 6 (103 mg, 0.22 mmol) prepared in example 1 in dichloromethane (4 mL). After cooling the mixture to 0° C., methane sulfonyl chloride (20 μL, 0.27 mmol) was dropped therein. Then the mixture was stirred at the same temperature for 1 hour, diluted with dichloromethane, and washed with saline. The organic phase was dried with sodium sulfate and concentrated under reduced pressure. The concentrate was separated through column chromatography (dichloromethane/methanol=30/1 to 5/1, v/v) to obtain the product as a white foam-like solid (86 mg, yield: 73%).

$^1$HNMR (CDCl$_3$, 300 MHz) δ: 7.54-7.53 (m, 1H), 7.47-7.43 (m, 2H), 5.61-5.60 (m, 1H), 4.40-4.36 (m, 1H), 4.00-3.97 (m, 2H), 3.85-3.73 (m, 4H), 3.08-3.03 (m, 2H), 2.94 (s, 3H), 2.51-2.48 (m, 1H), 2.39 (s, 3H), 2.33-2.27 (m, 5H), 2.13-2.09 (m, 2H), 1.98 (s, 3H), 1.94-1.92 (m, 2H), 1.83-1.80 (m, 1H), 1.70-1.64 (m, 3H), 1.57-1.50 (m, 3H);

EI (LR-MS): 538 (M)$^+$, 217 (100);

EI (HR-MS): calc for. 538.2381. found 538.2377.

The following examples 29-33 have similar reaction conditions as those in example 28, except using a derivative from phenylmethylsulfonyl chloride, phenylethylsulfonyl chloride and thienylsulfonyl chloride instead of methane sulfonyl chloride in the last step.

Example 29

Compound 9b: 1-acetyl-N-(3-chloro-4-methylphenyl)-N-(3-(3-exo-p-tolylsulfonamido-8-azabicyclo[3.2.1]oct-8-yl)propyl)-4-piperidinylcarboxamide 4-tolylsulfonyl chloride was used instead of methane sulfonyl chloride in example 28 in step 1.

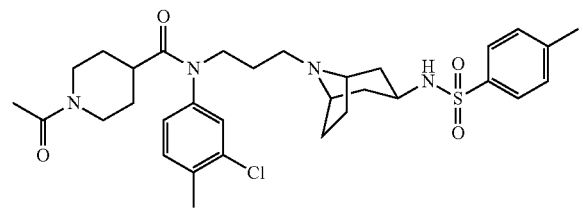 [SMILES: CC(=O)N1CCC(C(=O)N(CCCN2C3CCC2CC(NS(=O)(=O)c2ccc(C)cc2)C3)c2ccc(C)c(Cl)c2)CC1]

A yellowish foam-like product (27 mg, yield: 32%)

$^1$HNMR (CDCl$_3$, 300 MHz) δ: 7.76-7.73 (d, 2H, J=8.1 Hz), 7.27-7.25 (d, 3H, J=6.6 Hz), 7.19 (s, 1H), 7.11-7.08 (d, 1H, J=7.5 Hz), 4.51-4.47 (d, 1H), 3.74-3.42 (m, 7H), 2.83-2.75 (m, 1H), 2.66-2.63 (m, 1H), 2.41 (s, 3H), 2.39 (s, 3H), 2.33-2.28 (m, 2H), 2.02 (s, 3H), 2.02-1.93 (m, 4H), 1.85 (m, 2H), 1.66 (m, 9H);

EI (LR-MS): 614 (M)$^+$, 165 (100);

EI (HR-MS): calc for. 614.2694. found 614.2713.

Example 30

Compound 9c: 1-acetyl-N-(3-chloro-4-methylphenyl)-N-(3-(3-exo-(4-nitrophenylsulfonylamido)-8-azabicyclo[3.2.1]oct-8-yl)propyl)-4-piperidinylcarboxamide

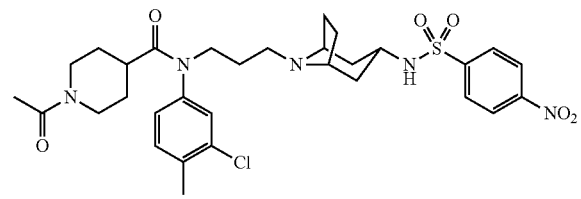 [SMILES: CC(=O)N1CCC(C(=O)N(CCCN2C3CCC2CC(NS(=O)(=O)c2ccc([N+](=O)[O-])cc2)C3)c2ccc(C)c(Cl)c2)CC1]

4-nitrophenylsulfonic chloride (commercially available from ACROS Reagent Company, CAS: 98-74-8) was used instead of methane sulfonyl chloride in Example 28 in step 1.

A white foam-like solid (57 mg, yield: 44%)

$^1$HNMR (CD$_3$OD, 300 MHz) δ: 8.41 (d, 2H, J=8.7 Hz), 8.12 (d, 2H, J=8.7 Hz), 7.45-7.42 (m, 2H), 7.23-7.20 (m, 1H), 4.45-4.40 (m, 1H), 3.87-3.83 (m, 2H), 3.74-3.70 (m, 3H), 3.67-3.59 (m, 3H), 2.93-2.88 (m, 1H), 2.80-2.74 (m, 2H), 2.41 (s, 3H), 2.14-2.10 (m, 2H), 2.05 (s, 3H), 1.84-1.71 (m, 12H);

EI (LR-MS): 645 (M)$^+$, 196 (100);

EI (HR-MS): calc for. 645.2388. found 645.2390.

Example 31

Compound 9d: 1-acetyl-N-(3-chloro-4-methylphenyl)-N-(3-(3-exo-(3-nitrophenylsulfamide)-8-azabicyclo[3.2.1]oct-8-yl)propyl)-4-piperidinylcarboxamide

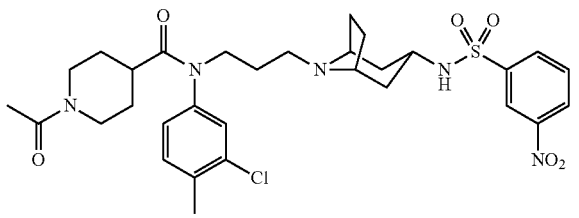 [SMILES: CC(=O)N1CCC(C(=O)N(CCCN2C3CCC2CC(NS(=O)(=O)c2cccc([N+](=O)[O-])c2)C3)c2ccc(C)c(Cl)c2)CC1]

3-nitrophenylsulfonic chloride (commercially available from ACROS Reagent Company, CAS: 121-51-7) was used instead of methane sulfonyl chloride in Example 28 in step 1.

A white foam-like solid (102 mg, yield: 79%) $^1$HNMR (CD$_3$OD, 300 MHz) δ: 8.68-8.67 (m, 1H), 8.49-8.47 (m, 1H), 8.29-8.26 (m, 1H), 7.88-7.83 (m, 1H), 7.45-7.43 (m, 2H), 7.23-7.21 (m, 1H), 4.45-4.39 (m, 1H), 3.87-3.82 (m, 1H), 3.75-3.71 (m, 4H), 3.70-3.61 (m, 1H), 2.87-2.84 (m, 3H), 2.41 (s, 3H), 2.16-2.12 (m, 2H), 2.05 (s, 3H), 1.84-1.81 (m, 10H), 1.71-1.67 (m, 4H);

EI (LR-MS): 645 (M)$^+$, 122 (100);
EI (HR-MS): calc for. 645.2388. found 645.2437.

Example 32

Compound 9e:

1-acetyl-N-(3-chloro-4-methylphenyl)-N-(3-(3-exo-(phenylmethylsulfonylamido)-8-azabicyclo[3.2.1]oct-8-yl)propyl)-4-piperidinylcarboxamide

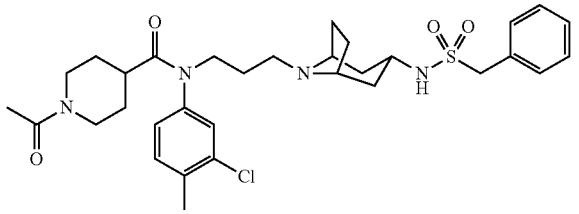 [SMILES: CC(=O)N1CCC(C(=O)N(CCCN2C3CCC2CC(NS(=O)(=O)Cc2ccccc2)C3)c2ccc(C)c(Cl)c2)CC1]

Phenylmethanesulfonyl chloride (commercially available from ACROS Reagent Company, CAS: 1939-99-7) was used instead of methane sulfonyl chloride in Example 28 in step 1.

A white foam-like solid (103 mg, yield: 65%)
$^1$HNMR (CD$_3$OD, 300 MHz) δ: 7.47-7.44 (m, 4H), 7.40-7.39 (m, 3H), 7.26-7.23 (m, 1H), 4.44-4.40 (m, 1H), 4.36 (s, 2H), 3.88-3.71 (m, 6H), 2.92-2.84 (m, 3H), 2.42 (s, 3H), 2.14-2.10 (m, 2H), 2.05 (s, 3H), 1.91-1.81 (m, 6H), 1.76-1.68 (m, 6H);

EI (LR-MS): 614 (M)$^+$, 227 (100);
EI (HR-MS): calc for. 614.2694. found 614.2690.

Example 33

Compound 9f: 1-acetyl-N-(3-chloro-4-methylphenyl)-N-(3-(3-exo-(thienyl-2-sulfonylamido)-8-azabicyclo[3.2.1]oct-8-yl)propyl)-4-piperidinylcarboxamide

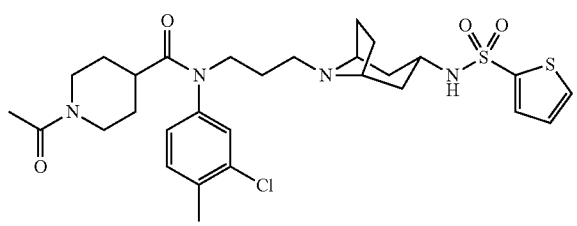 [SMILES: CC(=O)N1CCC(C(=O)N(CCCN2C3CCC2CC(NS(=O)(=O)c2cccs2)C3)c2ccc(C)c(Cl)c2)CC1]

2-thienylsulfonyl chloride (commercially available from ACROS Reagent Company, CAS: 16629-19-9) was used instead of methane sulfonyl chloride in Example 28 in step 1.

A white foam-like solid (70 mg, yield: 58%)
$^1$HNMR (CD$_3$OD, 300 MHz) δ: 7.80-7.78 (m, 1H), 7.66-7.65 (m, 1H), 7.46-7.43 (, 2H), 7.25-7.22 (m, 1H), 7.17-7.13 (m, 1H), 4.45-4.39 (m, 1H), 3.88-3.83 (m, 2H), 3.77-3.73 (m, 4H), 3.63-3.57 (m, 1H), 2.92-2.85 (m, 3H), 2.41 (s, 3H), 2.19-2.15 (m, 2H), 2.04 (s, 3H), 1.86-1.82 (m, 9H), 1.72-1.64 (m, 4H);

EI (LR-MS): 606 (M)$^+$, 285 (100);
EI (HR-MS): calc for. 606.2101. found 606.2123.

Example 34

Compound 10a:

1-acetyl-N-(3-chloro-4-methylphenyl)-N-(3-(3-exo-(3-(4-methoxylphenyl)ureylene)-8-azabicyclo[3.2.1]oct-8-yl)propyl)-4-piperidinylcarboxamide

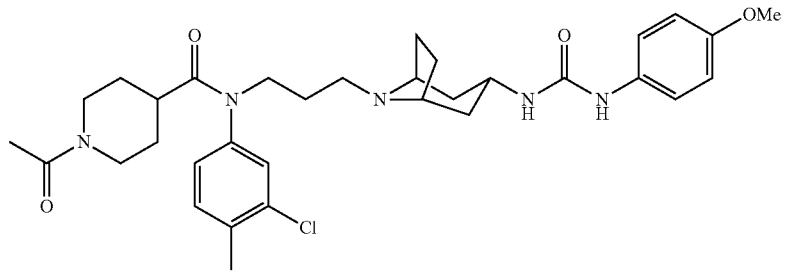 [SMILES: COc1ccc(NC(=O)NC2CC3CCC(C2)N3CCCN(C(=O)C2CCN(C(C)=O)CC2)c2ccc(C)c(Cl)c2)cc1]

Step 1: 1-acetyl-N-(3-chloro-4-methylphenyl)-N-(3-(3-exo-(3-(4-methoxylphenyl)ureylene)-8-azabicyclo[3.2.1]oct-8-yl)propyl)-4-piperidinylcarboxamide p-methoxylphenylisocyanate (19 mg, 0.13 mmol) (commercially available from ACROS Reagent Company, CAS: 5416-93-3) was added into a solution of the compound 6 (60 mg, 0.13 mmol) prepared in example 1 in dichloromethane (3 mL) and stirred for 4 hour at the same temperature. The reaction mixture was diluted with dichloromethane, and washed with saline. The organic phase was dried with sodium sulfate and concentrated under reduced pressure. The concentrate was separated through column chromatography (dichloromethane/methanol=10/1, v/v) to obtain the product as a white foam-like solid (58 mg, yield: 73%).

$^1$HNMR (CD$_3$OD, 300 MHz) δ: 7.45-7.43 (m, 2H), 7.22-7.19 (m, 3H), 6.82 (d, 2H, J=9.0 Hz), 5.49 (br, 1H), 4.45-4.41 (m, 1H), 4.02-3.97 (m, 1H), 3.88-3.83 (m, 1H), 3.74 (s, 3H), 3.48 (br, 2H), 3.34-3.33 (m, 1H), 2.92-2.83 (m, 1H), 2.63-2.58 (m, 2H), 2.51-2.46 (m, 1H), 2.42 (s, 3H), 2.39-2.34 (m, 1H), 2.09-2.08 (m, 1H), 2.05 (s, 3H), 1.92-1.54 (m, 14H);
EI (LR-MS): 609 (M)$^+$, 139 (100).

Example 35

Compound 10b:

1-acetyl-N-(3-(3-(3-(4-chloro-3-(trifluoromethyl)phenyl)ureylene)-8-azabicyclo[3.2.1]oct-8-yl)propyl)-N-(3-chloro-4-methylphenyl)-4-piperidinylcarboxamide

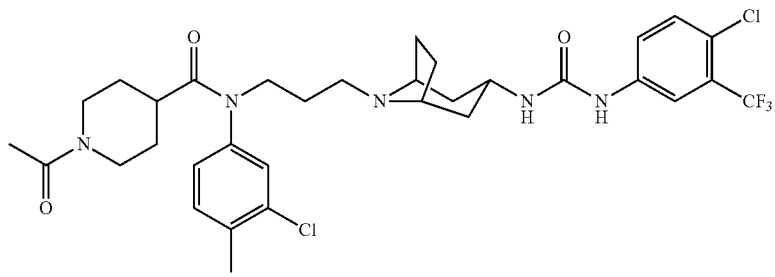 [SMILES: CC(=O)N1CCC(C(=O)N(CCCN2C3CCC2CC(NC(=O)Nc2ccc(Cl)c(C(F)(F)F)c2)C3)c2ccc(C)c(Cl)c2)CC1]

The example 35 has similar reaction conditions as those in example 34, except using 3-trifluoromethyl-4-chlorphenylisocyanate (commercially available from ACROS Reagent Company, CAS: 327-78-6) instead of p-methoxylphenylisocyanate in the last step.

A white foam-like solid (68 mg, yield: 77%)
$^1$HNMR (CD$_3$OD, 300 MHz) δ: 7.92 (d, 1H, J=2.1 Hz), 7.52-7.42 (m, 4H), 7.21 (dd, 1H, J=2.1 Hz, 8.1 Hz), 5.49 (br, 1H), 4.45-4.41 (m, 1H), 4.03-3.97 (m, 1H), 3.88-3.84 (m, 1H), 3.76-3.71 (m, 2H), 3.47 (br, 2H), 2.93-2.84 (m, 1H), 2.62-2.57 (m, 2H), 2.51-2.48 (m, 1H), 2.42 (s, 3H), 2.39-2.34 (m, 1H), 2.05 (s, 3H), 1.92-1.56 (m, 14H).

Example 36

Compound 10c:

1-acetyl-N-(3-(3-(3-phenylureylene)-8-azabicyclo[3.2.1]oct-8-yl)propyl)-N-(3-chloro-4-methylphenyl)-4-piperidinylcarboxamide

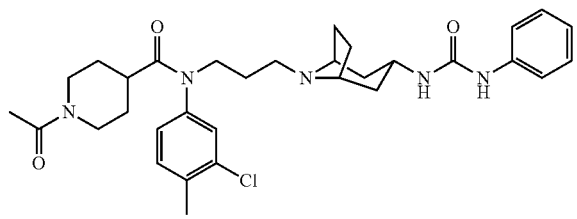 [SMILES: CC(=O)N1CCC(C(=O)N(CCCN2C3CCC2CC(NC(=O)Nc2ccccc2)C3)c2ccc(C)c(Cl)c2)CC1]

The example 36 has similar reaction conditions as those in example 34, except using phenylisocyanate (commercially available from ACROS Reagent Company, CAS: 103-71-9) instead of p-methoxylphenylisocyanate in the last step.

A white foam-like solid (79 mg, yield: 36%)
$^1$HNMR (CDCl$_3$, 300 MHz) δ: 7.40-7.37 (m, 2H), 7.30-7.26 (m, 2H), 7.19-7.14 (m, 3H), 6.96-6.91 (m, 1H), 6.18 (d, 1H, J=7.2 Hz), 4.53-4.49 (m, 1H), 4.19 (br, 1H), 3.78-3.71 (m, 6H), 2.85-2.76 (m, 3H), 2.38 (s, 3H), 2.34-2.27 (m, 4H), 2.16-2.10 (m, 6H), 2.04 (s, 3H), 1.74-1.62 (m, 5H).

Example 37

Compound 11: 1-acetyl-N-(3-chloro-4-methylphenyl)-N-(3-(3-exo-(3-isopropyl-5-methyl-4-hydro-1,2,4-triazol-4-yl)-8-azabicyclo[3.2.1]oct-8-yl)propyl)-4-piperidinylcarboxamide

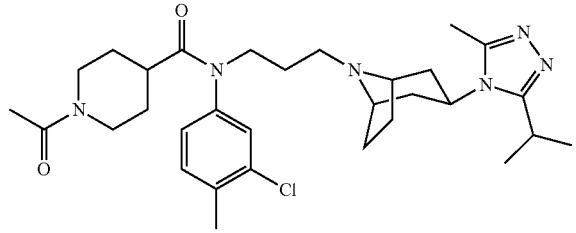 [SMILES: CC(=O)N1CCC(C(=O)N(CCCN2C3CCC2CC(n2c(C)nnc2C(C)C)C3)c2ccc(C)c(Cl)c2)CC1]

Step 1: 8-benzyl-8-azabicyclo[3.2.1]octan-3-one

A solution of 2,5-dimethoxytetrahydrofuran (2.2 mL) in hydrochloric acid (0.1N, 20 mL) was stirred under refluxing for 1 hour and then cooled to 0° C. 1,3-acetone-dicarboxylic acid (2.5 g), benzylamine (2.25 mL) and 10% sodium acetate solution (10 mL) were added therein. The reaction mixture was stirred for 1 hour at room temperature, and additionally stirred for 5 hours at 50° C., and then cooled under ice bath. The reaction mixture was alkalized to pH 12 using a 2N sodium hydroxide solution. After layer-separated, the aqueous phase is diluted with ethyl acetate. The combined organic phase was washed with water, dried with anhydrous sodium sulfate, filtered and vaporized under reduced pressure. The concentrate was separated through column chromatography (petroleum ether/ethyl acetate=4/1, v/v) to obtain the product as brown oil (2239 mg, yield: 61%).

$^1$HNMR (CDCl$_3$, 300 MHz) δ: 7.43-7.24 (m, 5H), 3.75 (s, 2H), 3.49-3.48 (m, 2H), 2.72-2.66 (m, 2H), 2.23 (s, 1H), 2.18-2.16 (m, 1H), 2.14-2.09 (m, 2H), 1.66-1.59 (m, 2H).

Step 2: 8-benzyl-8-azabicyclo[3.2.1]octan-3-one oxime

A solution of the product from step 1 (1809 mg, 8.4 mmol), hydroxylamine chloride (642 mg, 9.25 mmol) and pyridine (0.72 mL) in ethanol (40 mL) was stirred under refluxing for 18 hour, then cooled to room temperature and vaporized off the solvent under reduced pressure. The residue was diluted with dichloromethane. The organic extracted phase was washed with water, dried with anhydrous sodium sulfate, filtered and vaporized under reduced pressure. The concentrate was separated through column chromatography (petroleum ether/ethyl acetate=3/1 to 1/1, v/v) to provide the product as a light-brown solid (1151 mg, yield: 59%).

$^1$HNMR (CDCl$_3$, 300 MHz) δ: 7.41-7.23 (m, 5H), 3.65 (s, 2H), 3.35 (s, 2H), 3.00-2.95 (d, 1H, J=15.9 Hz), 2.63-2.57 (dd, 1H, J=3.3 Hz, 11.7 Hz), 2.27-2.21 (dd, 1H, J=3.6 Hz, 12.0 Hz), 2.16-2.11 (d, 1H, J=14.4 Hz), 2.03-2.01 (m, 2H), 1.65-1.59 (m, 1H), 1.55-1.49 (m, 1H).

Step 3: 3-exo-amino-8-benzyl-8-azabicyclo[3.2.1]octane

Metal sodium (8970 mg, 390 mmol) was added in batches into a solution (100 mL) of the product (6904 mg, 30 mmol) in step 2 in n-pentanol under refluxing and stirring. After the addition of metal sodium, the stirring continued for 2 hours under refluxing, and then the reaction mixture was cooled in ice bath and the reaction was quenched by adding water slowly until no generation of hydrogen. The mixture was acidified with 6N HCl and layer-separated, and the organic phase was washed with 6N HCl. The combined aqueous phase was alkalified to pH=12 with sodium hydroxide, and extracted with ethyl acetate. The combined organic phase was dried with anhydrous sodium sulfate, filtered and vaporized under reduced pressure to obtain a solid product (4492 mg, yield: 69%).

$^1$HNMR (CDCl$_3$, 300 MHz) δ: 7.38-7.22 (m, 5H), 3.56 (s, 2H), 3.19 (br-s, 2H), 3.01-2.89 (m, 1H), 2.04-1.97 (m, 2H), 1.73-1.65 (m, 2H), 1.60-1.53 (m, 2H), 1.51-1.47 (m, 2H), 1.43-1.23 (m, 2H).

Step 4: N-(8-benzyl-8-azabicyclo[3.2.1]oct-3-yl-exo)-2-methylpropionamide

The product prepared in step 3 (6092 mg, 28.18 mmol) and sodium carbonate (5974 mg, 56.36 mmol) were dissolved in a mixed solution of dichloromethane (30 mL) and water (30 mL), and then isobutyryl chloride (3603 mg, 33.81 mmol) was added therein under ice-cooling. After the addition, the mixture was warmed up to room temperature and stirred for another 2 hours. The reaction mixture was diluted with dichloromethane, and layer-separated. The aqueous phase was extracted with dichloromethane. The combined organic phase was dried with sodium sulfate, and concentrated. The concentrate was separated through column chromatography (dichloromethane/methanol=40/1, v/v) to obtain the product as a white solid (6605 mg, yield: 82%).

Step 5: 8-benzyl-3-(3-isopropyl-5-methyl-tetrahydro-1,2,4-triazol-4-yl)-exo-8-azabicyclo[3.2.1]octane A solution of phosphorus pentachloride (475 mg, 2.28 mmol) in dichloromethane (4 mL) was cooled in ice bath, and a solution of the product prepared in step 4 (502 mg, 1.75 mmol) in dichloromethane (2 mL) was added slowly therein while keeping the reaction temperature less than 10° C. After the addition, the mixture was stirred for 2 hours at room temperature, and then cooled to 0° C. followed by slowly adding a solution of acetohydrazide (260 mg, 3.5 mmol) in 2-methyl-2-butanol (3 mL) while keeping the reaction temperature less than 10° C. After the addition, the mixture was warmed up to room temperature and the stirring continued for hours. The reaction was quenched by using 10 N sodium hydroxide solution under ice bath and the pH was adjusted to 12. After layer-separated, the aqueous phase was extracted with ethyl acetate. The combined organic phase was dried with sodium sulfate, and concentrated.

The concentrate was separated through column chromatography (dichloromethane/methanol=40/1, v/v) to give the product as a white solid (337 mg, yield: 59%).

Step 6:

3-(3-isopropyl-5-methyl-tetrahydro-1,2,4-triazol-4-yl)-exo-8-azabicyclo[3.2.1]octane Ammonium formate (630 mg, 10 mmol) was added in a solution of the product prepared in step 5 (321 mg, 1 mmol) and 10% Pd/C (32 mg) in ethanol (10 mL). The reaction mixture was stirred and refluxed for 12 hours under nitrogen atmosphere, and then vaporized off the solvent under reduced pressure, diluted with dichloromethane, and washed with water. The aqueous phase was extracted with dichloromethane, and the combined organic phase was dried with sodium sulfate, and concentrated to obtain the product as a white solid (135 mg, yield: 58%).

$^1$HNMR (CDCl$_3$, 300 MHz) δ: 4.39-4.27 (m, 1H), 3.47 (s, 2H), 3.07-2.98 (m, 1H), 2.53 (s, 3H), 2.26-2.18 (m, 2H), 1.99-1.96 (m, 2H), 1.79-1.76 (d, 4H, J=8.1 Hz), 1.40-1.38 (d, 6H, J=6.9 Hz).

Step 7:

1-acetyl-N-(3-chloro-4-methylphenyl)-N-(3-(3-exo-(3-isopropyl-5-methyl-4-hydro-1,2,4-triazol-4-yl)-8-azabicyclo[3.2.1]oct-8-yl)propyl)-4-piperidinylcarboxamide (compound 11)

A solution of 1-acetyl-N-(3-chloro-4-methylphenyl)-N-(3-chloropropyl)-4-piperidinylcarboxamide (185 mg, 0.5 mmol), the product prepared in step 6 (129 mg, 0.55 mmol) and triethylamine (0.21 mL, 1.5 mmol) in acetonitrile (5 mL) was stirred and refluxed for 24 hours, and then vaporized off the solvent, diluted with ethyl acetate, and washed with water and saline respectively. The separated organic phase was dried with sodium sulfate and concentrated under reduced pressure. The concentrate was separated through column chromatography (dichloromethane/methanol=20/1 to 10/1, v/v) to give a yellowish foam-like product (28 mg, yield: 10%).

$^1$HNMR (CDCl$_3$, 300 MHz) δ: 7.36-7.30 (m, 1H), 7.20 (s, 1H), 7.01-6.97 (m, 1H), 4.55-4.48 (m, 1H), 4.30-4.20 (m, 1H), 3.49-3.44 (m, 1H), 3.31 (br-s, 2H), 3.00-2.96 (m, 1H), 2.89-2.79 (m, 1H), 2.43 (s, 3H), 2.48-2.35 (m, 6H), 2.05 (s, 3H), 2.18-1.96 (m, 5H), 1.75-1.62 (m, 12H), 1.38-1.25 (m, 6H);

EI (LR-MS): 568 (M)$^+$, 335 (100);

EI (HR-MS): calc for. 568.3293. found 568.3288.

Example 38

Compound 15a:

N-(3-chloro-4-methylphenyl)-N-(3-(3-exo-(4-tolyl-sulfonamido)-8-azabicyclo[3.2.1]oct-8-yl)propyl) cyclohexylcarboxamide utes under ice bath. Then the compound 1 (481 mg, 2.21 mmol) prepared in the above example 1 was added therein and the stirring continued for 4 hours. After removing tetrahydrofuran under reduced pressure, the residue was separated through column chromatography (petroleum ether/ethyl acetate=20/1, v/v) to provide the compound 12 as a colourless oil (323 mg, yield: 47%).

$^1$HNMR (CDCl$_3$, 300 MHz) δ: 7.29-7.28 (m, 1H), 7.16-7.15 (m, 1H), 6.97-6.94 (m, 1H), 3.78-3.73 (m, 3H), 3.56-3.51 (m, 2H), 2.42 (s, 3H), 2.16-2.08 (m, 1H), 2.04-1.95 (m, 3H), 1.70-1.53 (m, 8H).

Step 2: N-(8-benzyl-3-exo-8-azabicyclo[3.2.1]oct-3-yl)-4-tolylsulfonamide

Triethylamine (0.81 mL, 5.9 mmol) and p-toluenesulfonyl chloride (840 mg, 4.4 mmol) were added in a solution of 8-benzyl-3-exo-8-azabicyclo[3.2.1]octyl-3-amine (641 mg, 2.9 mmol) in dichloromethane (10 mL), and stirred for 6 hours at room temperature. The dichloromethane was removed under reduced pressure, and the residue was separated through column chromatography (petroleum ether/ethyl acetate=1/1, v/v) to provide the compound 13 as a white foam-like solid (516 mg, yield: 48%).

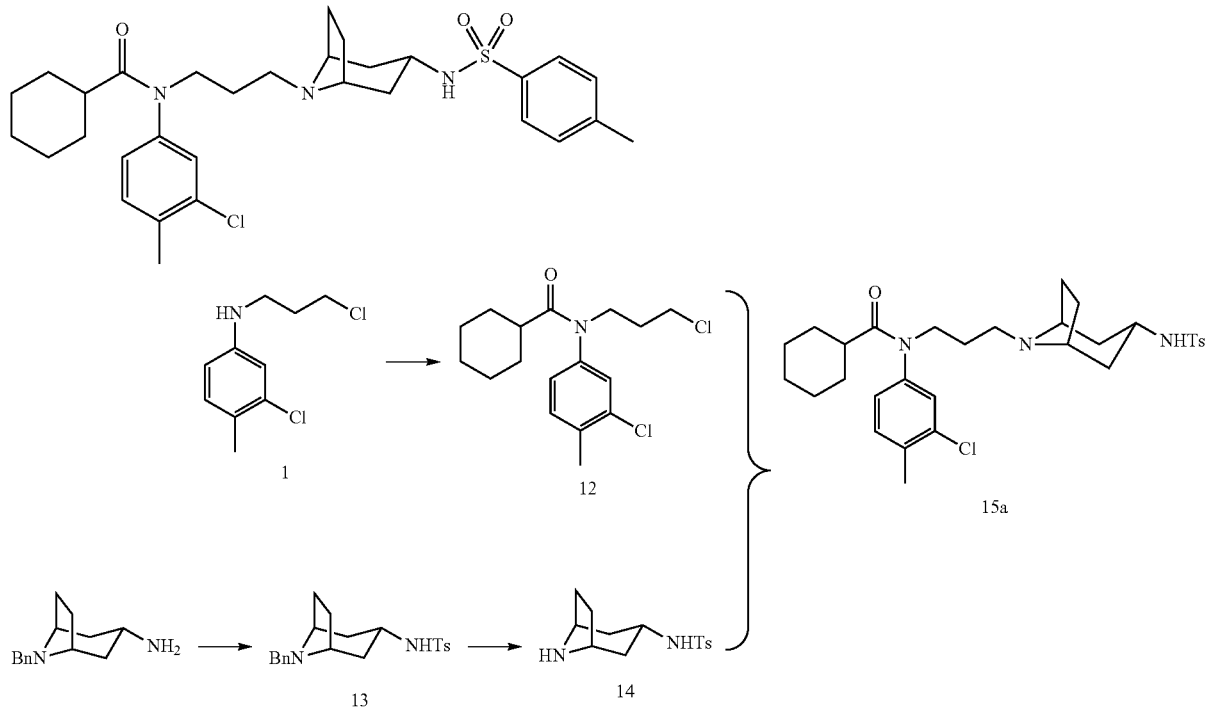

Step 1: N-(3-chloro-4-methylphenyl)-N-(3-chloropropyl)cyclohexylcarboxamide

N-methyl morpholine (0.54 mL, 4.85 mmol) was added in a solution of cyclohexanecarboxylic acid (282 mg, 2.21 mmol) in anhydrous tetrahydrofuran (10 mL). After stirring 15 minutes under ice bath, isobutyl chlorocarbonate (0.32 mL, 2.43 mmol) was slowly added in the above reaction system, and the stirring continued for 45 min- $^1$HNMR (CDCl$_3$, 300 MHz) δ: 7.76-7.74 (m, 2H), 7.32-7.29 (m, 7H), 4.31-4.27 (m, 1H), 3.50 (s, 2H), 3.16-3.13 (m, 2H), 2.42 (s, 3H), 2.02-1.97 (m, 2H), 1.59-1.54 (m, 6H).

Step 3: N-(3-exo-8-azabicyclo[3.2.1]oct-3-yl)-4-toluenesulfonamide

10% Pd/C (94 mg) and ammonium formate (561 mg, 8.91 mmol) were added in a solution of the prepared compound 13 (471 mg, 1.27 mmol) in methanol (10 mL). The mixture was stirred and refluxed for 12 hours. After removing methanol under reduced pressure, the residue was diluted with dichloromethane (10 mL), washed with saturated saline (10 mL), dried with anhydrous sodium sulfate, and concentrated to obtain the compound 14 as a white solid (304 mg, yield: 82%).

Step 4: N-(3-chloro-4-methylphenyl)-N-(3-(3-exo-(4-tolylsulfonamido)-8-azabicyclo[3.2.1]oct-8-yl) propyl)cyclohexylcarboxamide The above prepared compound 12 (131 mg, 0.4 mmol) was dissolved in acetonitrile (10 mL) followed by adding therein the compound 14 (112 mg, 0.4 mmol), potassium iodide (47 mg, 0.4 mmol) and potassium carbonate (166 mg, 1.2 mmol). The reaction mixture was heated to reflux for 6 hours, and then cooled to room temperature. After removing acetonitrile under reduced pressure, the residue was diluted with dichloromethane (10 mL) and washed with saturated saline (10 mL). The organic phases were separated, dried with sodium sulfate and concentrated. The concentrate was separated through column chromatography (dichloromethane/methanol=20/1, v/v) to give the object compound as a white solid (14 mg, yield: 7%).

$^1$HNMR (CDCl$_3$, 300 MHz) δ: 7.78-7.73 (m, 2H), 7.44-7.36 (m, 5H), 3.76-3.69 (m, 3H), 3.51-3.47 (m, 1H), 2.88-2.84 (m, 1H), 2.43 (s, 3H), 2.42 (s, 3H), 2.22-2.13 (m, 4H), 1.86-1.77 (m, 9H), 1.70-1.50 (m, 10H);
EI (LR-MS): 571 (M)$^+$, 337 (100).

Example 39

Compound 15b:

N-(3-chloro-4-methylphenyl)-N-(3-(3-exo-(4-tolylsulfonamido)-8-azabicyclo[3.2.1]oct-8-yl)propyl)-1-(methylsulfonyl)-4-piperidinylcarboxamide

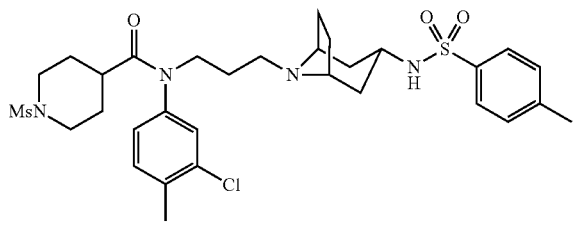

Step 1: N-(3-chloro-4-methylphenyl)-N-(3-chloropropyl)-1-(methylsulfonyl)-4-piperidinylcarboxamide The first step of example 39 had similar reaction conditions as those in example 38, except using 1-(methylsulfonyl)-4-piperidinylcarboxylic acid instead of cyclohexanecarboxylic acid.
A white foam-like solid (268 mg, yield: 33%)
$^1$HNMR (CD$_3$OD, 300 MHz) δ: 7.33-7.28 (m, 1H), 7.18 (s, 1H), 6.99-6.97 (m, 1H), 3.80-3.70 (m, 5H), 3.56-3.52 (m, 2H), 2.73 (s, 3H), 2.61-2.53 (m, 3H), 2.43 (s, 3H), 2.32-2.26 (m, 2H), 2.03-1.98 (m, 3H).

Steps 2 and 3 are the same as those in example 38.

Step 4: N-(3-chloro-4-methylphenyl)-N-(3-(3-exo-(4-tolylsulfonamido)-8-azabicyclo[3.2.1]oct-8-yl) propyl)-1-(methylsulfonyl)-4-piperidinylcarboxamide The fourth step in example 39 has similar reaction conditions as those in example 38, except using N-(3-chloro-4-methylphenyl)-N-(3-chloropropyl)-1-(methylsulfonyl)-4-piperidinyl carboxamide instead of the compound 12.
A white foam-like solid (26 mg, yield: 10%)
$^1$HNMR (CD$_3$OD, 300 MHz) δ: 7.77 (d, 2H, J=8.4 Hz), 7.45-7.38 (m, 4H), 7.23-7.20 (m, 1H), 3.76-3.71 (m, 4H), 3.66-3.62 (m, 2H), 3.57-3.51 (m, 1H), 2.90-2.85 (m, 2H), 2.72 (s, 3H), 2.54-2.49 (m, 2H), 2.43 (s, 3H), 2.41 (s, 3H), 2.37-2.32 (m, 1H), 2.19-2.13 (m, 2H), 1.88-1.84 (m, 3H), 1.81-1.77 (m, 9H).
EI (LR-MS): 650 (M)$^+$, 82 (100).

Example 40

Compound 15c: 3-chloro-4-methylphenyl(3-(3-exo-(4-toluenesulfonamido)-8-azabicyclo[3.2.1]oct-8-yl) propyl)carbamic acid benzyl ester

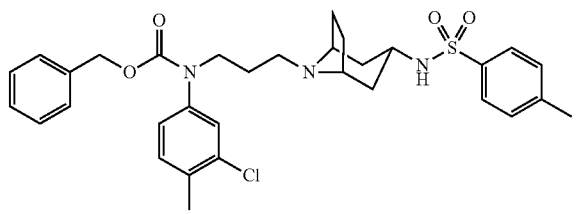 [SMILES: Cc1ccc(S(=O)(=O)NC2CC3CCC(C2)N3CCCN(C(=O)OCc2ccccc2)c2ccc(C)c(Cl)c2)cc1]

Step 1: 3-chloro-4-methylphenyl(3-chloropropyl)carbamic acid benzyl ester

After adding triethylamine (0.153 mL, 1.1 mmol) into a solution of the compound 1 (217 mg, 1 mmol) in anhydrous dichloromethane (10 mL), the mixture was cooled to 0° C. followed by dropwise addition of benzyloxycarbonyl chloride (0.17 mL, 1.05 mmol). The stirring continued for 1 hour at the same temperature. The reaction mixture was diluted with dichloromethane, and washed by saline. The organic phase was dried with sodium sulfate and concentrated under reduced pressure. The concentrate was separated through column chromatography (petroleum ether/ethyl acetate=10/1, v/v) to obtain the product as a white oil-like solid (204 mg, yield: 58%).
$^1$HNMR (CDCl$_3$, 300 MHz) δ: 7.45-7.38 (m, 5H), 7.32-7.28 (m, 1H), 7.19-7.17 (m, 1H), 6.99-6.97 (m, 1H), 5.02 (s, 2H), 3.76-3.69 (m, 2H), 3.56-3.52 (m, 2H), 2.42 (s, 3H), 2.32-2.26 (m, 2H).

Step 2: 3-chloro-4-methylphenyl(3-(3-exo-(4-tolylsulfonamido)-8-azabicyclo[3.2.1]oct-8-yl)propyl) carbamic acid benzyl ester After dissolving the above prepared compound 3-chloro-4-methylphenyl(3-chloropropyl)carbamic acid benzyl ester (204 mg, 0.58 mmol) in acetonitrile (10 mL), the compound 14 (163 mg, 0.58 mmol), potassium iodide (96 mg, 0.58 mmol) and potassium carbonate (240 mg, 1.74 mmol) were added therein in turns. After heated to reflux for 6 hours, the reaction mixture was cooled to room temperature, distilled off acetonitrile under reduced pressure, diluted with dichloromethane (10 mL) and washed with saturated saline. The organic phase was separated, dried with sodium sulfate and concentrated. The concentrate was separated through column chromatography (dichloromethane/methanol=20/1, v/v) to obtain the object product as a white oil-like solid (52 mg, yield: 15%).

$^1$HNMR (CDCl$_3$, 300 MHz) δ: 7.78-7.73 (m, 4H), 7.45-7.32 (m, 8H), 5.09 (s, 2H), 3.76-3.69 (m, 3H), 3.51-3.47 (m, 1H), 2.84-2.81 (m, 1H), 2.43 (s, 3H), 2.42 (s, 3H), 2.22-2.13 (m, 4H), 1.86-1.77 (m, 8H).

Example 41

Compound 15d:

N-(8-(3-(1-(3-chloro-4-methylphenyl)-3-(phenylureylene)propyl)-3-exo-8-azabicyclo[3.2.1]oct-3-yl)-4-tolylsulfonamide

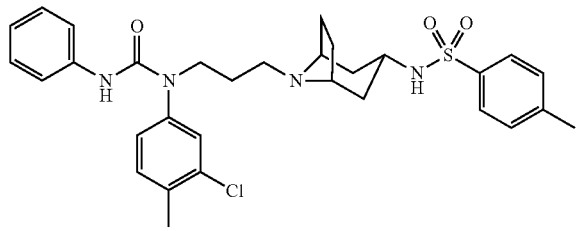 [SMILES: Cc1ccc(S(=O)(=O)NC2CC3CCC(C2)N3CCCN(C(=O)Nc2ccccc2)c2ccc(C)c(Cl)c2)cc1]

Step 1: 1-(3-chloro-4-methylphenyl)-1-(3-chloropropyl)-3-phenylurea

The first step in example 41 has similar reaction conditions as those in Example 40, except using phenylisocyanate instead of benzyloxycarbonyl chloride.

A white foam-like solid (144 mg, yield: 43%)

$^1$HNMR (CDCl$_3$, 300 MHz) δ: 7.40-7.32 (m, 5H), 7.30-7.28 (m, 1H), 7.17-7.15 (m, 1H), 6.99-6.96 (m, 1H), 3.74-3.69 (m, 2H), 3.56-3.53 (m, 2H), 2.41 (s, 3H), 2.33-2.26 (m, 2H).

Step 2:

N-(8-(3-(1-(3-chloro-4-methylphenyl)-3-(phenylureylene)propyl)-3-exo-8-azabicyclo[3.2.1]oct-3-yl)-4-tolylsulfonamide The second step in example 41 had similar reaction conditions as those in Example 40, except using 1-(3-chloro-4-methylphenyl)-1-(3-chloropropyl)-3-phenylurea instead of the compound 3-chloro-4-methylphenyl(3-chloropropyl)carbamic acid benzyl ester.

A white foam-like solid (49 mg, yield: 18%)

$^1$HNMR (CDCl$_3$, 300 MHz) δ: 7.79-7.73 (m, 4H), 7.45-7.32 (m, 8H), 3.76-3.67 (m, 3H), 3.51-3.46 (m, 1H), 2.83-2.81 (m, 1H), 2.43 (s, 3H), 2.42 (s, 3H), 2.21-2.13 (m, 4H), 1.88-1.77 (m, 8H).

Example 42

Compound 15e: N-(3-chloro-4-methylphenyl)-4-methyl-N-(3-(3-exo-(4-tolylsulfonamido)-8-azabicyclo[3.2.1]oct-8-yl)propyl)phenylsulfonamide

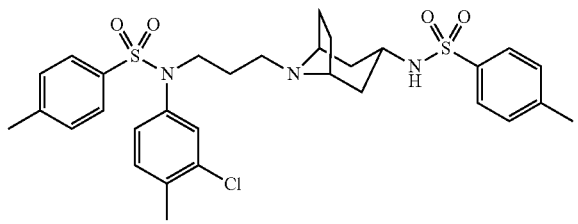

Step 1: N-(3-chloro-4-methylphenyl)-N-(3-chloropropyl)-4-tolylsulfonamide

The first step in example 42 had similar reaction conditions as those in Example 40, except using p-methylphenylsulfonyl chloride instead of benzyloxycarbonyl chloride.

A white foam-like solid (193 mg, yield: 52%)

$^1$HNMR (CDCl$_3$, 300 MHz) δ: 7.42-7.32 (m, 5H), 7.30-7.28 (m, 1H), 7.18-7.15 (m, 1H), 6.98-6.96 (m, 1H), 3.76-3.69 (m, 2H), 3.56-3.51 (m, 2H), 2.42 (s, 3H), 2.41 (s, 3H), 2.31-2.26 (m, 2H).

Step 2: N-(3-chloro-4-methylphenyl)-4-methyl-N-(3-(3-exo-(4-tolylsulfonamido)-8-azabicyclo[3.2.1]oct-8-yl)propyl)phenylsulfonamide The second step in example 42 had similar reaction conditions as those in Example 40, except using N-(3-chloro-4-methylphenyl)-N-(3-chloropropyl)-4-tolylsulfonamide instead of the compound 3-chloro-4-methylphenyl (3-chloropropyl)carbamic acid benzyl ester.

A white foam-like solid (45 mg, yield: 14%)

$^1$HNMR (CDCl$_3$, 300 MHz) δ: 7.79-7.73 (m, 4H), 7.44-7.30 (m, 7H), 3.76-3.68 (m, 3H), 3.51-3.47 (m, 1H), 2.83-2.82 (m, 1H), 2.43 (s, 3H), 2.42 (s, 3H), 2.41 (s, 3H), 2.21-2.12 (m, 4H), 1.89-1.77 (m, 8H).

Example 43

Compound 15f:

N-(3-chloro-4-methylphenyl)-N-(3-(3-exo-(4-tolylsulfonamido)-8-azabicyclo[3.2.1]oct-8-yl)propyl) acetamide

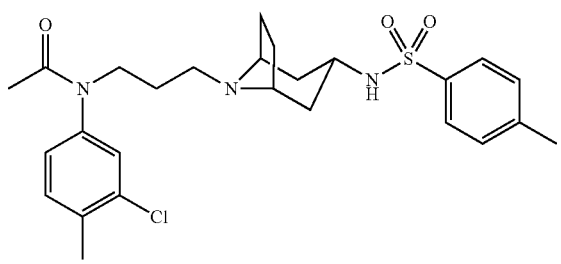 [SMILES: CC(=O)N(CCCN1C2CCC1CC(NS(=O)(=O)c1ccc(C)cc1)C2)c1ccc(C)c(Cl)c1]

Step 1: N-(3-chloro-4-methylphenyl)-N-(3-chloro-propyl)-acetamide

The first step in example 43 had similar reaction conditions as those in Example 40, except using acetyl chloride instead of benzyloxycarbonyl chloride.

A white foam-like solid (187 mg, yield: 72%)

$^1$HNMR (CDCl$_3$, 300 MHz) δ: 7.31-7.29 (m, 1H), 7.17-7.14 (m, 1H), 6.99-6.95 (m, 1H), 3.74-3.69 (m, 2H), 3.56-3.54 (m, 2H), 2.43 (s, 3H), 2.41 (s, 3H), 2.33-2.27 (m, 2H).

Step 2: N-(3-chloro-4-methylphenyl)-N-(3-(3-exo-(4-tolylsulfonamido)-8-azabicyclo[3.2.1]oct-8-yl)propyl)acetamide The second step in example 43 had similar reaction conditions as those in Example 40, except using N-(3-chloro-4-methylphenyl)-N-(3-chloropropyl)-acetamide instead of the compound 3-chloro-4-methylphenyl(3-chloropropyl)carbamic acid benzyl ester.

A white foam-like solid (65 mg, yield: 18%)

$^1$HNMR (CDCl$_3$, 300 MHz) δ: 7.77 (d, 2H, J=8.4 Hz), 7.45-7.38 (m, 4H), 7.23-7.20 (m, 1H), 3.76-3.68 (m, 3H), 3.51-3.47 (m, 1H), 2.83-2.80 (m, 1H), 2.43 (s, 3H), 2.42 (s, 3H), 2.41 (s, 3H), 2.22-2.13 (m, 4H), 1.88-1.79 (m, 8H).

Example 44

Compound 15g:

N-(8-(3-(N-(3-chloro-4-methylphenyl)methylsulfamido)propyl)-3-exo-8-azabicyclo[3.2.1]oct-3-yl)-4-tolylsulfonamide

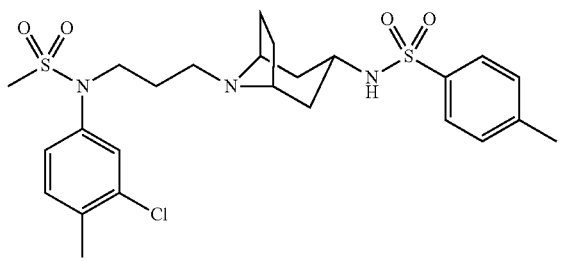

Step 1: N-(3-chloro-4-methylphenyl)-N-(3-chloro-propyl)-methylsulfamide

The first step in example 44 had similar reaction conditions as those in Example 40, except using methanesulfonyl chloride instead of benzyloxycarbonyl chloride.

A white foam-like solid (139 mg, yield: 47%)

$^1$HNMR (CDCl$_3$, 300 MHz) δ: 7.31-7.28 (m, 1H), 7.17-7.13 (m, 1H), 6.99-6.95 (m, 1H), 3.75-3.69 (m, 2H), 3.56-3.54 (m, 2H), 2.78 (s, 3H), 2.41 (s, 3H), 2.32-2.26 (m, 2H).

Step 2:

N-(8-(3-(N-(3-chloro-4-methylphenyl)methylsulfamido)propyl)-3-exo-8-azabicyclo[3.2.1]oct-3-yl)-4-tolylsulfonamide The second step in example 44 had similar reaction conditions as those in Example 40, except using N-(3-chloro-4-methylphenyl)-N-(3-chloropropyl)-methylsulfamide instead of the compound 3-chloro-4-methylphenyl(3-chloropropyl)carbamic acid benzyl ester.

A white foam-like solid (30 mg, yield: 12%)

$^1$HNMR (CDCl$_3$, 300 MHz) δ: 7.76 (d, 2H, J=8.4 Hz), 7.44-7.39 (m, 4H), 7.22-7.20 (m, 1H), 3.76-3.69 (m, 3H), 3.51-3.48 (m, 1H), 2.82-2.80 (m, 1H), 2.78 (s, 3H), 2.42 (s, 3H), 2.41 (s, 3H), 2.21-2.13 (m, 4H), 1.89-1.79 (m, 8H).

Experimental Examples on Biologic Activities

1. The Results of Activity Test at Molecular Level

CCR5 belongs to G-Protein-Coupled Receptor (GPCR) family. The developing technology of GPCR-based drugs have been well-developed, among them, the experimental techniques such as ligand-receptor binding assay, GTPγS binding assay and Ca$^{2+}$ flux assay have been widely used in drug-screening related to chemokine receptors. The inhibitory activities of the compounds according to the present invention against CCR5 are measured by three methods, i.e., [$^{35}$S]GTPγS filter binding assay, SPA-WGA-based [$^{35}$S]GTPγS binding assay and calcium influx assay. At the same time, the antiviral activities in cell of the compounds according to the present invention are evaluated by using two kinds HIV-1 subtypes: H4DA5 cell model and PBMC system virus replication model.

A. [$^{35}$S]GTPγS Binding Assay

After binding with an agonist, CCR5 experiences a conformation change such that CCR5 interacts with G protein so as to active the G protein. G protein is a tripolymer composed of α-subunit and βγ-subunit. Since the ability of α-subunit binding to GTP depends on the interaction of CCR5 with the agonist, the ability of an agonist for activating CCR5 can be reflected by determining the amount of GTP binding to α-subunit. In a GTPγS binding assay, a $^{35}$S-labeled GTP analogue GTPγS, which can bind with an activated α-subunit without being hydrolyzed, is used to replace GTP in order for eliminating the defect that the amount of GTP binding to G protein can not exactly reflect the activation of CCR5 due to the hydrolysis of GTO by GTPase and for convenience of detection. So, α-subunit binds with GDP when CCR5 is not activated, and after the activation of CCR5, α-subunit binds with GTPγS such that GTPγS irreversible binds to α-subunit. Therefore, the amount of [$^{35}$S]-GTPγS binding to α-subunit could reflect the level of CCR5 activated by an agonist. The ability of the agonist for activating CCR5 will decrease when an antagonist is added.

Such experiment has been referred to as GTPγS filtration assay in which [$^{35}$S]-GTPγS bound with the free G protein could be separated by membrane filtration.

Alternatively, SPA (Scintillation Proximity Assay) technique can be used to detect the [$^{35}$S]-GTPγS bound to G protein, which is called SPA-WGA-based [35S]GTPγS binding assay. The principle of SPA technique is as follows. Subatomic particles released during the decay of radioactive atoms, for example β-ray (electron), can excite microspheres at a sufficiently close distance to emit light so as to be detected by a Scintillation Counter. In an aqueous solution, most of the energy of these rays is absorbed by the solvent, and the traveling distance of these rays is limited. Hence, if light-emitting microspheres are bound to a cell membrane through wheat germ agglutinin (WGA), only [$^{35}$S]-GTPγS bound to G protein could have a sufficiently short distance to excite the microspheres to emit light so as to reflect the activation of receptors.

The activation of G protein by CCR5 is determined by the following experiments.

CHO (Chinese hamster ovary cell) permanent cell line expressing CCR5 (CHO-CCR5) (a cell line constructed by Shanghai Targetdrug Ltd.) was lysed with a lysis buffer (5 mM Tris-HCl, pH 7.5, 5 mM EDTA and 5 mM EGTA) and then centrifugated at 15,000×g for 10 min to obtain cell membrane. After the cell membrane was resuspended in a reaction buffer (5 mM Tris-HCl, pH 7.5, 5 mM $MgCl_2$, 1 mM EGTA, 100 mM NaCl), the protein concentration was determined using Bioford Protein Assay Kit manufactured by Bio-Rad Laboratories Inc. Subsequently, GTPγS binding assay was performed in the reaction buffer, wherein the reaction system was 100 μL containing 10 μg membrane protein, 40 μM GDP and 0.5 nM [$^{35}$S]-GTPγS (1200 Ci/mmol). After the compound to be tested (the compound was first dissolved in DMSO and then diluted in gradient with the reaction buffer according to the specific situation, wherein the final concentration of DMSO was 1% (v/v) in the whole reaction system) was added and shaken to mix homogeneously, the reaction tube was incubated at 30° C. for 1 hour. After the reaction finished, the tube was placed on ice, and the reaction mixture was diluted with PBS to quench the reaction and filtered under reduced pressure with a GF/C filter membrane. Subsequently, the bound radioactive signal was read by a liquid scintillation counter after adding a scintillation fluid, which is so called GTPγS filtration assay. The SPA-WGA assay is the same as the GTPγS assay in the first several steps, except that 0.1 mg/tube SPA-WGA microballoons (commercially available from Amersham Corporation) were added in the reaction system, followed by the addition of the compound to be tested, and after mixed homogeneously, the reaction system was incubated at 30° C. for 1 hour and then placed on ice to slower the reaction. The reaction mixture was centrifugated at 1000 rpm for 15 min at room temperature and then determined on a liquid scintillation counter.

The radioactive signal was read by a liquid scintillation counter. The basal binding was determined without the presence of an antagonist, and non-specific binding was determined with the existence of 10 μM non-isotopic GTPγS. Binding percentage of [$^{35}$S]-GTPγS was calculated through the equation: 100×[c.p.m.$_{sample}$−c.p.m.$_{non-specific}$]/[c.p.m.$_{basal}$−c.p.m.$_{non-specific}$], wherein c.p.m.$_{sample}$ represents the final tested CPM value of the sample adding the compound to be tested, and c.p.m.$_{basal}$ represents the final tested CPM value of the sample in which agonist was added without the compound to be tested. $IC_{50}$ represents the concentration of the compound when binding percentage of [$^{35}$S]-GTPγS is 50% caused by the inhibition of 10 nM RANTES (a kind of cytokine having intense chemotaxis to monocaryon-macrophage) and can be obtained from the concentration curve of the compound.

When studying the concentration-inhibition curve, the max value of CPM or RFU under the action of the agonist RANTES was taken as 100% and the basal value of CPM or RFU was taken as 0%, and then an $IC_{50}$ value of the antagonist was obtained through fitted on the statistical software Sigmaplot. When the concentration of the compound was 1 μM and the measured antagonistic effect thereof against CCR5 did not exceeded 90%, a virtual concentration is required for convenience of plotting. In the current study, the vitural point is that when concentration of the compound was 1 mM, the antagonistic effect thereof against CCR5 was 100%.

B. Calcium Influx Assay

The experimental intracellular $Ca^{2+}$ level can be regulated by the activated G protein through several mechanisms to reflect the level of the GPCR activated. Fluo-4 calcium dye from Invitrogen Corporation is a kind of fluorescent dyes commonly used in $Ca^{2+}$ detection, and the signal may be detected usually by molecular devices such as FlexStation or FLIPR. In the present invention, the $G_q$ signaling pathway is activated by $G_{i/o}$ protein-coupled CCR5 receptor through the overexpression of G16, a protein of $G_q$ family, in a CHO-CCR5 stable cell line.

Cells were cultured in a serum-free medium (alpha-MEM from Gibco) for 4 hours before the starting of the experiment, and then digested by 0.04% EDTA-PBS, and washed once with HBSS buffer (Hank's Balanced Salt Solution). The cells were resuspended in HBSS containing 2.5 mM probenecid, and then a pre-prepared mixture of Fluo-4 AM (a fluorescent dye) and Cremophor EL (polyoxyethylenated castor oil) was added into the cell suspension. After mixed homogeneously, the mixture was reacted for 40 min in an incubator at 37° C. and then centrifuging for 3 min at 800 rpm. The supernatant was discarded and the cells were washed twice with 5 mL HBSS. The cells were suspended in 11 mL HBSS and plated in 96-well plate (100 μl/well). After centrifuged for 3 min at 1000 rpm, the 96-well plate was incubated for 10 min in dark, followed by addition of 50 μl drug solution. Setting up the instrument FlexStation and adding an agonist solution (25 μl/well) were followed by determination.

[$^{35}$S]GTPγS binding assay and calcium influx assay indicate that the compounds of the present invention are CCR5 agonists, and they may inhibit the GTPγS binding induced by the activation of CCR5 by 10 nM RANTES. The inhibition effects and $IC_{50}$ are listed in table 1.

TABLE 1

| Example number | Compound number | $IC_{50}$ (nM) $^a$ |
| --- | --- | --- |
| 1 | 7a | 64.64%@300 nM |
|   |    | 26.24%@30 nM |
| 2 | 7b | 31.1 |
| 3 | 7c | 15.1 |
| 4 | 7d | 49.4 |
| 5 | 7e | 209 |
| 6 | 7f | 20 |
| 7 | 7g | 48.2 |
| 8 | 7h | 4.89 |
| 9 | 7i | 2.97 |
| 10 | 7j | 3.08 |
| 11 | 7k | 11.58 |
| 12 | 7l | 3.46 |
| 13 | 7m | 7.54 |
| 14 | 7n | 4.75 |
| 15 | 7o | 697 |
| 16 | 7p | 51.5 |
| 17 | 7q | 82 |
| 18 | 7r | 20.3 |
| 19 | 7s | 3.34 |
| 20 | 7t | 15.59%@ 300 nM |
|    |    | 3.36%@30 nM |
| 21 | 7u | 96.29%@300 nM |
|    |    | 26.52%@30 nM |
| 22 | 7v | 76.66%@300 nM |
|    |    | 17.47%@30 nM |
| 23 | 7w | 18.1 |
| 24 | 7x | 27.3 |
| 25 | 7y | 24.6 |
| 26 | 7z | 17.3 |
| 27 | 8 | 18.3 |
| 28 | 9a | 20.1 |
| 29 | 9b | 6.0 |
| 30 | 9c | 3.3 |
| 31 | 9d | 2.59 |
| 32 | 9e | 7.4 |
| 33 | 9f | 2.53 |
| 34 | 10a | ++ |
| 35 | 10b | 28.7 |

TABLE 1-continued

| Example number | Compound number | IC$_{50}$ (nM) [a] |
|---|---|---|
| 36 | 10c | 41.93%@300 nM |
|    |     | 33.46%@30 nM |
| 37 | 11  | 98.41%@300 nM |
|    |     | 48.77%@30 nM |
| 38 | 15a | 99.95%@300 nM |
|    |     | 45.25%@30 nM |
| 39 | 15b | 2.06 |
| 40 | 15c | ++ |
| 41 | 15d | ++ |
| 42 | 15e | ++ |

[a] "+++" represents the compound at 30 nM has an inhibition agains CCR5 of more than 50%; "++" represents the compound at 300 nM has an inhibition against CCR5 of more thant 50% at 300 nM; "−" represents the compound at 300 nM does not exhibit antagonistic activity agains CCR5.

Activity data listed in table 1 suggest sufficiently that the screening results of the three assays were confirmed and consistent with each other. The compounds according to the invention are antagonists with high activity of chemokine receptor CCR5, among them, 13 compounds have the inhibition activities against CCR5 receptor with an IC$_{50}$ at nM level, 18 compounds have an IC$_{50}$ at 10 nM level, and 11 compounds have a IC$_{50}$ of 100 nM level.

2. Results of Activity Assay at Cellular Level 2.1 H4DA5 Cell Model (The Operation was Performed Under P3 Experimental Conditions)

(1) H4DA5 cells: Hela cells expressing human CD4, CCR5 receptor and reporting gene Ltr-lacZ;

(2) Appropriate amounts of H4DA5 cells were plated in 96-well plate and cultured overnight;

(3) The compound to be tested and HIV-1 NL(AD8) virus were added;

(4) Incubation for 3 days (in cell incubator at 37° C.);

(5) Virus replication was determined using β-galactosidase test kit.

2.2 PBMC System of Virus Replication Model (The Operation was Performed Under P3 Experimental Conditions)

(1) PBMC cells were separated from the blood from two people (using Ficoll gradient separation method);

(2) the PBMC cells were stimulated using PHA and incubated for 3 days in a cell incubator at 37° C. at a density of 2×10$^6$ cells/ml.

(3) PBMC cells were resuspended in a RF-10 medium (RF-10/IL2) containing 100 U/mL IL-2 (30 uL RF-10/IL2 medium containing 4 times of the final concentration of the compound to be tested and 40 uL RF-10/IL2 medium containing HIV-1 Ba-L virus (1400 pfu/well) were added in the plate (200,000 cells/50 uL/well).

(4) After incubated 24 hours, RF-10/IL2 medium containing 1 time of the final concentration of the compound to be test was added in each well. After infected for 4 days, 100 ul fresh RF-10/IL2 medium containing the compound to be tested at the final concentration to replace the original medium. After incubated for 2 days, the supernatant of each well was collected, and the content of p24 was determined.

(5) The content of P24 antigen in the supernatant of each well was measured by Vironostik p24 test kit to detect the virus replication.

The experiments in H4DA5 cell model and PBMC system of virus replication model indicated that the compounds of the present invention are CCR5 antagonists, and they can inhibit the virus replication in cell models. The inhibitory effects and EC$_{50}$ are listed in table 2.

TABLE 2

| Example Number | Compound Number | IC$_{50}$ (nM) | |
|---|---|---|---|
| | | H4DA5 cell model | PBMC system of virus replication model |
| 27 | 8 | 220 | |
| 29 | 9b | 1 | 0.42 |
| Maraviroc | | 1.5 | 0.35 |

Activity data listed in table 2 suggest that the compounds of the present invention have potent inhibitory effect against virus replication at cellular level, among them, the compound 9b has an inhibitory activity EC$_{50}$ at nM level in H4DA5 cell model and PBMC system of virus replication model, which is the same order as the positive control Maraviroc (a small molecular CCR5 antagonist marketed by Pfizer Pharmaceuticals Ltd.), and the compound 8 has an EC$_{50}$ at 100 nM level in H4DA5 cell model.

Therefore, the compounds of the present invention are efficient CCR5 antagonists, and thus can be used as drugs for treating diseases mediated by CCR5, such as HIV-1 infection, autoimmune diseases, asthma, rheumatoid arthritis and chronic obstructive pulmonary diseases.

In the claims:

1. A 8-(3-aminopropyl)-3-exo-8-azabicyclo(3.2.1)octane-3-amino amide compound represented by the following formula I or a pharmaceutically acceptable salt thereof:

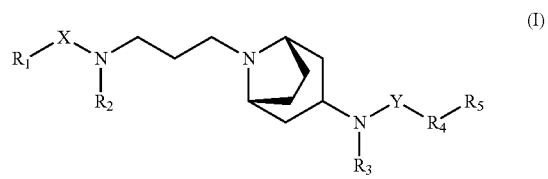

(I)

wherein, $R_1$ is a group unsubstituted or substituted by 1 to 3 substituents and selected from the group consisting of $C_1$-$C_6$ alkyl, $C_3$-$C_8$ cycloalkyl, phenyl, benzyl, naphthyl, and $C_4$-$C_7$ saturated heterocyclic group, wherein the heterocyclic group comprises 1 to 3 hetero atoms selected from the group consisting of N, O and S, the substituents are atoms or groups selected from the group consisting of $C_1$-$C_6$ alkyl, COR$_7$ and SO$_2$R$_7$;

X is OC(O), CO, NR$_6$CO or SO$_2$;

$R_2$ is a group unsubstituted or substituted by 1 to 3 substituents and selected from the group consisting of phenyl, benzyl and naphthyl, wherein the substituents are atoms or groups selected from the group consisting of $C_1$-$C_6$ alkyl, $C_2$-$C_6$ alkenyl, $C_3$-$C_7$ cycloalkyl, halogen, and CF$_3$;

$R_3$ is hydrogen, or $R_3$ together with the attached N, Y, $R_4$ and $R_5$ forms a group of 3-isopropyl-5-methyl-4-hydro-1,2,4-triazol-4-yl;

Y is C(O)O, CO, C(O)NR$_6$ or SO$_2$;

$R_4$ is a direct bond or a group unsubstituted or substituted by 1 to 3 substituents and selected from the group consisting of $C_1$-$C_6$ alkylene or $C_1$-$C_6$ alkyleneoxy, wherein the substituents are atoms or groups selected from the group consisting of $C_1$-$C_6$ alkoxy, halogen, amino, mercapto and hydroxyl;

$R_5$ is a group unsubstituted or substituted by 1 to 3 substituents and selected from the group consisting of $C_1$-$C_6$ alkyl, $C_3$-$C_8$ cycloalkyl, adamantyl, phenyl, phenoxyl, benzyl, naphthyl, $C_5$-$C_{10}$ aromatic heterocyclic group and C₄-C₇ saturated heterocyclic group, wherein the heterocyclic group comprises 1 to 3 hetero atoms selected from the group consisting of N, O and S, the substituents are atoms or groups selected from the group consisting of $C_1$-$C_6$ alkyl, $C_1$-$C_6$ alkoxy, halogen, mercapto, hydroxyl, $CF_3$, CN, $NO_2$, $NR_6R_7$, $NR_6SO_2R_7$, $SO_2R_7$ and $SO_2NR_6R_7$, or $NR_6R_7$ forms a cycloamine group;

$R_6$ is hydrogen, hydroxyl or $C_1$-$C_6$ alkyl;

$R_7$ is hydrogen or a group unsubstituted or substituted by 1 to 3 substituents and selected from the group consisting of $C_1$-$C_6$ alkyl, $C_1$-$C_6$ alkoxy, $C_3$-$C_8$ cycloalkyl, phenyl, benzyl, naphthyl, $C_5$-$C_{10}$ aromatic heterocyclic group and $C_4$-$C_7$ saturated heterocyclic group, wherein the heterocyclic group comprises 1 to 3 hetero atoms selected from the group consisting of N, O and S, the substituents are atoms or groups selected from the group consisting of $C_1$-$C_6$ alkyl, $C_1$-$C_6$ alkoxy, halogen, amino, nitro group, mercapto, hydroxyl, CN and $CF_3$.

2. The compound or pharmaceutically acceptable salt thereof according to claim 1, wherein, the compound is one represented by formula II:

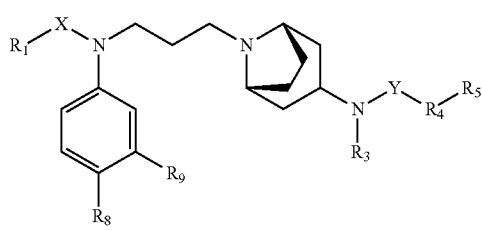

(II)

wherein, $R_1$ is 1-acetylpiperidin-4-yl, cyclohexyl, 1-methylsulfonylpiperidin-4-yl, $C_1$-$C_4$ alkyl, benzyl, phenyl or $C_1$-$C_4$ alkyl phenyl;

X is OC(O), CO, $NR_6CO$ or $SO_2$;

$R_3$ is hydrogen, or $R_3$ together with the attached N, Y, $R_4$ and $R_5$ forms a group of 3-isopropyl-5-methyl-4-hydro-1,2,4-triazol-4-yl;

Y is C(O)O, CO,C(O)NH or $SO_2$;

$R_4$ is a direct bond, $C_1$-$C_4$ alkylene, $C_1$-$C_4$ alkyleneoxy or $C_1$-$C_4$ alkylene substituted by hydroxyl;

$R_5$ is a group unsubstituted or substituted by 1 to 3 substituents and selected from the group consisting of $C_1$-$C_4$ alkyl, $C_3$-$C_8$ cycloalkyl, adamantyl, phenyl, phenoxyl, benzyl, naphthyl, or $C_5$-$C_{10}$ aromatic heterocyclic group, wherein the heterocyclic group comprises 1 to 2 hetero atoms selected from the group consisting of N, O and S, the substituents are atoms or groups selected from the group consisting of $C_1$-$C_4$ alkyl, $C_1$-$C_4$ alkoxy, halogen, hydroxyl, $CF_3$, CN, $NO_2$, $NR_6R_7$, $SO_2R_7$ and $SO_2NR_6R_7$, or $NR_6R_7$ forms a cycloamine, wherein $R_6$ is hydrogen or $C_1$-$C_6$ alkyl, and $R_7$ is hydrogen, $C_1$-$C_6$ alkyl or $C_1$-$C_6$ alkoxy;

$R_8$ and $R_9$ are each independently selected from the group consisting of hydrogen, halogen, $C_1$-$C_6$ alkyl, $C_2$-$C_6$ alkenyl, or $C_3$-$C_7$ cycloalkyl, wherein $C_1$-$C_6$ alkyl, $C_2$-$C_6$ alkenyl, or $C_3$-$C_7$ cycloalkyl is unsubstituted or substituted with halogen, hydroxyl, amino or $C_3$-$C_7$ cycloalkyl.

3. The compound or pharmaceutically acceptable salt thereof according to claim 2, wherein, $R_1$ is 1-acetylpiperidin-4-yl, cyclohexyl, 1-methylsulfonylpiperidin-4-yl, $C_1$-$C_4$ alkyl 1, benzyl, phenyl or $C_1$-$C_4$ alkyl phenyl;

X is OC(O), CO, NHCO or $SO_2$;

$R_3$ is hydrogen, or $R_3$ together with the attached N, Y, $R_4$ and $R_5$ forms a group of 3-isopropyl-5-methyl-4-hydro-1,2,4-triazol-4-yl;

$R_4$ is a direct bond, $C_1$-$C_4$ alkylene, $C_1$-$C_4$ alkyleneoxy or $C_1$-$C_4$ alkylene substituted by hydroxyl;

$R_5$ is a group unsubstituted or substituted by 1 to 3 substituents and selected from the group consisting of phenyl, phenoxyl, naphthyl, adamantyl, morpholinyl, piperazinyl, piperidinyl, pyrrolyl, thienyl, imidazolyl, furyl, pyranyl, indolyl, quinolyl, benzopyranyl, benzothienyl, benzofuryl, or benzimidazolyl, wherein the substituents are atoms or groups selected from the group consisting of $C_1$-$C_4$ alkyl, $C_1$-$C_4$ alkoxy, halogen, hydroxyl, $CF_3$, $NO_2$, $NR_6R_7$, $NR_6SO_2R_7$, and $SO_2NR_6R_7$, or $NR_6R_7$ forms a cycloamine group, wherein $R_6$ is hydrogen or $C_1$-$C_4$ alkyl, and $R_7$ is hydrogen, $C_1$-$C_4$ alkyl or $C_1$-$C_4$ alkoxy;

$R_8$ is hydrogen, halogen or $C_1$-$C_4$ alkyl;

$R_9$ is hydrogen or halogen.

4. The compound or pharmaceutically acceptable salt thereof according to claim 3, wherein, $R_1$ is 1-acetylpiperidin-4-yl;

X is CO.

5. The compound or pharmaceutically acceptable salt thereof according to claim 1, wherein, the compound is one selected from the following compounds:

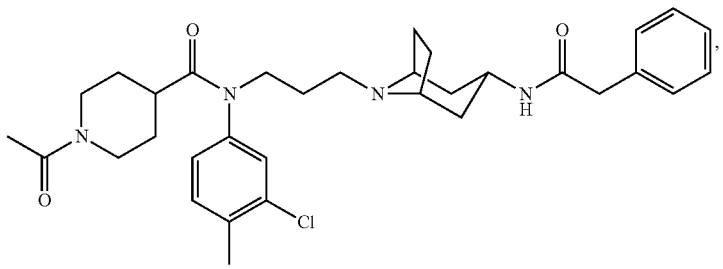

-continued
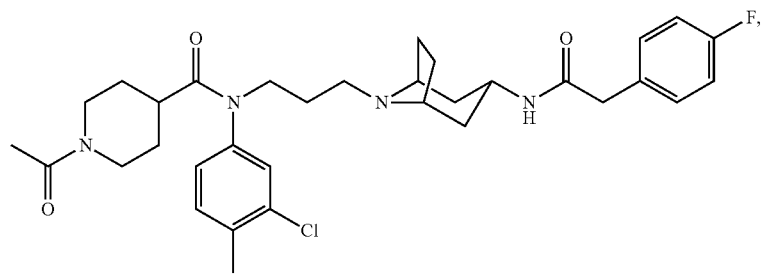
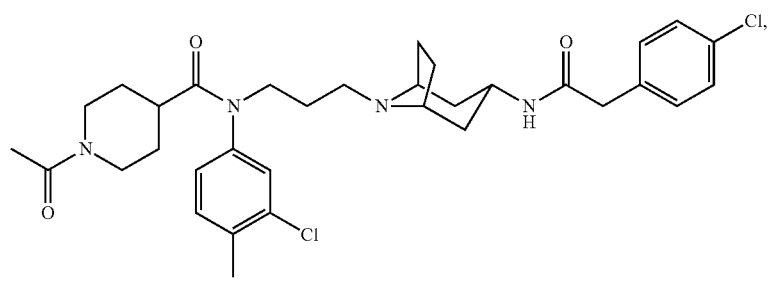
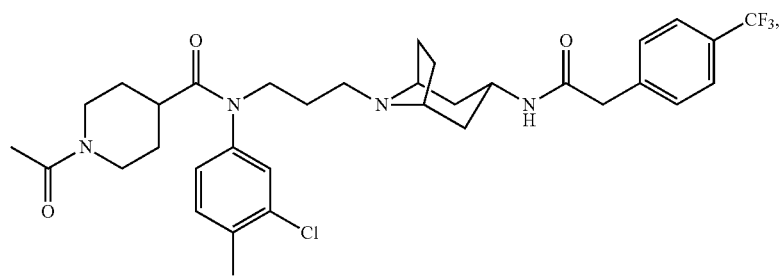
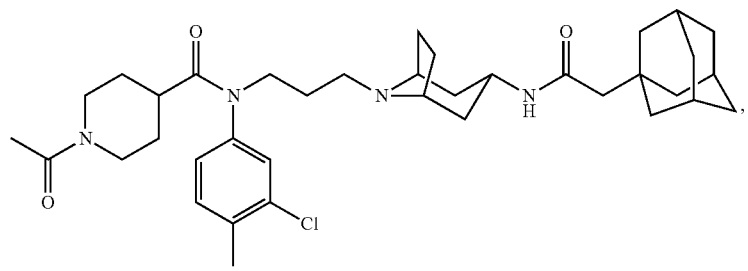
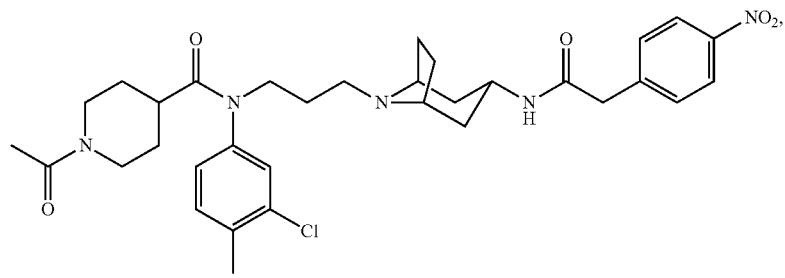
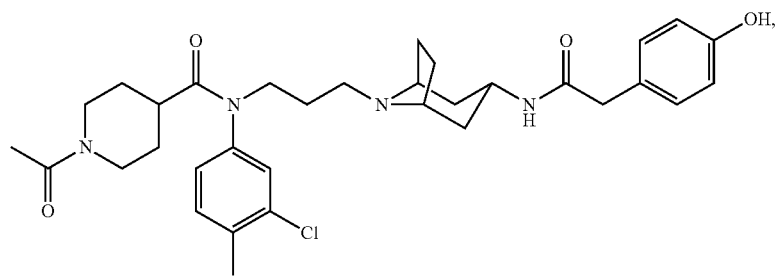

-continued
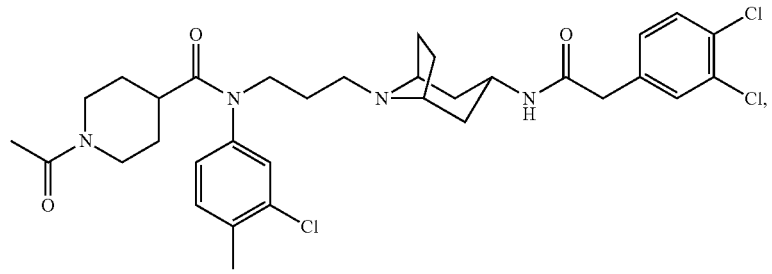
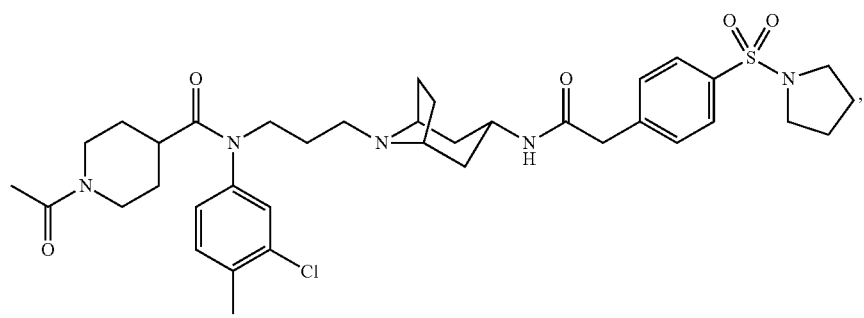
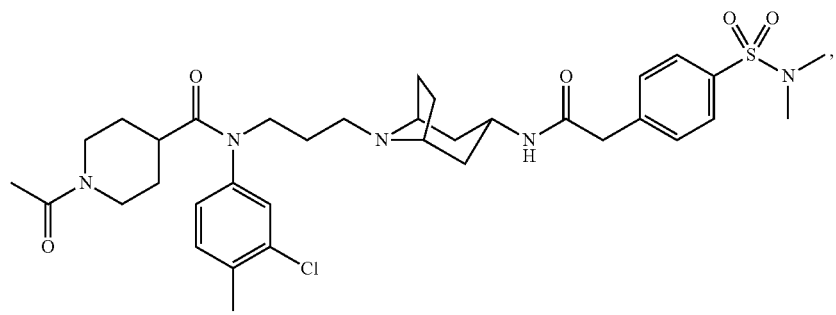
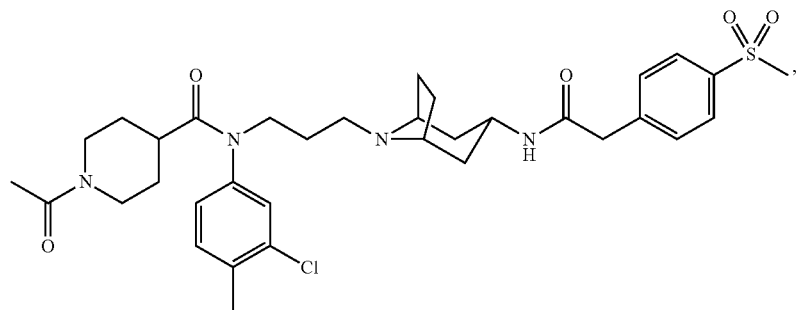
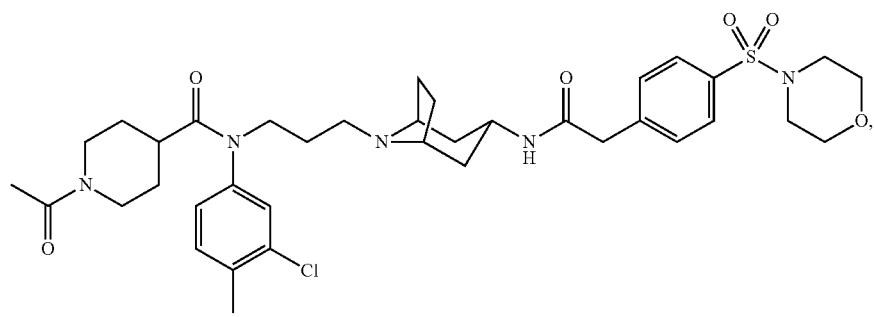

-continued
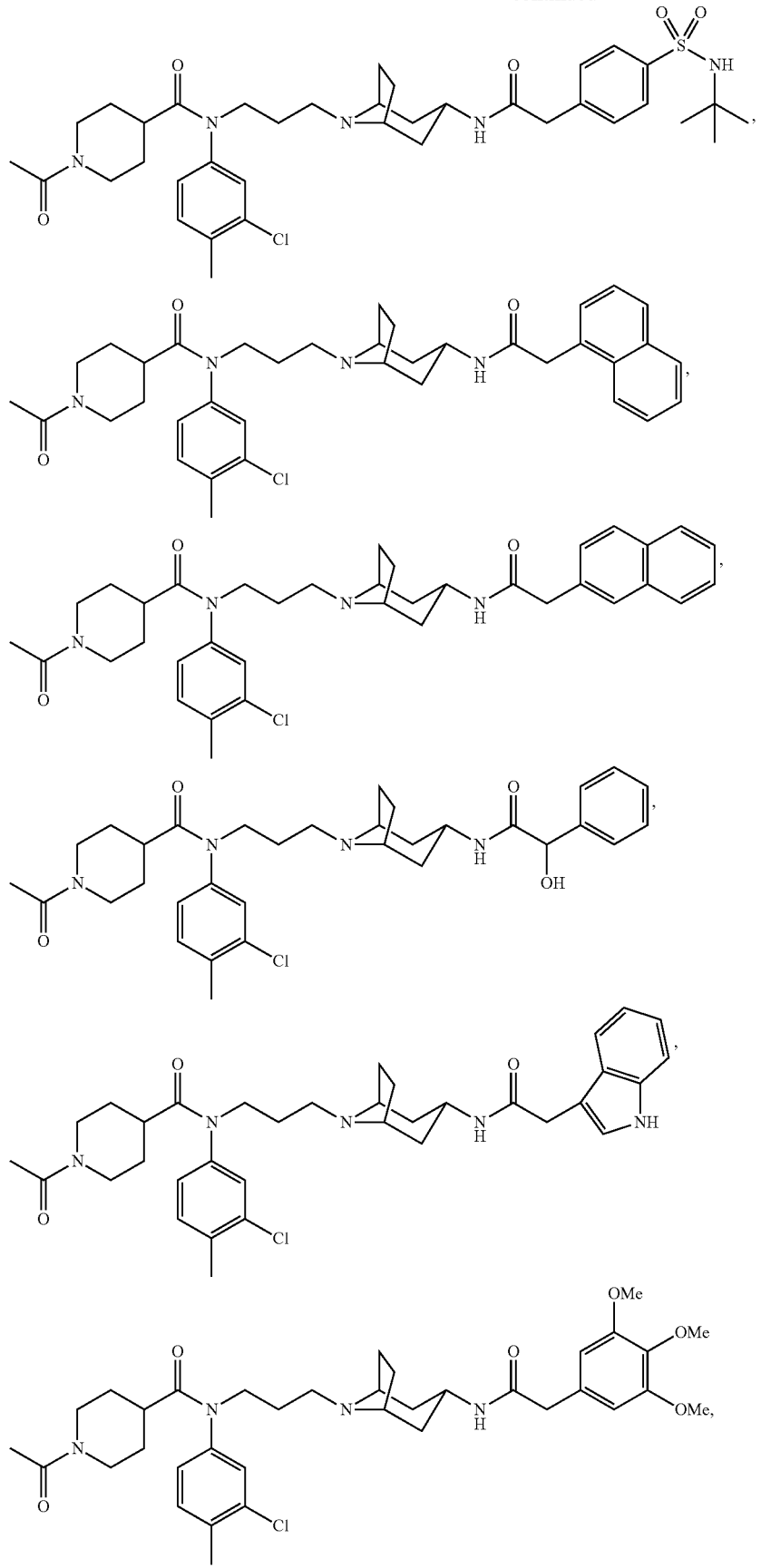

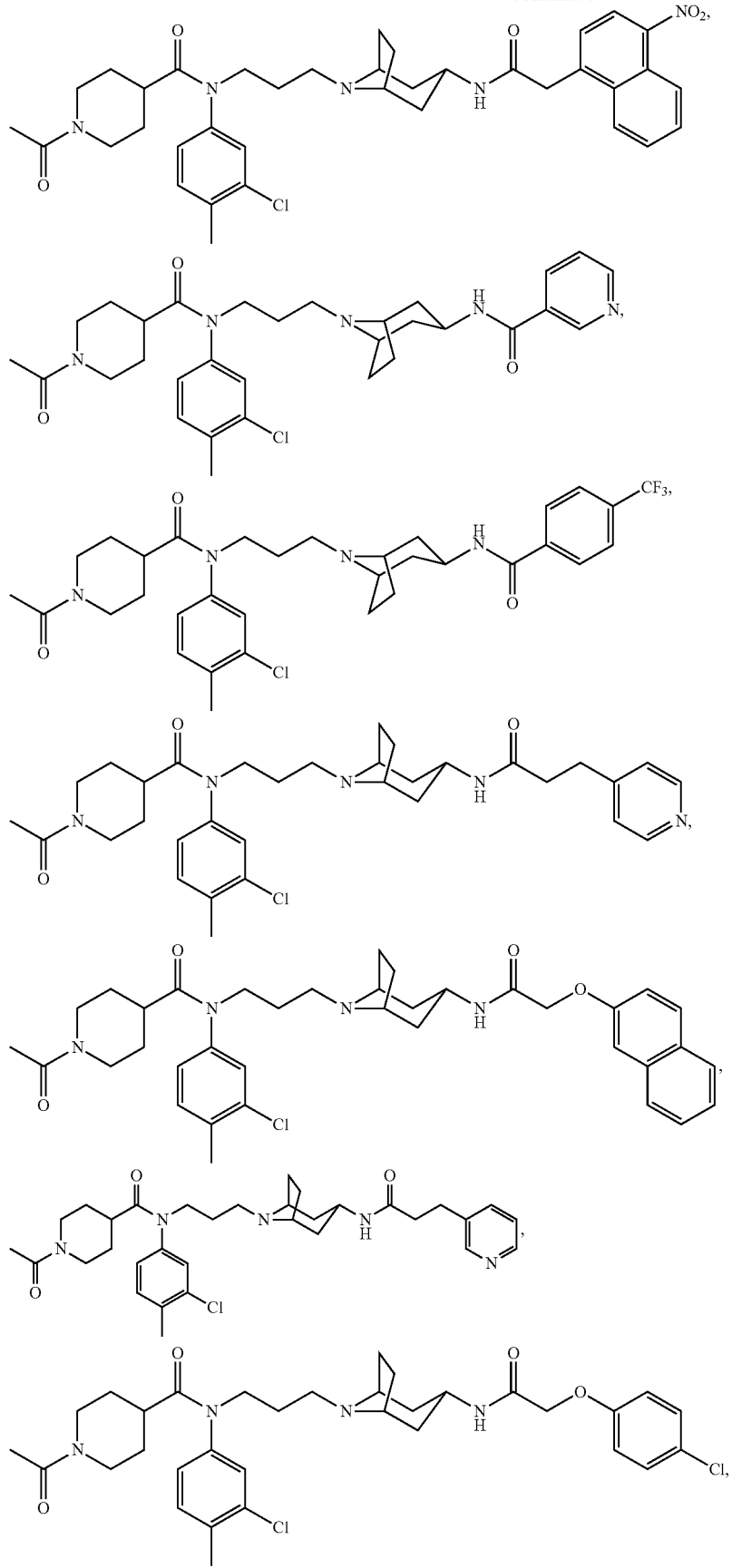

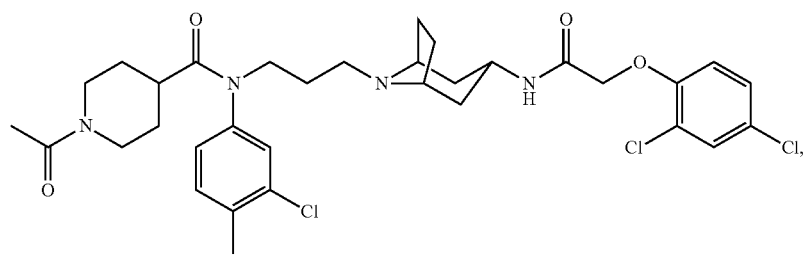
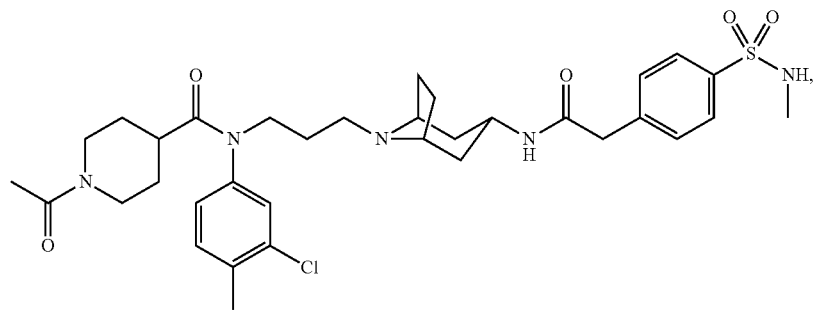
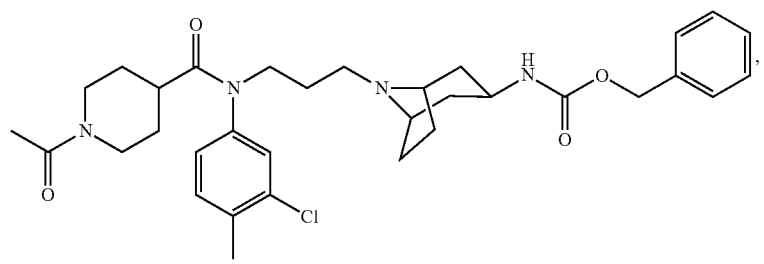
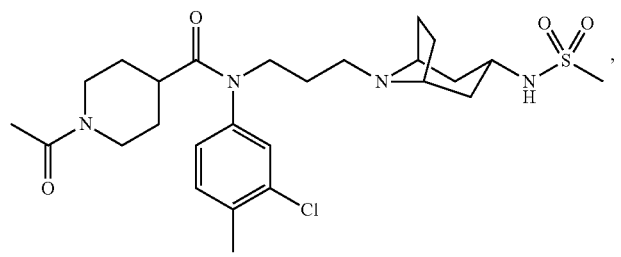
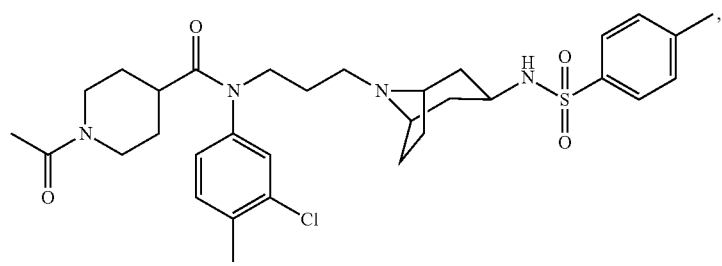
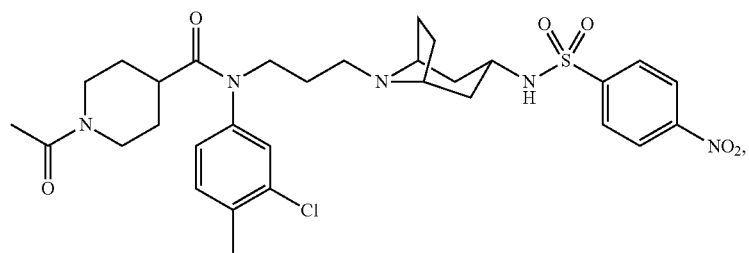

-continued
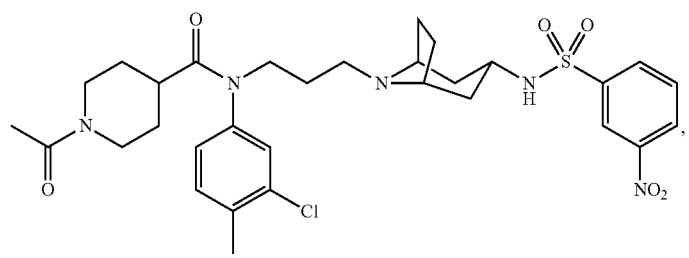
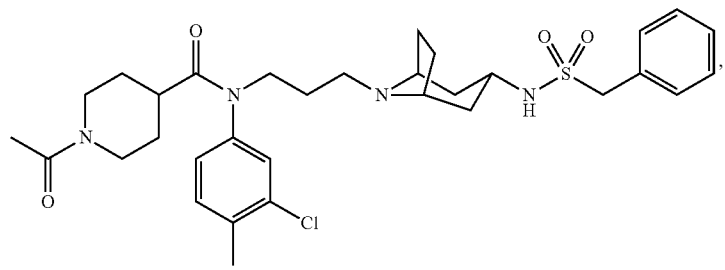
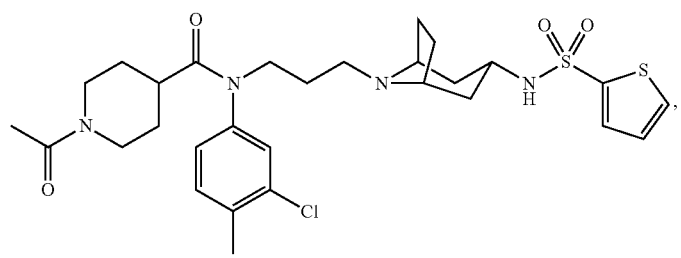
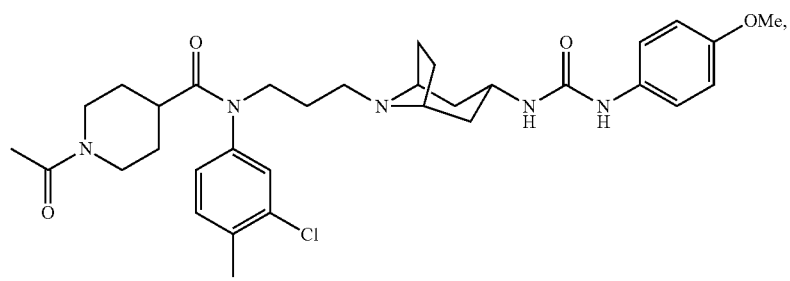
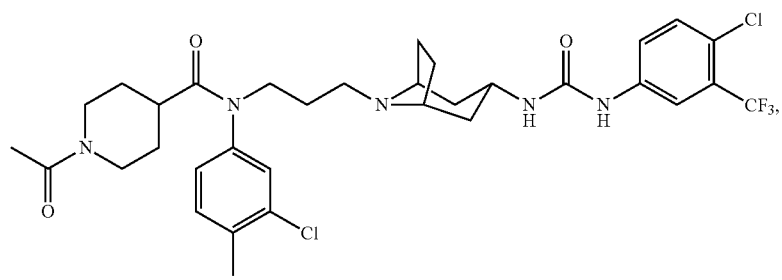
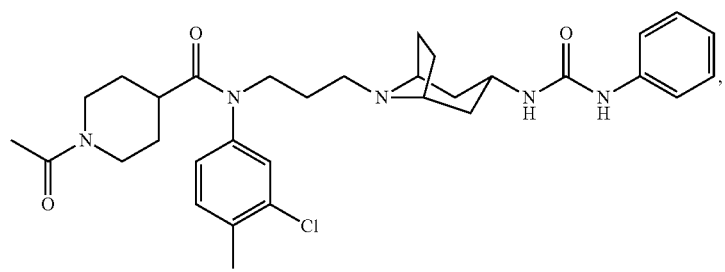

-continued
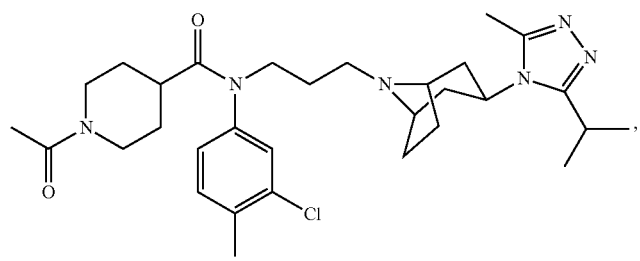
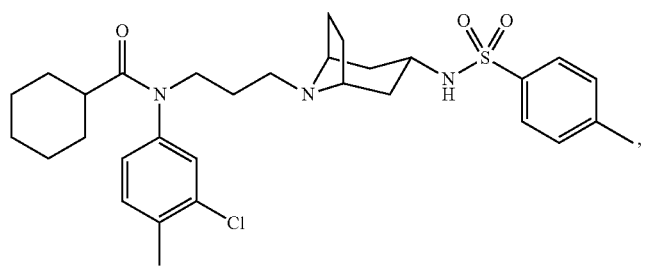
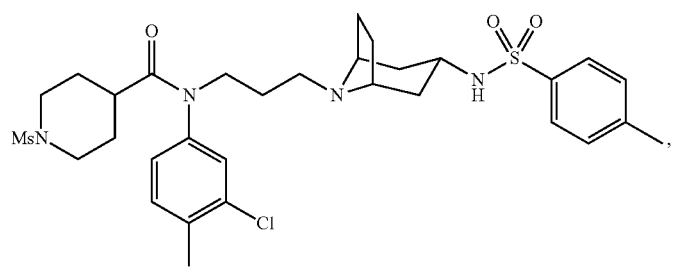
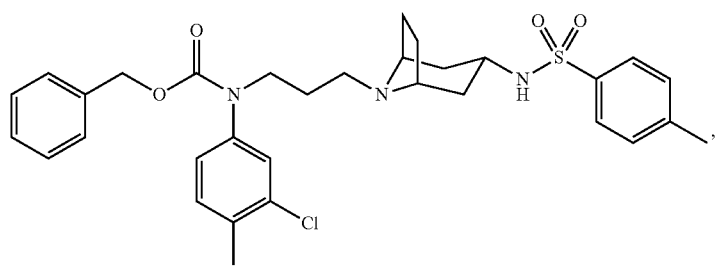
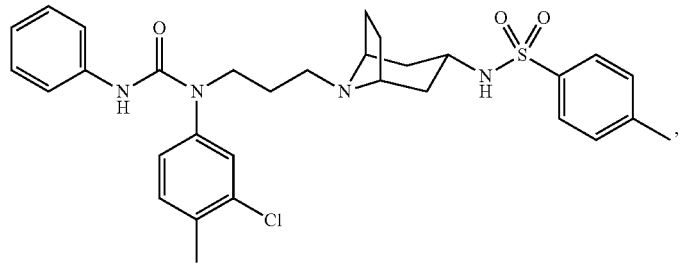
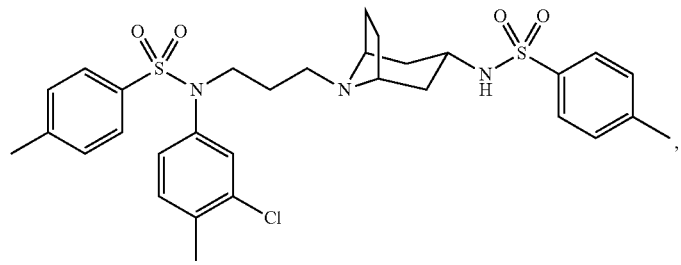

71 72

-continued

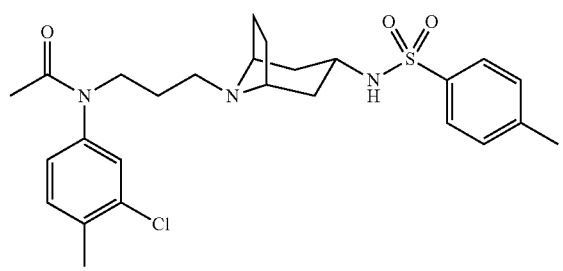
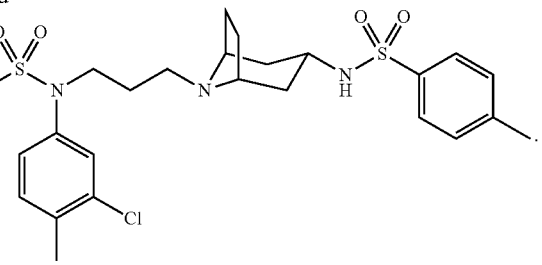

or

6. A method for preparing the 8-(3-aminopropyl)-3-exo-8-azabicyclo (3.2.1)octane-3- amino amide compound according to claim 1, comprising the following steps:

through a nucleophilic substitution to prepare a compound V, the 8-(3-aminopropyl)-3-exo-8-azabicyclo (3.2.1)octane-3-amino amide compound; or,

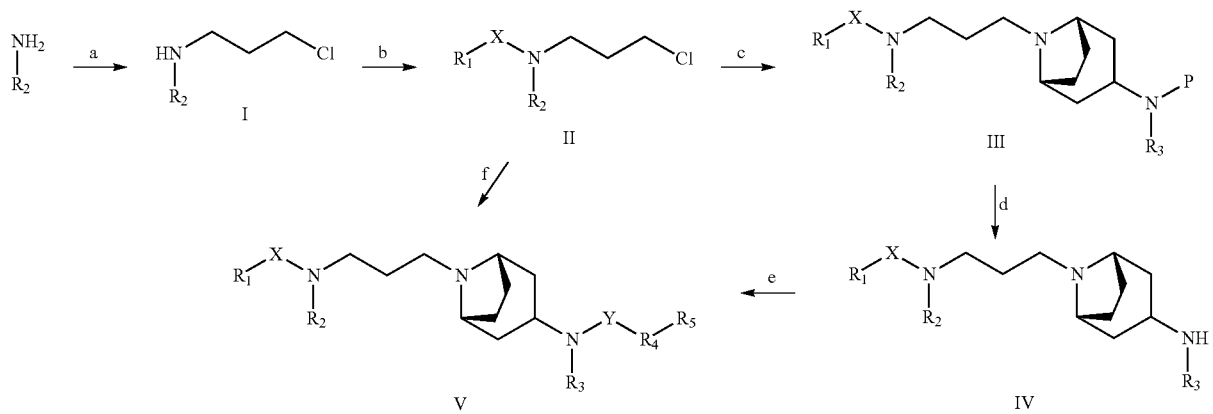

wherein, $R_1$, $R_2$, $R_3$, $R_4$, $R_5$, X and Y are defined the same as those in the referred claim 1;

P is an amino-protecting group selected from the group consisting of t-butoxycarbonyl, benzyloxycarbonyl, benzyl, 9-fluorenylmethoxycarbonyl, $CH_3CO$ and $CH_3OCO$;

Step a): N-substituted 3-chloropropylamine compound I is prepared by nucleophilic substitution of $R_2NH_2$ and 1-bromo-3-chloropropane in the presence of an alkali;

Step b): the N-substituted 3-chloro-propylamine compound I reacts with an aldehyde or a ketone by a reductive amination, or with an acid by a coupling reaction, or with a halogenated hydrocarbon by a nucleophilic substitution to obtain a N-trisubstituted 3-chloropropylamine compound II;

Step c): a 3-exo-3-amino-8-azabicyclo (3.2.1)octane secondary amine compound protected at 3-N atom reacts with the N-trisubstituted 3-chloropropylamine compound II by a nucleophilic substitution in the presence of an alkali to obtain a 8-(3-aminopropyl)-3-exo-8-azabicyclo (3.2.1)octane-3-amino amide compounds III protected at the N atom;

Step d): the amine protecting groups of the compound III is deprotected by acidic or alkalaline hydrolysis or hydrogenolysis according to the amine protecting groups to obtain a compound IV;

Step e): the free amine compound IV reacts with an acid through a coupling reaction, or with an acyl chloride through a substitution reaction, or with an isocyanate through an addition reaction, or with a halohydrocarbon Step f): the N-trisubstituted 3-chloropropylamine compound II reacts with a 3-exo-8-azabicyclo (3.2.1)octane-3-amino amide compound through a nucleophilic substitution in the presence of an alkali to prepare the compound V, the 8-(3-aminopropyl)-3-exo-8-azabicyclo (3.2.1)octane-3-amino amide compound.

7. The preparation method according to claim 6, wherein, the 3-exo-3-amino-8-azabicyclo(3.2.1)octane secondary amine compound protected at 3-N atom in step c) is prepared by the follow steps:

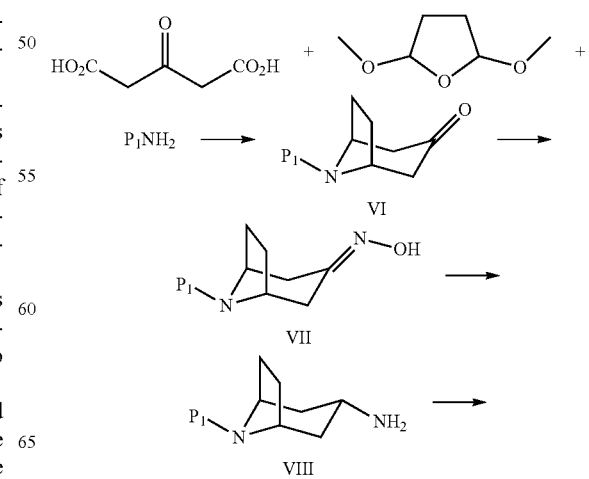

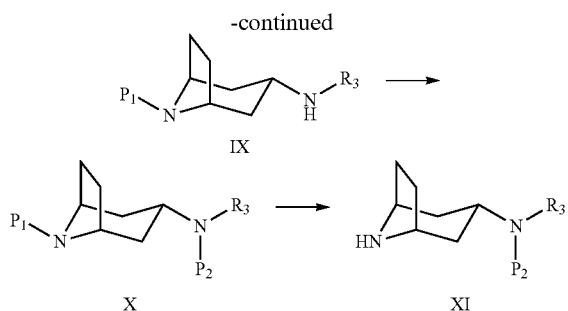

wherein $P_1$ and $P_2$ are respectively an amino-protecting group selected from the group consisting of t-butoxycarbonyl, benzyloxycarbonyl, benzyl, 9-fluorenylmethoxycarbonyl, $CH_3CO$ and $CH_3OCO$;

a protected amino compound reacts with 3-carbonyl-1,5-glutaric acid and 2,5-dimethoxytetrahydrofuran through a Robinson-Schopf reaction to prepare a protected 8-azabicyclo (3.2.1)octan-3-one VI, which is then subject to an oximation reaction to obtain a compound VII; the compound VII is reduced to prepare a protected 3-exo-8-azabicyclo (3.2.1)otane-3-amino compound VIII; various substituents $R_3$ is introduced and the secondary amine compound is protected to obtain a compound X, which is deprotected the protecting group P1 to prepare a 3-exo-3-amino-8-azabicyclo(3.2.1) octane secondary amine compound XI protected at 3-N atom.

8. A pharmaceutical composition for treating diseases mediated by CCR5, which comprising therapeutically effective amount of one or more compounds selected from the 8-(3-aminopropyl)-3-exo-8-azabicyclo(3.2.1)octane-3-amino amide compound or pharmaceutically acceptable salt thereof according claim 1 and pharmaceutically acceptable adjuvants.

9. The pharmaceutical composition according to claim 8, which further comprises a proteinase inhibitor and/or a reverse transcriptase inhibitor.

10. A method of treating diseases mediated by CCR5 comprising administering to a subject in need thereof an effective amount of the 8-(3-aminopropyl)-3-exo-8-azabicyclo(3.2.1) octane-3-amino amide compound or pharmaceutically acceptable salt thereof according to claim 1, wherein the diseases are selected from the group consisting of HIV infection, asthma, rheumatoid arthritis, autoimmune diseases and chronic obstructive pulmonary diseases.

* * * * *